us011179036B2

(12) United States Patent
Kondo et al.

(10) Patent No.: US 11,179,036 B2
(45) Date of Patent: Nov. 23, 2021

(54) CONTROL METHOD OF INFORMATION TERMINAL AND COMPUTER-READABLE RECORDING MEDIUM

(71) Applicant: PANASONIC CORPORATION, Osaka (JP)

(72) Inventors: Kenji Kondo, Fukui (JP); Kazutoyo Takata, Fukui (JP); Kazuki Kozuka, Fukui (JP); Hirohiko Kimura, Fukui (JP); Toyohiko Sakai, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 252 days.

(21) Appl. No.: 16/433,905

(22) Filed: Jun. 6, 2019

(65) Prior Publication Data

US 2019/0307327 A1    Oct. 10, 2019

Related U.S. Application Data

(63) Continuation of application No. 14/800,084, filed on Jul. 15, 2015, now Pat. No. 10,349,833, which is a
(Continued)

(51) Int. Cl.
  *A61B 5/00* (2006.01)
  *G06F 16/24* (2019.01)
  (Continued)

(52) U.S. Cl.
  CPC ............... *A61B 5/00* (2013.01); *A61B 6/463* (2013.01); *G06F 16/24* (2019.01); *G06F 16/248* (2019.01);
  (Continued)

(58) Field of Classification Search
  USPC .......................................... 705/2, 3
  See application file for complete search history.

(56) References Cited

U.S. PATENT DOCUMENTS

| 6,230,321 B1 | 5/2001 | Kim |
| 2007/0242069 A1 | 10/2007 | Matsue et al. |

(Continued)

FOREIGN PATENT DOCUMENTS

| JP | 2008-257292 A | 10/2008 |
| JP | 2012-035124 A | 2/2012 |

OTHER PUBLICATIONS

Akira Oosawa and four others, "Development of "SYNAPSE Case Match", Content-based Image Retrieval System for Supporting Image Diagnosis", Fujifilm Research Development, FUJIFILM Corporation, Mar. 27, 2013, No. 58, pp. 11-14. (Year: 2013).*
(Continued)

*Primary Examiner* — Joshua B Blanchette
(74) *Attorney, Agent, or Firm* — Greenblum & Bernstein, P.L.C.

(57) ABSTRACT

A control method of an information terminal includes sensing specification information indicating a region of interest in a medical image, receiving from a case retrieval system one or more similar medical images each having a prescribed degree of similarity with a feature quantity of the region of interest indicated by the specification information in accordance with the region of interest, and displaying the medical image that is managed by a medical information management system in a first display region that is displayed on the display and displaying thumbnail views of a plurality of similar medical images received from the case retrieval system in a second display region that differs from the first display region.

12 Claims, 75 Drawing Sheets

Related U.S. Application Data continuation of application No. PCT/JP2014/002054, filed on Apr. 9, 2014.

(51) Int. Cl.
| | | |
|---|---|---|
| G06F 16/248 | (2019.01) | |
| G16H 50/70 | (2018.01) | |
| G16H 15/00 | (2018.01) | |
| G16H 30/40 | (2018.01) | |
| G06F 16/583 | (2019.01) | |
| A61B 6/00 | (2006.01) | |
| G16H 30/20 | (2018.01) | |

(52) U.S. Cl.
CPC ........ *G06F 16/583* (2019.01); *G16H 15/00* (2018.01); *G16H 30/20* (2018.01); *G16H 30/40* (2018.01); *G16H 50/70* (2018.01); *A61B 6/465* (2013.01); *A61B 6/469* (2013.01)

(56) References Cited

U.S. PATENT DOCUMENTS

| | | | |
|---|---|---|---|
| 2008/0243395 A1 | 10/2008 | Oosawa et al. | |
| 2009/0225102 A1 | 9/2009 | Okubo et al. | |
| 2011/0105879 A1* | 5/2011 | Masumoto | G16H 30/20 |
| | | | 600/407 |

OTHER PUBLICATIONS

Radiology Assistant by Robin Smithuis available at https://radiologyassistant.nl/chest/chest-x-ray/lung-disease, published Feb. 1, 2014 (Year: 2014).*

Oosawa et al., "Development of "SYNAPSE Case Match", Content-based Image Retrieval System for Supporting Image Diagnosis", Fujifilm Research & Development (No. 58), Mar. 27, 2013, pp. 11-14.

Nemoto et al., "Improvement of Tumor Detection Performance in Mammograms by Feature Selection from a Large Number of Features and Proposal of Fast Feature Selection Method", IEICE Transactions on Information and Systems D-II, vol. J88-D-II, No. 2, Feb. 2005, pp. 416-426, with English language Abstract.

International Search Report in PCT/JP2014/002054, dated Jun. 3, 2014.

Preeti Aggarwal, "Semantic and Content-Based Medical Image Retrieval for Lung Cancer Diagnosis with the Inclusion of Expert Knowledge and Proven Pathology," Proceedings of the 2013 IEEE Second International Conference on Image Information Processing, pp. 346-351. (Year: 2013).

Jan. 22, 2018 Office Action in U.S. Appl. No. 14/800,084.
Jul. 2, 2018 Office Action in U.S. Appl. No. 14/800,084.

* cited by examiner

FIG. 8

| DISEASE NAME LIST 730 | |
|---|---|
| MYCOSIS | 14 |
| ASPERGILLOSIS | 8 |
| CRYPTOCOCCOSIS | 6 |
| NEOPLASTIC | 13 |
| LUNG CANCER | 10 |
| METASTATIC LUNG CANCER | 3 |
| NONNEOPLASTIC | 6 |
| LUNG ABSCESS | 4 |
| SARCOIDOSIS | 1 |
| SEPTIC EMBOLI | 1 |
| MYCOBACTERIOSIS | 6 |
| NONTUBERCULOUS MYCOBACTERIA | 4 |
| TUBERCULOSIS | 2 |
| TUBERCULOSIS | 2 |
| BRONCHIECTASIS | 1 |
| ... | 1 |

LESION DISTRIBUTION  /750

☐ DIFFUSE /751  ☐ MULTIPLE /755

▦ SEGMENTAL /752  ▦ SUBPLEURAL /756

☐ BRONCHIAL /753  ☐ HEMATOGENOUS /757

☐ BILATERAL /754

FIG. 12

LESION DISTRIBUTION  /750

☐ DIFFUSE /751   ☐ MULTIPLE /755
▨ SEGMENTAL /752  ▨ SUBPLEURAL /756
☑ BRONCHIAL /753  ☐ HEMATOGENOUS /757
☐ BILATERAL /754

LESION DISTRIBUTION  750

- ☑ DIFFUSE  751
- ▨ SEGMENTAL  752
- ☐ BRONCHIAL  753
- ☐ BILATERAL  754
- ☐ MULTIPLE  755
- ▨ SUBPLEURAL  756
- ☑ HEMATOGENOUS  757

| HISTORY ID | SIMILAR CASE ID |
|---:|---|
| 1 | SIM2393 |
| 2 | SIM3215 |
| 3 | SIM0782 |
| 4 | SIM1522 |
| ... | |

| 1100 | PATIENT ID | 123456 |
| --- | --- | --- |
| 1200 | NAME | TARO PANA |
| 1300 | AGE | 28 |
| 1400 | GENDER | MALE |
| 1500 | MEDICAL HISTORY | NONE |
| 1600 | FAMILY MEDICAL HISTORY | NONE |
| 1700 | CHIEF COMPLAINT | COUGHING |
| 1800 | EXAMINATION INFORMATION | (SEE Fig. 23) |
| 1900 | DEFINITIVE DIAGNOSIS | MYCOPLASMA PNEUMONIA |

| 1810 | EXAMINATION ID | 13227895 |
|---|---|---|
| 1820 | EXAMINATION DATE/TIME | 10:00, 5 FEB. 20XX |
| 1830 | EXAMINATION TYPE | BLOOD TEST |
| 1840 | EXAMINATION RESULT | YYYY1 |

| EXAMINATION ID | 13227903 |
|---|---|
| EXAMINATION DATE/TIME | 11:00, 5 FEB. 20XX |
| EXAMINATION TYPE | PLAIN RADIOGRAPHY (CHEST) |
| EXAMINATION RESULT | YYYY2 |

| EXAMINATION ID | 13227989 |
|---|---|
| EXAMINATION DATE/TIME | 9:00, 9 FEB. 20XX |
| EXAMINATION TYPE | CT (CHEST) |
| EXAMINATION RESULT | YYYY3 |

| EXAMINATION ID | 132279989 |
|---|---|
| FINDINGS | MULTIPLE NODULES 0.5 cm TO 1 cm IN SIZE HAVE BEEN FOUND IN RIGHT LUNG FIELD… |
| DIAGNOSIS | INFLAMMATORY NODULES OR TUBERCULOSIS IS SUSPECTED. |

| 4000 | |
|---|---|
| 4100 SIMILAR CASE ID | SIM5232 |
| 4200 SLICE ID | CT149391025 |
| 4300 REGION OF INTEREST INFORMATION | $x_l, y_t, x_r, y_b$ |
| 4400 IMAGE FEATURE DATA | f1, f2, f3, ..., fN |
| 4500 THUMBNAIL IMAGE DATA | $(I_{0,0}, I_{0,1}, ..., I_{w-1, h-1})$ |
| 4600 LESION DISTRIBUTION INFORMATION | |
| 4700 DEFINITIVE DIAGNOSIS (BROADLY CATEGORIZED DISEASE NAME) | NEOPLASTIC |
| 4800 DEFINITIVE DIAGNOSIS (FINELY CATEGORIZED DISEASE NAME) | LUNG CANCER |

| | |
|---|---|
| 4610 DIFFUSE | 1 |
| 4620 SEGMENTAL | 0 |
| 4630 BRONCHIAL | 0 |
| 4640 BILATERAL | 1 |
| 4650 MULTIPLE | 1 |
| 4660 SUBPLEURAL | 0 |
| 4670 HEMATOGENOUS | 1 |

FIG. 29

| PATIENT ID | PATIENT NAME | EXAMINATION DATE/TIME | EXAMINATION ID | EXAMINATION TYPE |
|---|---|---|---|---|
| 443982 | ICHIRO YAMADA | 20XX/12/1 | 23982874 | MR (HEAD) |
| 123456 | TARO PANA | 20XX/5/8 | 13227989 | CT (CHEST) |
| 345455 | ... | ... | ... | ... |
| 235982 | ... | ... | ... | ... |

～800

| SERIES ID | DEFINITION | IMAGE |
|---|---|---|
|  |  |  |
|  |  |  |
|  |  |  |

| PATIENT ID | PATIENT NAME | EXAMINATION DATE/TIME | EXAMINATION ID | EXAMINATION TYPE |
|---|---|---|---|---|
| 443982 | ICHIRO YAMADA | 20XX/12/1 | 23982874 | MR (HEAD) |
| 123456 | TARO PANA | 20XX/5/8 | 13227989 | CT (CHEST) |
| 345455 | ... | ... | ... | ... |
| 235982 | ... | ... | ... | ... |

~800

| SERIES ID | DEFINITION | IMAGE |
|---|---|---|
| CT152729 | LUNG WINDOW SETTING<br>SLICE THICKNESS : 5 mm | |
| CT152730 | LUNG WINDOW SETTING<br>SLICE THICKNESS : 1 mm | |
| CT152731 | MEDIASTINAL WINDOW SETTING<br>SLICE THICKNESS : 5 mm | |

| DISEASE NAME ID | BROADLY CATEGORIZED DISEASE NAME | FINELY CATEGORIZED DISEASE NAME | NUMBER OF CASES | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA | 4 | ... |
| ... | ... | ... | ... | ... |

FIG. 36

| DISEASE NAME LIST | 730 |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA | 4 |
| METASTATIC LUNG CANCER | 3 |
| TUBERCULOSIS | 2 |
| INFLAMMATORY NODULE | 1 |
| SEPTIC EMBOLI | 1 |
| BRONCHIECTASIS | 1 |
| UNKNOWN | 1 |

FIG. 38

| DISEASE NAME LIST | 730 |
|---|---|
| MYCOSIS | 14 |
|   ASPERGILLOSIS | 8 |
|   CRYPTOCOCCOSIS | 6 |
| NEOPLASTIC | 13 |
|   LUNG CANCER | 10 |
|   METASTATIC LUNG CANCER | 3 |
| NONNEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NONTUBERCULOUS MYCOBACTERIA | 4 |
|   TUBERCULOSIS | 2 |
| OTHER | 2 |
|   BRONCHIECTASIS | 1 |
|   ... | 1 |

FIG. 39
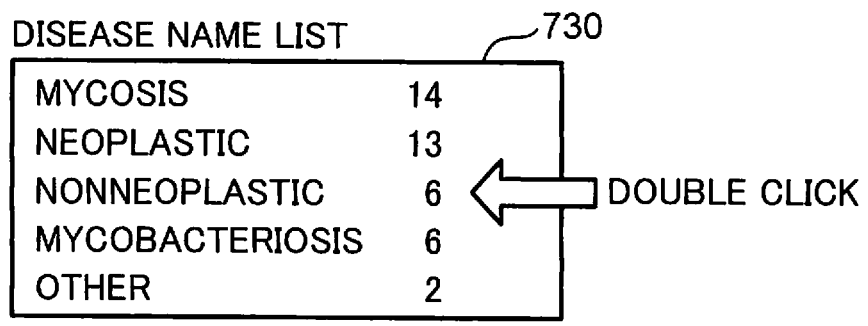
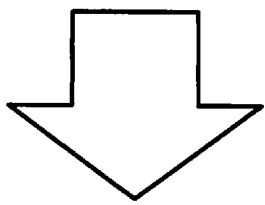
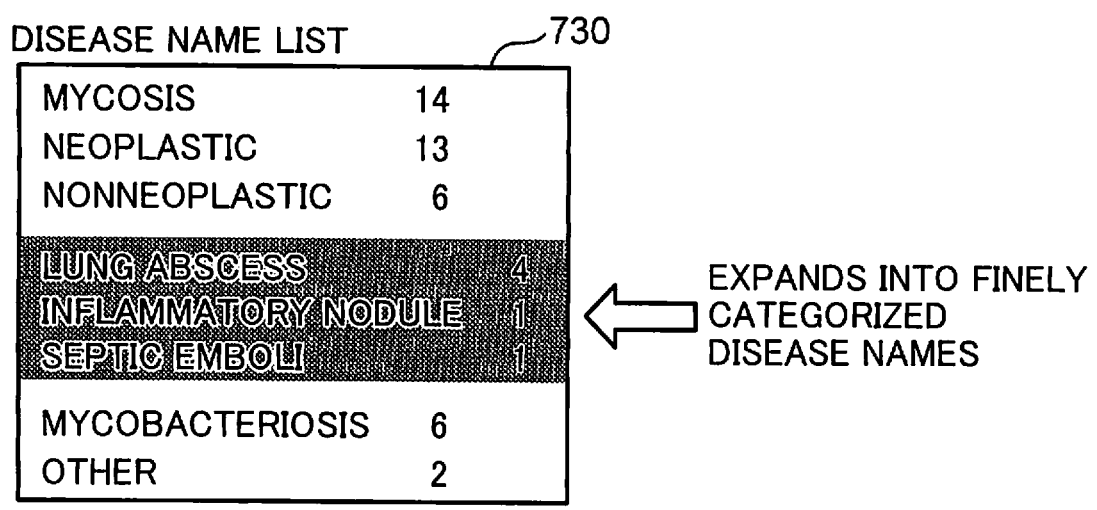

FIG. 40

| DISTRIBUTION NAME | NUMBER OF CASES | SIMILAR CASE ID |
|---|---|---|
| DIFFUSE | 3 | SIM2521, SIM4123, SIM5225 |
| SEGMENTAL | 0 | NONE |
| BRONCHIAL | 2 | SIM0006, SIM1892, SIM4399 |
| BILATERAL | 12 | ... |
| MULTIPLE | 22 | ... |
| SUBPLEURAL | 0 | NONE |
| HEMATOGENOUS | 5 | ... |

| USER ID | NUMBER OF COLUMNS | NUMBER OF ROWS | POSITION OF DIAGNOSIS OBJECT CASE |
|---|---|---|---|
| U01 | 2 | 2 | (1,1) |
| U02 | 3 | 2 | (2,1) |
| U03 | 3 | 3 | (2,2) |
| ... | ... | ... | ... |

| USER ID | TERMINAL ID | NUMBER OF COLUMNS | NUMBER OF ROWS | POSITION OF DIAGNOSIS OBJECT CASE |
|---|---|---|---|---|
| U01 | T02 | 2 | 2 | (1,1) |
| | T04 | 3 | 2 | (2,1) |
| U02 | T02 | 3 | 3 | (2,2) |
| ... | ... | ... | ... | ... |

| NUMBER OF ROWS | 2 |
|---|---|
| NUMBER OF COLUMNS | 2 |

~4411

| POSITION | SLICE ID |
|---|---|
| 1ST-ROW, 1ST-COLUMN | CT12353515 |
| 1ST-ROW, 2ND-COLUMN | — |
| 2ND-ROW, 1ST-COLUMN | — |
| 2ND-ROW, 2ND-COLUMN | — |

| NUMBER OF ROWS | 2 |
| --- | --- |
| NUMBER OF COLUMNS | 2 |

~4411

| LOCATION | SLICE ID |
| --- | --- |
| 1ST-ROW, 1ST-COLUMN | CT12353515 |
| 1ST-ROW, 2ND-COLUMN | CT34298362 |
| 2ND-ROW, 1ST-COLUMN | — |
| 2ND-ROW, 2ND-COLUMN | — |

~4412

FIG. 57
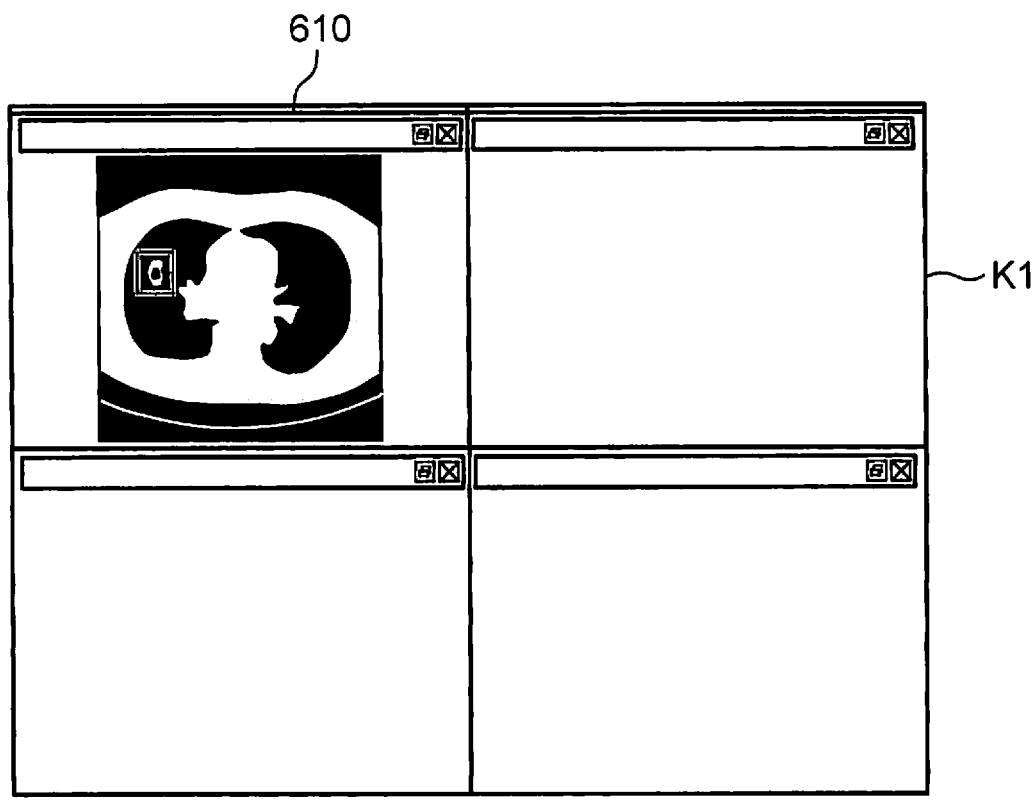
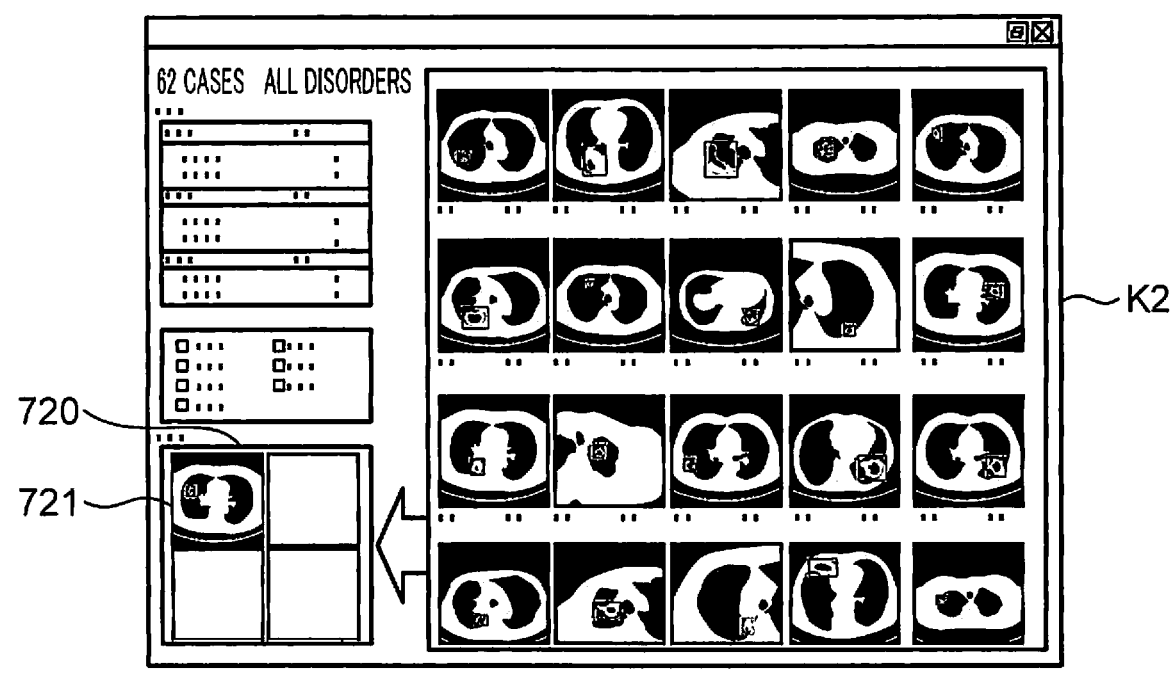

FIG. 58
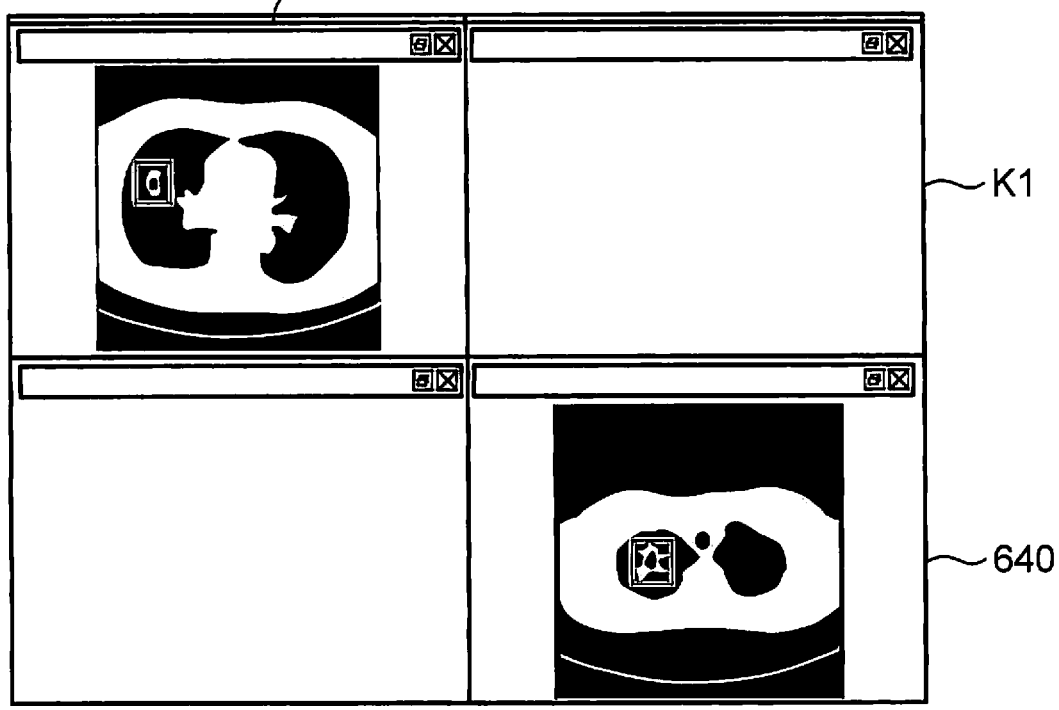
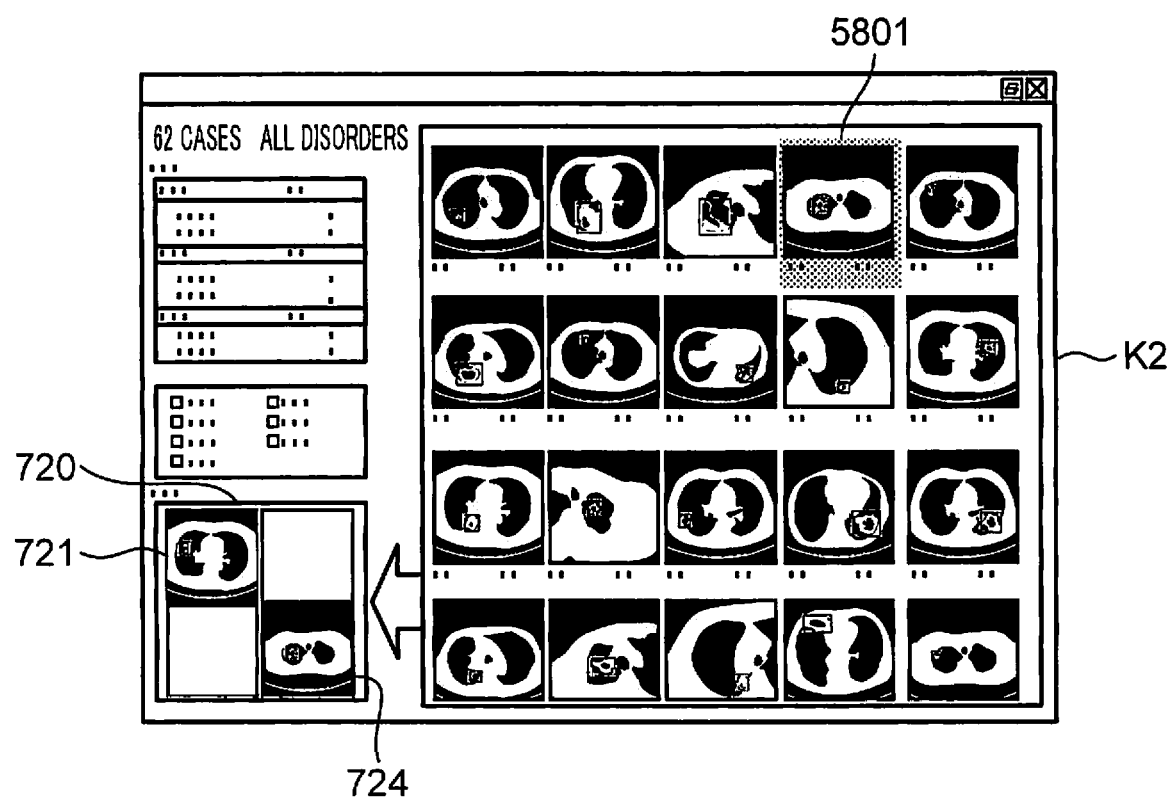

FIG. 59
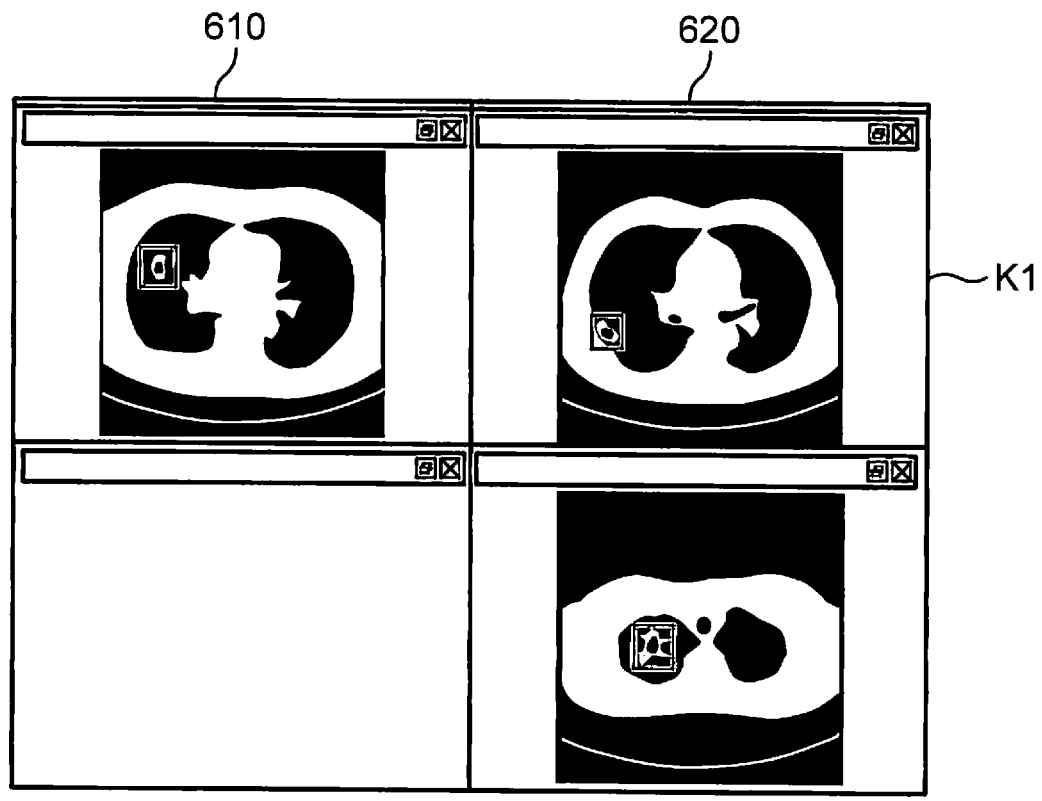
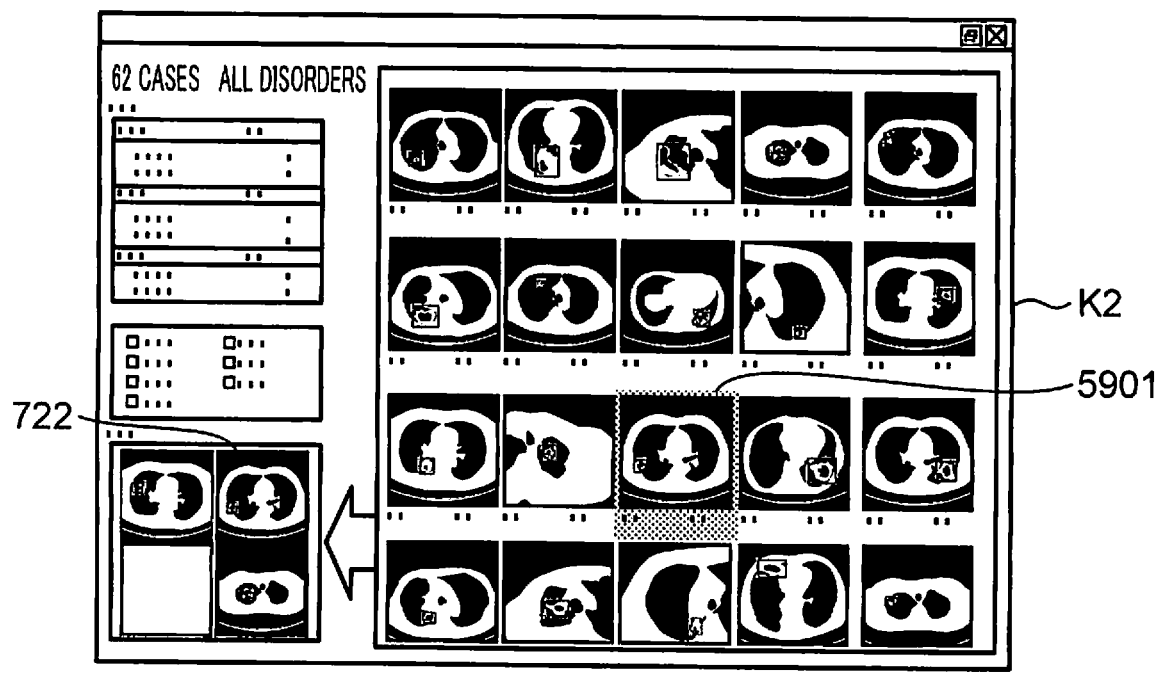

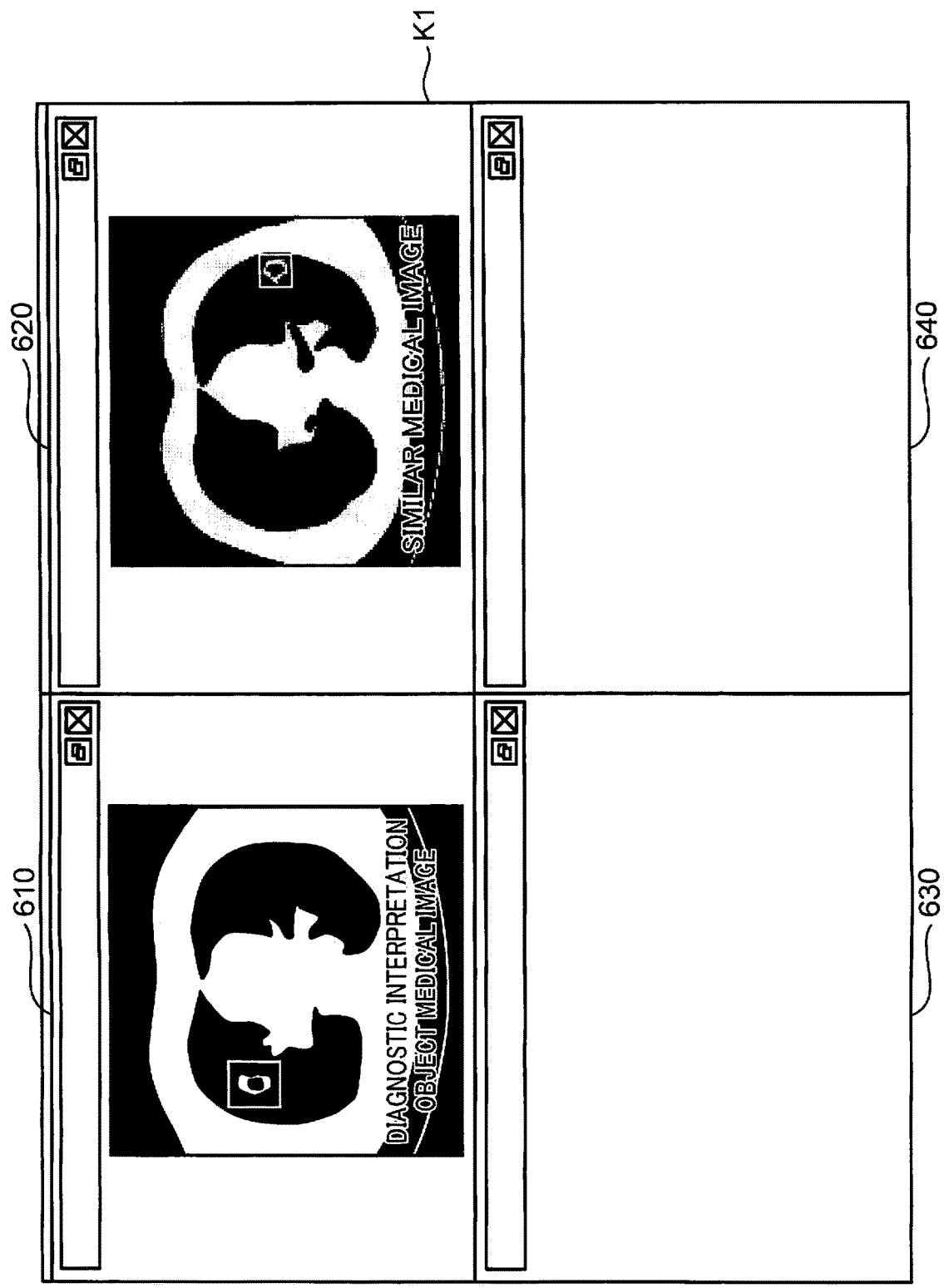

CONTROL METHOD OF INFORMATION TERMINAL AND COMPUTER-READABLE RECORDING MEDIUM

CROSS-REFERENCE TO RELATED APPLICATIONS

This application is a continuation of U.S. application Ser. No. 14/800,084, filed Jul. 15, 2015, pending, which is a continuation of International Patent Application No. PCT/JP2014/002054, filed Apr. 9, 2014. The entire disclosures of these two applications, including their specifications, drawings, and claims, are incorporated herein by reference.

TECHNICAL FIELD

The present disclosure relates to a control method of an information terminal for retrieving a similar medical image which is similar to a medical image of a diagnostic interpretation object and a computer-readable recording medium.

BACKGROUND ART

In recent years, we have seen the development and implementation of medical imaging apparatuses that perform CT (Computed Tomography), MRI (Magnetic Resonance Imaging), and the like. CT, MRI, and the like enable acquisition of digitalized high-resolution medical images in large amounts. In addition, medical images after being diagnostically interpreted by a radiologist are sequentially accumulated in PACS (Picture Archiving and Communication Systems) together with a diagnostic interpretation report. Meanwhile, as disclosed in Patent Literature 1 for example, techniques have started to be developed for retrieving past medical images which are similar to a medical image of a diagnostic interpretation object from past cases accumulated in PACS to be used as a reference when newly performing a diagnostic interpretation.

However, further improvements are required.

CITATION LIST

Patent Literature

Patent Literature 1: Japanese Unexamined Patent Publication No. 2008-257292
Patent Literature 2: Japanese Unexamined Patent Publication No. 2012-35124

Non Patent Literature

Non Patent Literature 1: Akira Oosawa and four others, "Development of "SYNAPSE Case Match", Content-based Image Retrieval System for Supporting Image Diagnosis", Fujifilm Research & Development, FUJIFILM Corporation, Mar. 27, 2013, No. 58, pp. 11-14.

SUMMARY OF INVENTION

In one general aspect, the techniques disclosed here feature a control method of an information terminal, which is connected to a medical information management system that manages medical images that are diagnostic interpretation object candidates, and which is connected to a case retrieval system that refers to a medical image database in which medical images are registered and retrieves a medical image, and moreover which includes a display, one medical image that is a diagnostic interpretation object selected from the diagnostic interpretation object candidates managed by the medical information management system being displayed on the display, the control method causing a computer of the information terminal to:

sense specification information indicating a region of interest in the medical image;

receive from the case retrieval system one or more similar medical images each having a prescribed degree of similarity with a feature quantity of the region of interest indicated by the specification information in accordance with the region of interest;

display the medical image that is managed by the medical information management system in a first display region of a first display screen that is displayed on the display and display thumbnail views of a plurality of similar medical images received from the case retrieval system in a second display region that differs from the first display region of the first display screen, the first display region including a first display box for displaying the medical image and a second display box for displaying a first similar medical image selected from the similar medical images displayed in thumbnail views in the second display region, the first display box and the second display box being adjacent to each other; and when sensing an operation for moving the first similar medical image among the similar medical images displayed in thumbnail views in the second display region to the second display box, display the first similar medical image in the second display box and display the first similar medical image so as to be adjacent to the medical image.

According to the aspect described above, further improvements can be achieved. These general and specific aspects may be implemented using a system, a method, and a computer program, and any combination of systems, methods, and computer programs.

BRIEF DESCRIPTION OF DRAWINGS

FIG. 8 is an enlarged view of a disease name list display region.

FIG. 11 is an enlarged view of a distribution list display region.

FIG. 12 is a diagram showing a distribution list display region in which a check mark is input.

FIG. 13 is a diagram showing a basic screen having been narrowed down by a bronchial lesion distribution.

FIG. 14 is a diagram showing a distribution list display region in which a plurality of check marks are input.

FIG. 17 is a diagram showing an example of history information stored in a history information managing unit.

FIG. 22 is a diagram showing a data configuration of patient information.

FIG. 23 is a diagram showing a data configuration of examination information that is registered in the patient information shown in FIG. 22.

FIG. 25 is a diagram showing a data configuration of a diagnostic report.

FIG. 26 is a diagram showing a data configuration of similar case data.

FIG. 29 is a screen diagram of an examination list.

FIG. 30 is a screen diagram of an examination list after an examination is selected.

FIG. 35 is a diagram showing a data configuration of a disease name list that is generated in S1300 in FIG. 33.

FIG. 36 is a diagram showing a first display example of a disease name list display region.

FIG. 38 is a diagram showing a third display example of a disease name list display region.

FIG. 39 is a diagram showing a screen transition of the disease name list display region shown in FIG. 37.

FIG. 40 is a diagram showing a data configuration of a distribution list that is generated in S1400 in FIG. 33.

FIG. 42 is a diagram showing an example of layout management information.

FIG. 43 is a diagram showing an example of layout management information.

FIG. 44 is a diagram showing a data configuration of display box management information.

FIG. 52 is a diagram showing the one thumbnail image selected in FIG. 51 being dragged.

FIG. 55 is a diagram showing display box management information in which a slice ID of a similar case has been registered.

FIG. 57 is a diagram showing a display relationship between two displays.

FIG. 58 is a diagram showing a display relationship between two displays.

FIG. 59 is a diagram showing a display relationship between two displays.

FIG. 73A is a diagram showing a display example of a second display screen.

Figure 1:
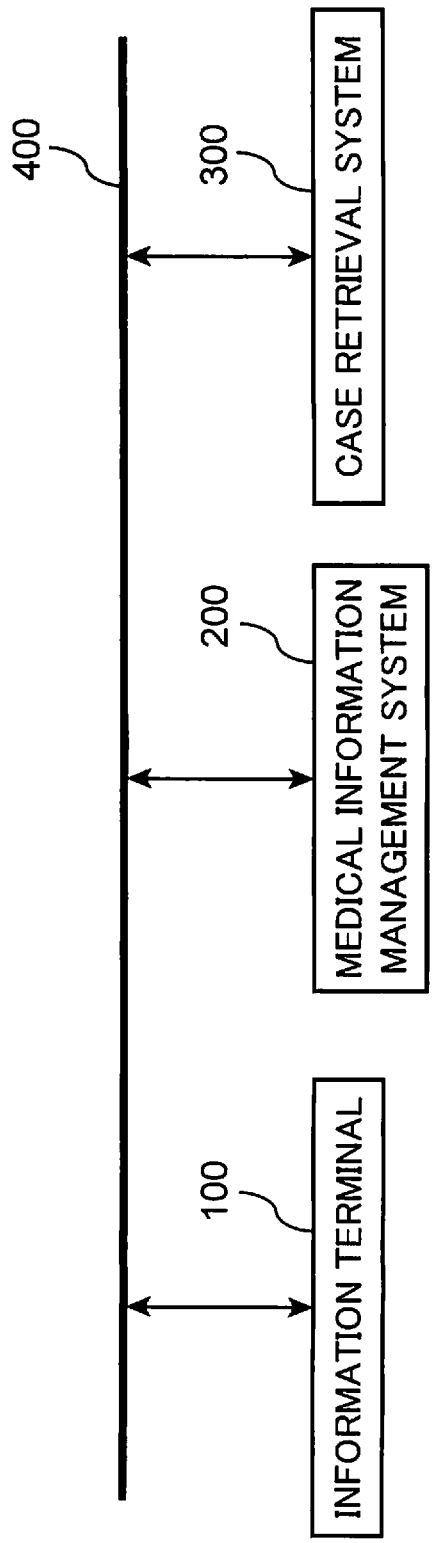
FIG. 1 is an overall configuration diagram of a hospital information system to which an information terminal according to a present embodiment is applied.

DETAILED DESCRIPTION (Circumstances Leading to the Invention of an Aspect of the Present Disclosure)

First, viewpoints of an aspect according to the present disclosure will be described.

Patent Literature 1 discloses an image diagnosis supporting apparatus that presents a case image useful for determining a disorder during image diagnosis based on a diagnosis object image, or statistical information related to the disorder, or the like. A screen of a retrieval result by the image diagnosis supporting apparatus displays a diagnosis object image and information on a representative case for each disorder. Specifically, the screen of the retrieval result displays i) images of representative cases of top three disorders A, D, and G, ii) a degree of similarity with a diagnosis object image, the number of registered cases, and the number of representative cases for each disorder, iii) the number of retrievals (total number of retrieved disorders), and iv) a "next page" software button and the like for referring to information on other disorders that cannot be displayed on one screen (paragraphs [0062] and [0063] and FIG. 6(E)).

In Patent Literature 1, on the screen of the retrieval result, images of representative cases of each disorder are sequentially displayed from a position near to the diagnosis object image to a position distant from the diagnosis object case. Therefore, when comparing the diagnosis object image with an image of a representative case of each disorder, depending on a display position of an image of the representative case that a radiologist wishes to compare (for example, a disorder G in FIG. 6E according to Patent Literature 1), a line-of-sight movement of the radiologist increases because images of other representative case are in-between. In this case, in addition to a physical burden that accompanies the line-of-sight movement, diagnostic accuracy declines as well. When a radiologist compares a diagnosis object image with an image of a representative case, the radiologist performs a detailed comparison on a large number of items such as a position, a size, a shape, and a distribution of a shadow corresponding to a lesion site in the images. Therefore, when a diagnosis object image and an image of a representative case are being displayed separated from each other instead of being displayed adjacent to each other, diagnostic accuracy conceivably declines because it is difficult to perform the detailed comparison described above.

Patent Literature 2 discloses a medical image displaying apparatus that enables comparative diagnostic interpretation to be readily performed on tomographic image data of a plurality of series of a same patient. Specifically, a reference/comparison object image data display screen includes a reference tomographic image data display region, a thumbnail image data display region, and a comparison object image data display region. Reference tomographic image data is displayed in the reference tomographic image data display region. In addition, comparison thumbnail image data is displayed in the thumbnail image data display region. In this state, when comparison thumbnail image data that is displayed in the thumbnail image data display region is dragged and dropped into the comparison object image data display region, comparison tomographic image data corresponding to the comparison thumbnail image data is displayed in the comparison object image data display region (paragraphs [0046] to [0049] and FIG. 7). In this case, comparative diagnostic interpretation refers to comparative diagnostic interpretation using image data obtained by different image diagnostic apparatuses or obtained under different photographic conditions with respect to a same patient or to comparative diagnostic interpretation using past and latest image data obtained by a same image diagnostic apparatus with respect to a same patient.

As described above, since Patent Literature 2 is premised on the comparison between images of a same patient, Patent Literature 2 does not describe comparisons between images of different patients. In images of a same patient, positions and the like of shadows corresponding to lesion sites in the images are more or less the same. Therefore, comparative diagnostic interpretation can be performed more efficiently by performing a detailed comparison using magnified tomographic image data instead of performing a comparison using thumbnail images which are reduced tomographic image data. As a result, Patent Literature 2 does not disclose a theory in which, when comparing medical images, comparison thumbnail image data and reference tomographic image data are displayed adjacent to each other in a thumbnail image stage in order to narrow down the comparison thumbnail image data.

Non Patent Literature 1 discloses a similar case retrieval system in which, due to a function of retrieving a past similar case using a lesion image, appropriate information is instantaneously extracted and presented from clinical knowledge accumulated in PACS described above and the like in order to support image diagnosis of a radiologist. Specifically, the present system retrieves case images with features of lesions similar to an examination image and displays a plurality of case images in an order of similarity. Subsequently, one reference case image is selected among the plurality of displayed case images and is displayed side by side with the examination image ("2.2 Feature of Present System" on page 12 and FIG. 3).

The system disclosed in Non Patent Literature 1 displays the selected reference case image side by side with an examination image. Therefore, Non Patent Literature 1 does not disclose a theory in which, when comparing medical images, the examination image and case images that are retrieval results are displayed adjacent to each other in a thumbnail image stage in order to narrow down the retrieval results.

Based on the considerations described above, the present inventors have arrived at respective aspects of the present disclosure as follows.

An aspect of the present disclosure is a control method of an information terminal, which is connected to a medical information management system that manages medical images that are diagnostic interpretation object candidates, and which is connected to a case retrieval system that refers to a medical image database in which medical images are registered and retrieves a medical image, and moreover which includes a display, one medical image that is a diagnostic interpretation object selected from the diagnostic interpretation object candidates managed by the medical information management system being displayed on the display, the control method causing a computer of the information terminal to:

sense specification information indicating a region of interest in the medical image;

receive from the case retrieval system one or more similar medical images each having a prescribed degree of similarity with a feature quantity of the region of interest indicated by the specification information in accordance with the region of interest;

display the medical image that is managed by the medical information management system in a first display region of a first display screen that is displayed on the display and display thumbnail views of a plurality of similar medical images received from the case retrieval system in a second display region that differs from the first display region of the first display screen, the first display region including a first display box for displaying the medical image and a second display box for displaying a first similar medical image selected from the similar medical images displayed in thumbnail views in the second display region, the first display box and the second display box being adjacent to each other; and when sensing an operation for moving the first similar medical image among the similar medical images displayed in thumbnail views in the second display region to the second display box, display the first similar medical image in the second display box and display the first similar medical image so as to be adjacent to the medical image; wherein when it is sensed that a first similar medical image selected from the plurality of similar medical images included in the second display region is moved to a second display box included in the first display region, a second display screen on which the medical image and the first similar medical image are arranged in contrast with each other is displayed separately from the first display screen.

According to the present aspect, the medical image that is managed by the medical information management system and a plurality of similar medical images received from the case retrieval system are displayed together on the first display screen. In other words, images from different provision sources are displayed integrated on one display screen. Accordingly, even images from different provision sources can be processed by operations performed on a same display screen.

Therefore, a radiologist can perform subsequent processing of medical images of different types that are managed by separate systems as if the medical images are inside a same system.

As a result, for example, even when one system such as the medical information management system and another system that differs from the one system such as the case retrieval system are respectively run, the hassle that is experienced by a radiologist when having to compare different display screens respectively provided by such different systems and make a professional judgment can be resolved and, by extension, an improvement in diagnostic accuracy can be achieved.

In addition, with the present aspect, for example, a radiologist narrows down a similar medical image to be referred to from a plurality of similar medical images displayed in a thumbnail view in the second display region. Subsequently, the similar medical image eventually selected as a reference image can be moved to the first display region in which a medical image that is a diagnostic interpretation object is displayed.

In doing so, according to the present aspect, for example, a first display box for displaying the medical image and a second display box for displaying a first similar medical image selected from the similar medical images displayed in the second display region are arranged in the first display region so as to be adjacent to each other. In other words, in the present aspect, a radiologist is prompted to narrow down a final candidate by a method involving moving the first similar medical image to the second display box that is included in the first display region.

Accordingly, a similar medical image selected as a final candidate and other similar medical images not selected as the final candidate can be displayed separately. Furthermore, the first similar medical image that is selected as the final candidate is included in the first display region which includes a medical image that is the diagnostic interpretation object. In other words, the first similar medical image is displayed separated from other similar medical images not selected as the final candidate in a region that is adjacent to the diagnostic interpretation object.

Therefore, in addition to displaying the medical image that is the diagnostic interpretation object, the first display region displays the first similar medical image selected as the final candidate so as to be adjacent to the medical image and displays the first similar medical image and the medical image as a group.

As a result, in a stage prior to making a detailed judgment or, in other words, in a thumbnail image stage, for example, a radiologist can be asked to make a simple judgment on whether or not a shadow in the first similar medical image is similar to a shadow in a medical image that is the diagnostic interpretation object. In this case, for example, when the medical image that is the diagnostic interpretation object is displayed in the first display region and the first similar medical image is displayed in the second display region, even if the radiologist judges that the shadow in the first similar medical image is similar to the shadow in the medical image that is the diagnostic interpretation object, there may be cases where the radiologist judges that the shadow in the first similar medical image is not similar to the shadow in the medical image that is the diagnostic interpretation object if the medical image that is the diagnostic interpretation object and the first similar medical image are displayed in the first display region.

In other words, in the present aspect, since the medical image that is the diagnostic interpretation object and the first similar medical image are displayed adjacent to each other in the first display region, selection accuracy when the radiologist selects a similar medical image that is a final candidate and therefore must be compared in detail with the medical image that is the diagnostic interpretation object from the similar medical images displayed as a list in the second display region can be improved.

For example, when there is a similar medical image that is closer to the shadow in the medical image that is the diagnostic interpretation object other than the first similar medical image, a judgment can be made to replace the first similar medical image with the other similar medical image in a state prior to making the detailed judgment.

As a result, since selection accuracy of a final candidate in a stage prior to making a detailed judgment (a thumbnail image stage) can be improved, diagnostic accuracy when subsequently making a detailed judgment can also be improved. In addition, since a radiologist can select the similar medical image to be a final candidate in a thumbnail image stage which involves a smaller amount of information than an original image, the trouble of diagnosing a degree of similarity between the medical image that is the diagnostic interpretation object and a similar medical image in detail can be eliminated, and the similar medical image to be a final candidate can be extracted in an efficient manner.

According to the present aspect, a second display screen on which the medical image and the first similar medical image are arranged in contrast with each other starts up due to an operation involving moving the first similar medical image to the second display box. In other words, an instruction to move the first similar medical image to the second display box doubles as an instruction to start up the second display screen, Accordingly, a device operation for displaying the second display screen can be omitted and the number of operations can be reduced. Since such a reduction in the number of operations reduces the trouble experienced by a radiologist or the time required by the radiologist when performing operations, the radiologist can further concentrate on making a professional judgment accordingly. In other words, a flow of judgment and continuity of thought by the radiologist can be prevented from being interrupted by an interposing device operation. As a result, an improvement in diagnostic accuracy can be promoted.

In addition, according to the present aspect, a second display screen for diagnosis is started up separately from the first display screen for operations. Therefore, for example, on the second display screen, by displaying a similar medical image at a resolution of an original image, a radiologist can perform a detailed evaluation using the second display screen in an effective manner.

Furthermore, in the aspect described above, for example, when it is sensed that a second similar medical image among the plurality of similar medical images included in the second display region is moved to the first display region in a state where the first similar medical image is included in the first display region, the first similar medical image displayed on the second display screen may be switched to the second similar medical image.

According to the present aspect, when switching the first similar medical image displayed on the second display screen to the second similar medical image, a step of erasing the first similar medical image that is included in the first display region can be omitted. As a result, since one step involving a mechanical operation can be omitted when a radiologist is making a professional diagnosis, diagnostic accuracy can be improved without interrupting a flow of thought of diagnosis.

In addition, in the aspect described above, for example, the second display box exists in plurality, and when it is sensed that the second similar medical image has been moved to a second display box in which the first similar medical image is displayed so that the second similar medical image overlaps with the second display box, the first similar medical image displayed in the second display box may be switched to the second similar medical image, and when it is sensed that the second similar medical image has been moved to a second display box in which the first similar medical image is not displayed, the second similar medical image may be displayed in the second display box.

In this case, when the first similar medical image is displayed in the second display box but the first similar medical image is judged not to be similar to a medical image that is a diagnostic interpretation object, the first similar medical image may be switched to a second similar medical image by only performing a simple operation of moving a desired second similar medical image from the second display region and causing the second similar medical image to overlap with the first similar medical image. Therefore, a first similar medical image can be switched to a second similar medical image without performing an operation to erase the first similar medical image and work efficiency can be improved.

In addition, if there is a second display box in which the first similar medical image is not displayed in the first display region, by moving the second similar medical image to the second display box, the second similar medical image is displayed in the second display box. Therefore, the second similar medical image can be displayed in the first display region while keeping the first similar medical image displayed in the second display box. As a result, a plurality of similar medical images that are similar to a medical image that is a diagnostic interpretation object can be displayed adjacent to each other in the first display region and a diagnosis on which of the first and second similar medical images is more similar to the medical image that is a diagnostic interpretation object can be readily made.

Furthermore, in the aspect described above, for example, the first display screen may include a third display region that displays a similar medical image previously included in the first display region, the first display region may include a prescribed number of display boxes including the first display box and the second display box, and when the number of similar medical images moved from the second display region to the first display region exceeds the prescribed number, the similar medical image included in the first display region may be moved to the third display region.

According to the present aspect, even if the number of similar medical images moved from the second display region to the first display region exceeds the prescribed number, a similar medical image that has already been moved from the second display region to the first display region is moved to the third display region. In other words, a similar medical image that has already been moved from the second display region to the first display region is displayed in another display region, namely, the third display region, which is included in the first display screen, and remains in the first display screen without being erased from the first display screen.

Therefore, once selected, a similar medical image can be displayed distinguished from other similar medical images which are included in the second display region and which have not been selected even if the selected similar medical image has a lower degree of similarity to a shadow in the medical image that is a diagnostic interpretation object than similar medical images that are included in the first display region.

As a result, by displaying a similar medical image which was once selected but not kept as a final candidate so as to be distinguished from similar medical images not yet selected, the futility of once again selecting a similar medical image that has already been selected and moving the similar medical image to the first display region can be eliminated.

In addition, in the aspect described above, for example, the first display screen may include a third display region that displays a similar medical image previously included or currently included in the first display region, the first display region may include a prescribed number of display boxes including the first display box and the second display box, when the number of similar medical images moved from the second display region to the first display region is equal to or smaller than the prescribed number, the moved similar medical image may be displayed in the first display region and the third display region, and when the number of similar medical images moved from the second display region to the first display region exceeds the prescribed number, the similar medical image included in the first display region may be moved to the third display region.

According to the present aspect, a similar medical image moved from the second display region to the first display region is at least displayed in the third display region. As a result, all selected similar medical images can be displayed so as to be distinguished from similar medical images not yet selected. Therefore, since a radiologist need only check the third display region, the futility of once again selecting a similar medical image that has already been selected and moving the similar medical image to the first display region can be eliminated.

Furthermore, in the aspect described above, for example, a display size of a similar medical image in the third display region may be set smaller than a display size of a similar medical image in the first display region and the second display region.

Since the similar medical images included in the third display region are similar medical images which had been once selected but not kept as a final candidate or are all selected similar medical images, the similar medical images have once been viewed or judged by a radiologist. Therefore, since the similar medical images included in the third display region remain in the memory of the radiologist to a certain degree, even if details of the similar medical images are not displayed as large images, a judgment can be made to a certain degree as to what kind of images the similar medical images are.

On the other hand, a similar medical image not yet selected cannot be appropriately selected in comparison to the medical image that is a diagnostic interpretation object unless displayed as a relatively large image.

According to the aspect described above, a display size of a similar medical image in the third display region is set smaller than a display size of a similar medical image in the first display region and the second display region. Accordingly, even when the third display region is included in the first display screen which is limited in terms of display regions, the first display screen is effectively utilized. Therefore, the first display screen can be effectively utilized by displaying similar medical images which had been once selected but not kept as a final candidate and similar medical images not yet selected so as to be distinguished from one another, comparing the similar medical images with the medical image that is a diagnostic interpretation object, and appropriately selecting a similar medical image that is similar to the medical image that is a diagnostic interpretation object.

In addition, in the aspect described above, for example, a display arrangement of the second display screen may be the same as a display arrangement of a first display region that is included in the first display screen.

According to the present aspect, even if the first display screen that is a display screen for performing operations and the second display screen that is a display screen for performing diagnosis are provided separately, by keeping in mind a layout of a medical image arranged in the first display region that is included in the first display screen by an operation on the first display screen, a diagnosis can be made using the second display screen with the same arrangement.

Figure 73B:
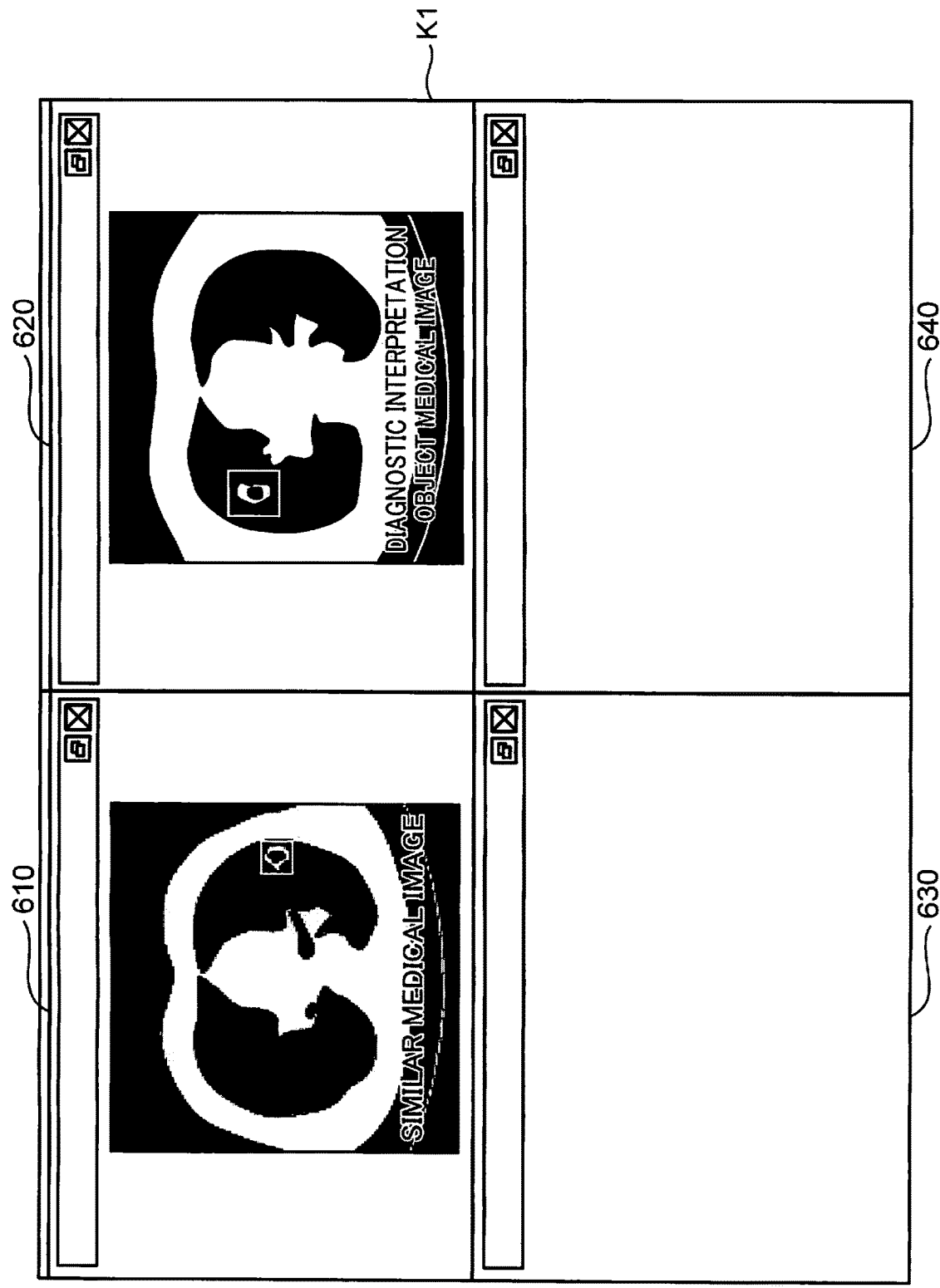
FIG. 73B is a diagram showing a display example of a second display screen.

In addition, positions of shadows corresponding to lesion sites which are included in similar medical images vary. Therefore, depending on a position of a shadow included in a similar medical image, a line-of-sight movement may increase when comparing the shadows with a shadow included in a medical image that is a diagnostic interpretation object. Specifically, as shown in FIG. 73A, when a shadow included in a medical image that is a diagnostic interpretation object exists on a left side of a right lung as seen on the screen and a shadow included in a similar medical image exists on a right side of a left lung as seen on the screen, a line-of-sight movement of a radiologist increases if the medical image that is a diagnostic interpretation object is arranged to the left of the similar medical image on the second display screen. In such a case, as shown in FIG. 73B, by arranging the medical image that is a diagnostic interpretation object to the right of the similar medical image on the second display screen, the line-of-sight movement of the radiologist can be reduced significantly. As a result, in addition to reducing a physical burden on the radiologist due to the line-of-sight movement, diagnostic accuracy can be improved. As described above, there is a need by radiologists to arbitrarily set display positions of a medical image that is a diagnostic interpretation object and a similar medical image. According to the present aspect, since a radiologist can arbitrarily set a display arrangement of the first display region that is included in the first display screen, a display arrangement that satisfies the need of the radiologist can be realized on the second display screen used for detailed comparative display.

Furthermore, in the aspect described above, for example, the display may include a first display and a second display, and the first display screen may be displayed on the first display and the second display screen may be displayed on the second display.

A large number of images are respectively displayed on the first display screen and the second display screen. In addition, the displayed images respectively include shadows corresponding to similar lesion sites. Therefore, when a radiologist continues a diagnostic interpretation operation over an extended period of time, confusion may occur when viewing the respective display screens as to whether a display screen is the first display screen to be used to select a similar medical image or the second display screen to be used to compare a medical image that is a diagnostic interpretation object with the selected similar medical image in detail.

According to the present aspect, the first display is used as a display for selecting a similar medical image to be comparatively displayed with a medical image that is a diagnostic interpretation object and the second display is used as a display for comparing the medical image that is a diagnostic interpretation object with the selected similar medical image in detail. As a result, when a radiologist views the respective displays, the radiologist can be made conscious of whether to select a similar medical image or to compare a medical image with a selected similar medical image in detail and the confusion described above can be prevented.

In addition, in the aspect described above, for example, disease name information on a lesion represented in a medical image that is a diagnostic interpretation object may not be set in additional information of the medical image, and disease name information on a lesion represented in each of the plurality of received similar medical images may be set in additional information of each of the plurality of received similar medical images.

According to the present aspect, when observing the medical image that is a diagnostic interpretation object in order to identify a disease name of a lesion appearing on the medical image that is a diagnostic interpretation object, diagnostic accuracy can be improved by referring to a similar medical image representing a lesion whose disease name has already been identified.

Furthermore, in the aspect described above, for example, the second display region may include a prescribed number of display frames, and images of the prescribed number or less among the plurality of received similar medical images may be displayed in each of the display frames in a descending order of degrees of similarity with the medical image that is a diagnostic interpretation object.

According to the present aspect, by displaying the plurality of received similar medical images in a descending order of degrees of similarity with the medical image that is a diagnostic interpretation object when comparing the medical image that is a diagnostic interpretation object with the similar medical images in a contrasting manner, the similar medical images are to be compared with the medical image that is a diagnostic interpretation object in a descending order of degrees of similarity. Therefore, for example, diagnostic accuracy can be improved by having a disease name of a lesion appearing in the medical image that is a diagnostic interpretation object identified in an efficient manner.

In addition, in the aspect described above, for example, the control method may cause the computer of the information terminal to:

transmit information indicating the feature quantity of the region of interest to the case retrieval system; and receive the similar medical image having the prescribed degree of similarity with the feature quantity of the region of interest from the case retrieval system.

In addition, in the aspect described above, for example, the control method may cause the computer of the information terminal to:

transmit the one medical image that is a diagnostic interpretation object and specification information indicating the region of interest to the case retrieval system; and receive, from the case retrieval system, the similar medical image having the prescribed degree of similarity with the feature quantity of the region of interest obtained from the medical image that is a diagnostic interpretation object and the specification information.

In addition, in the aspect described above, for example, the one medical image that is a diagnostic interpretation object may be a medical image of a lung, the similar medical image may be a medical image of a lung, the first display screen may include first distribution information for selecting a similar medical image in which a size of a region corresponding to the region of interest belongs to a prescribed first range, the first range indicating that the size of the region corresponding to the region of interest is wider than a prescribed range in a region of the lung, second distribution information for selecting a similar medical image in which the size of the region corresponding to the region of interest belongs to a prescribed second range, the second range being lower than the first range and indicating that the size of the region corresponding to the region of interest is a part of a region of the lung, and third distribution information for selecting a similar medical image in which the region corresponding to the region of interest includes a pleura, and when any one of the first to third items of distribution information is selected, a similar medical image corresponding to the selected distribution information may be displayed in the second display region.

According to the present aspect, a plurality of similar medical images displayed in the second display region may be further sorted based on a distribution type of a lesion region that exists in addition to the region of interest. Accordingly, for example, a similar medical image with a distribution of a lesion region that is similar to a distribution type of a lesion region that exists in the medical image that is a diagnostic interpretation object in addition to the region of interest can be efficiently selected from a large number of displayed similar medical images.

In addition, in the aspect described above, for example, when selection of the first distribution information is sensed, a similar medical image corresponding to the first distribution information may be displayed in a corresponding display region at an initial display size, when selection of the second distribution information is sensed, a similar medical image corresponding to the second distribution information may be magnified and displayed in a corresponding display region so as to be centered on the region corresponding to the region of interest in the similar medical image corresponding to the second distribution information, and when selection of the third distribution information is sensed, a similar medical image corresponding to the third distribution information may be magnified and displayed in a corresponding display region in a state where the pleura is included so as to be centered on the region corresponding to the region of interest in the similar medical image corresponding to the third distribution information.

According to the present aspect, when sorting similar medical images based on a distribution type of a region corresponding to the region of interest, the similar medical images are not only sorted but also displayed in accordance with the distribution type. Accordingly, after sorting similar medical images based on a distribution type of a region corresponding to the region of interest, the operator is not required to separately perform a process for magnifying a similar medical image in accordance with the distribution type, centering the similar medical image on a region corresponding to the region of interest, or the like. Therefore, even when a large number of similar medical images are sorted based on a distribution type of a region corresponding to the region of interest, the hassle of repetitively performing a similar operation on each of the large number of sorted similar medical images can be significantly reduced. As a result, interruptions of the thought or concentration of a radiologist that is best focused on making a medical judgment by the hassle of performing operations can be significantly reduced and the thought or concentration of the radiologist can be directed towards making a medical judgment as it should be. Thus, accuracy of medical judgment can be improved.

In addition, in the aspect described above, for example, the first distribution information may be information indicating a distribution belonging to a bilateral, a multiple, a diffuse, or a hematogenous category, the second distribution information may be information indicating a distribution belonging to a segmental or a bronchial category, and the third distribution information may be information indicating a distribution belonging to a subpleural category.

According to the present aspect, in a case of a distribution belonging to a bilateral, a multiple, a diffuse, or a hematogenous category, a similar medical image is displayed in an initial display size, in a case of a distribution belonging to a segmental or a bronchial category, a similar medical image is magnified and displayed, and in a case of a distribution belonging to a subpleural category, a similar medical image is magnified and displayed in a state where the pleura is included.

In a case of a distribution belonging to a bilateral, a multiple, a diffuse, or a hematogenous category, it is likely that a lesion site has spread throughout a lung or that a lesion site has occurred in a wide area of a lung. Therefore, there is a need from a medical perspective to display a similar medical image in an initial display size or, in other words, without magnification. On the other hand, in a case of a distribution belonging to a segmental or a bronchial category, such likelihood is low. Therefore, by magnifying and displaying a similar medical image when a distribution belonging to a segmental or a bronchial category is selected, a step of magnifying and displaying an image can be omitted and the concentration of a radiologist can be prevented from being interrupted. In addition, in a case of a distribution belonging to a subpleural category, a positional relationship between the pleura and the lesion site is an important indicator for diagnosis. Therefore, there is a need from a medical perspective to magnify to display a similar medical image in a state where the pleura is included.

Embodiment

Hereinafter, an embodiment of the present disclosure will be described with reference to the drawings. Moreover, in the respective drawings, like symbols are used for like components.

FIG. 1 is an overall configuration diagram of a hospital information system to which an information terminal according to a present embodiment is applied. As shown in FIG. 1, the hospital information system includes an information terminal 100, a medical information management system 200, and a case retrieval system 300.

The information terminal 100, the medical information management system 200, and the case retrieval system 300 are connected so as to be capable of communicating with each other via a network 400.

The medical information management system 200 and the case retrieval system 300 need not necessarily be arranged inside a hospital and may be software that runs at a data center or on a private cloud server, a public cloud server or the like outside of the hospital. When the medical information management system 200 and the case retrieval system 300 are installed inside a hospital, a local area network may be adopted as the network 400. As the local area network, an IEEE 802.3 series wired LAN, an IEEE 802.11 series wireless LAN, or a network that combines the two can be adopted. When the medical information management system 200 and the case retrieval system 300 are realized using servers outside a hospital, the Internet may be adopted as the network 400.

As the information terminal 100, an information terminal such as a personal computer or a tablet terminal is adopted. As the medical information management system 200, PACS (Picture Archiving and Communication Systems), an electronic medical chart system, or the like is adopted.

Figure 2:
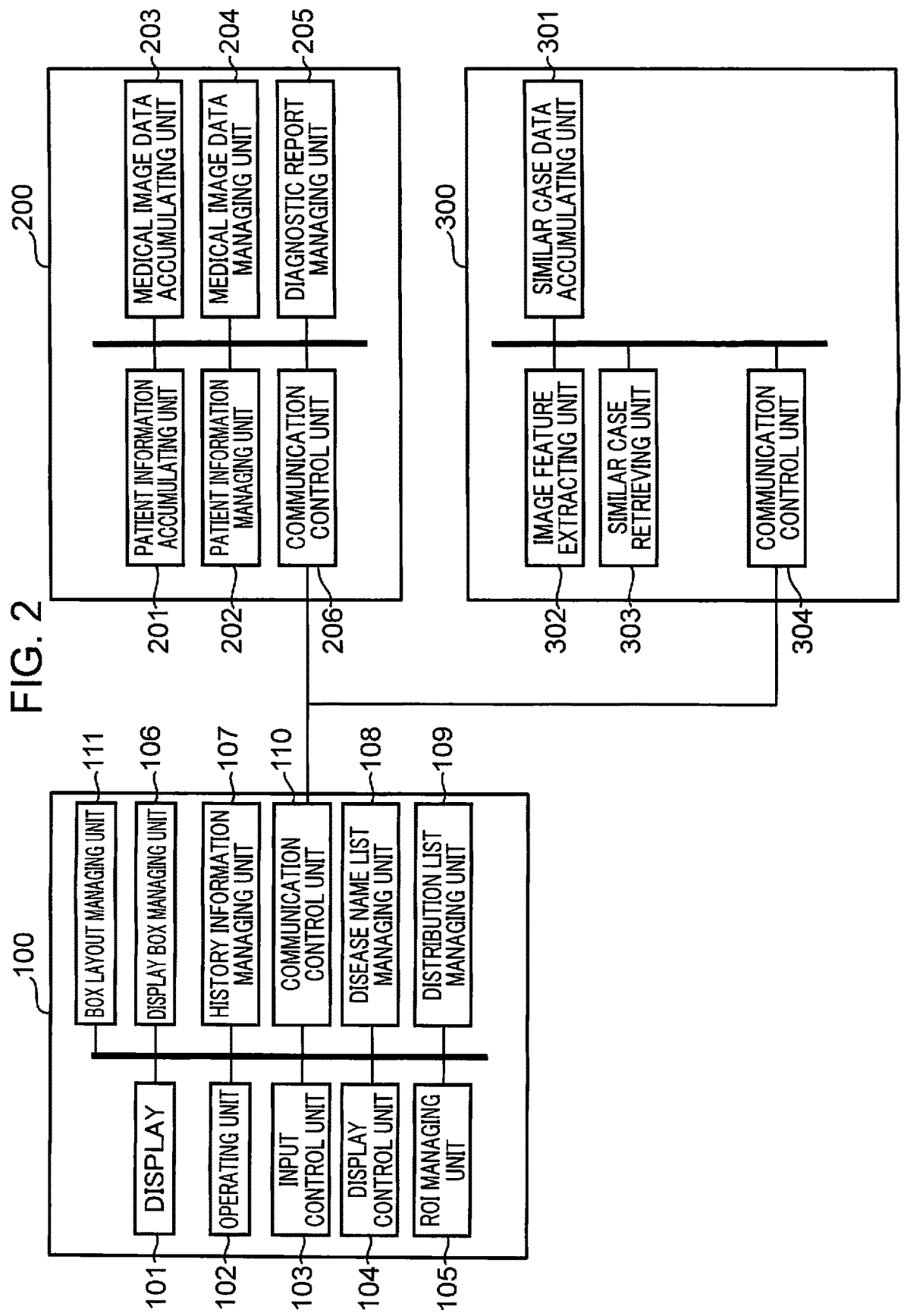
FIG. 2 is a block diagram showing configurations of an information terminal, a medical information management system, and a case retrieval system.

FIG. 2 is a block diagram showing configurations of the information terminal 100, the medical information management system 200, and the case retrieval system 300. As shown in FIG. 2, the information terminal 100 includes a display 101, an operating unit 102, an input control unit 103, a display control unit 104, an ROI managing unit 105, a display box managing unit 106, a history information managing unit 107, a disease name list managing unit 108, a distribution list managing unit 109, a communication control unit 110, and a box layout managing unit 111.

The display 101 is constituted by a liquid crystal monitor for example, displays a medical image and a medical chart image to be diagnosis objects and, at the same time, displays a report input image for entering a diagnosis result and the like. While at least one display 101 is required, normally, two to three displays 101 are used to perform image diagnosis. In the present embodiment, two displays 101 are used. One of the displays 101 will be referred to as a display 101a (an example of the second display) and the other display 101 will be referred to as a display 101b (an example of the first display) (refer to FIG. 3).

Figure 3:
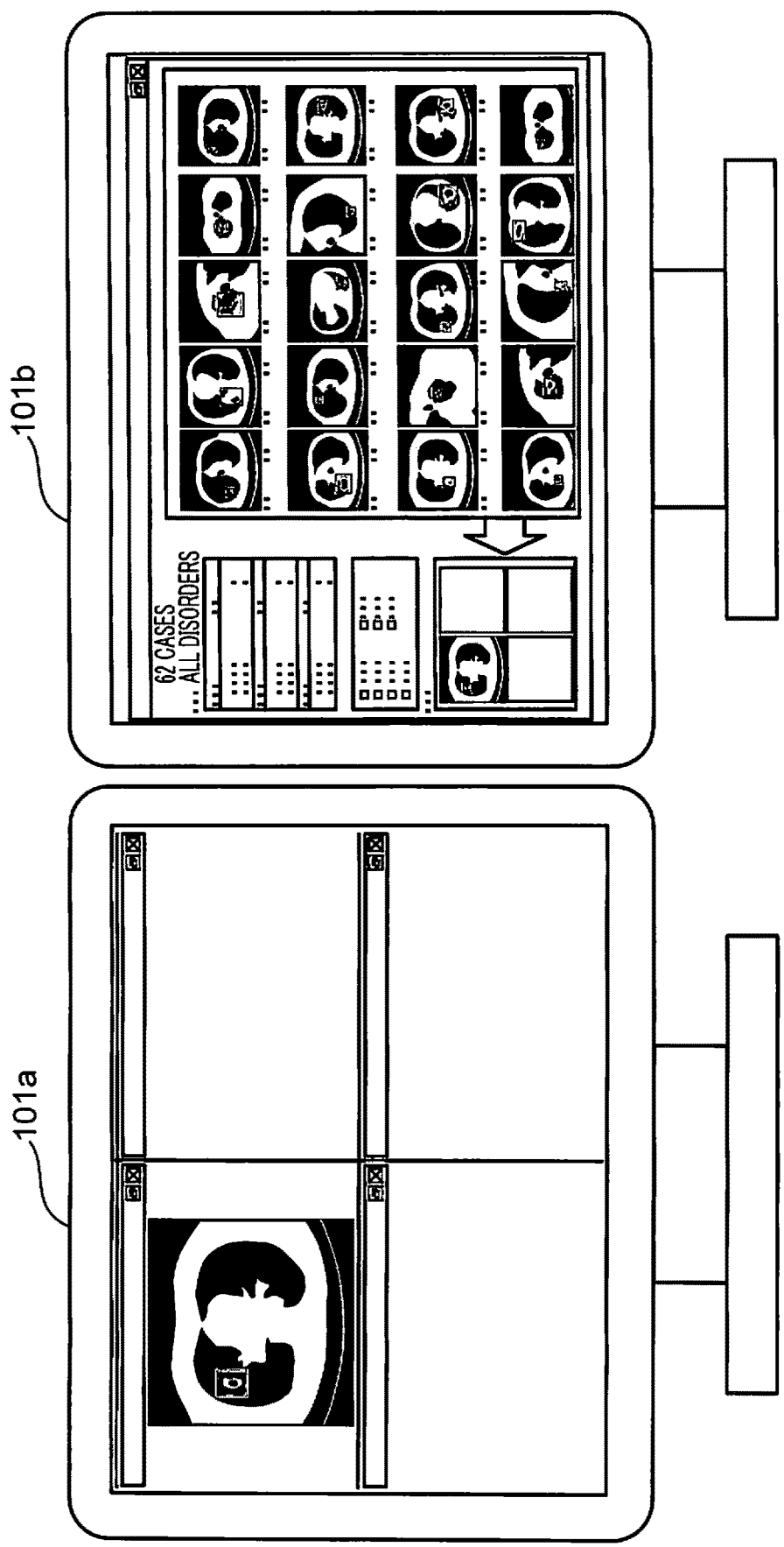
FIG. 3 is an external view of two displays.

In addition, a display screen of the display 101a is an example of the second display screen and a display screen of the display 101b is an example of the first display screen. FIG. 3 is an external view of the two displays 101a and 101b. In FIG. 3, four medical image viewers are displayed in a two-row, two-column arrangement on the display 101a and a screen of the case retrieval system 300 is displayed on the display 101b. Moreover, when only one display 101 is provided, the first display screen and the second display screen are displayed by dividing regions on the display screen of the one display 101.

The operating unit 102 includes, for example, a keyboard and a mouse and accepts various operations input by a user to the information terminal 100. For example, the operating unit 102 accepts operations by the user on a medical image and a medical chart image displayed on the display 101, operations for inputting a diagnosis result to a report input screen, and the like.

Upon sensing an operation by the user on the operating unit 102, the input control unit 103 interprets a content of the operation and notifies the operation content to other components. For example, the input control unit 103 senses a position of a mouse pointer on the display 101 from coordinate data output by a mouse as the operating unit 102 and causes the mouse pointer to be displayed on the display 101. In addition, if a GUI part (for example, a GUI button) generated by the display control unit 104 is displayed at a display position of the mouse pointer upon sensing that the mouse has been clicked, the input control unit 103 determines that the GUI has been selected by the user and notifies other components that the GUI has been selected by the user.

The display control unit 104 generates a GUI (Graphical User Interface) of the information terminal 100 and causes the GUI to be displayed on the display 101.

When performing a similar case retrieval, the ROI managing unit 105 generates region of interest information indicating a region of interest that is set with respect to a retrieval query image (to be described later) and stores the region of interest information in a memory, and manages the region of interest information.

The display box managing unit 106 stores display box management information 4410 (FIG. 44) to be described later in a memory and manages the display box management information 4410.

The history information managing unit 107 generates history information 1701 in which is registered a similar case ID of a similar case displayed in a history management region 760 (FIG. 18) to be described later and stores the history information 1701 in a memory, and manages the history information 1701 (FIG. 17).

The disease name list managing unit 108 generates a disease name list (FIG. 35) of similar cases displayed in a case display region 710 (FIG. 6) and stores the disease name list in a memory, and manages the disease name list.

The distribution list managing unit 109 generates a distribution list (FIG. 40) representing a lesion distribution of similar cases displayed in the case display region 710 and stores the distribution list in a memory, and manages the distribution list.

The communication control unit 110 includes, for example, a communication apparatus for connecting the information terminal 100 to the network 400 and controls communication between the information terminal 100 and the medical information management system 200 and communication between the information terminal 100 and the case retrieval system 300. In addition, the communication control unit 110 accepts transmission requests of various types of data from other blocks and transmits the data to the medical information management system 200 or the case retrieval system 300, and receives data transmitted from the medical information management system 200 or the case retrieval system 300 and hands over the data to a corresponding block.

The box layout managing unit 111 generates layout management information 4200 (FIG. 42) to be described later and stores the layout management information 4200 in a memory, and manages the layout management information 4200.

As shown in FIG. 2, the medical information management system 200 includes a patient information accumulating unit 201, a patient information managing unit 202, a medical image data accumulating unit 203, a medical image data managing unit 204, a diagnostic report managing unit 205, and a communication control unit 206.

The patient information accumulating unit 201 accumulates patient information 1000 (FIG. 22) in which personal information of a patient such as gender and age, clinical information of the patient such as medical history, and examination information of the patient such as a blood test are registered.

With respect to the patient information 1000 (FIG. 22) accumulated in the patient information accumulating unit 201, the patient information managing unit 202 executes a process for registering data input by the user and updating the patient information 1000, a process for outputting the patient information 1000 to the display control unit 104, and the like, and manages the patient information 1000. The medical image data accumulating unit 203 accumulates medical image data that represents examination images of a patient.

The medical image data managing unit 204 accumulates medical image data in the medical image data accumulating unit 203 and manages the medical image data.

The diagnostic report managing unit 205 manages a diagnostic report 3000 (FIG. 25) that represents a diagnosis result by a radiologist with respect to respective examinations performed on a patient.

The communication control unit 206 includes, for example, a communication apparatus for connecting the medical information management system 200 to the network 400, accepts transmission requests of various types of data from other blocks and transmits the data to the information terminal 100 or the case retrieval system 300, and receives data transmitted from the information terminal 100 or the case retrieval system 300 and hands over the data to a corresponding block.

As shown in FIG. 2, the case retrieval system 300 includes a similar case data accumulating unit 301, an image feature extracting unit 302, a similar case retrieving unit 303, and a communication control unit 304.

The similar case data accumulating unit 301 accumulates, in advance, similar case data 4000 (FIG. 26) in which image features extracted from a large number of similar cases selected as object data of similar case retrieval among similar cases managed by the medical information management system 200, thumbnail images generated from the large number of similar cases, and the like are registered.

The image feature extracting unit 302 extracts an image feature in region of interest information of a retrieval query image transmitted from the communication control unit 110 of the information terminal 100. In this case, the region of interest information is an example of the specification information indicating the region of interest.

The similar case retrieving unit 303 generates a similar case retrieval result by respectively comparing the image feature extracted by the image feature extracting unit 302 and image features of one or more similar cases accumulated in the similar case data accumulating unit 301.

The communication control unit 304 includes, for example, a communication apparatus for connecting the case retrieval system 300 to the network 400, accepts transmission requests of various types of data from other blocks and transmits the data to the information terminal 100 or the medical information management system 200, and receives data transmitted from the information terminal 100 or the medical information management system 200 and hands over the data to a corresponding block.

Figure 4:
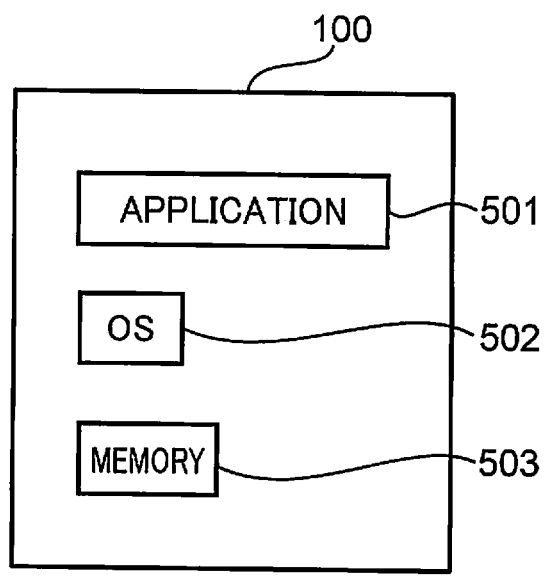
FIG. 4 is a diagram showing a configuration example of an implementation of an information terminal.

FIG. 4 is a diagram showing a configuration example of an implementation of the information terminal 100. As shown in FIG. 4, the information terminal 100 includes an application 501, an OS (Operating System) 502, a memory 503, and other hardware not shown.

The application 501 is application software for causing a personal computer or a tablet terminal to function as the information terminal 100 and is executed by a processor of the information terminal 100. The information terminal 100 may implement the application 501 by reading the application 501 from a computer-readable recording medium or may implement the application 501 by downloading the application 501 from a network.

In this case, the application 501 includes a medical information management application and a similar case retrieval application. The medical information management application is an application for causing the information terminal 100 to work in cooperation with the medical information management system 200 and the similar case retrieval application is an application for causing the information terminal 100 to work in cooperation with the case retrieval system 300. In addition, both applications transmit and receive data to and from each other and integrate services provided by the medical information management system 200 and the case retrieval system 300 in the information terminal 100.

The OS 502 is basic software of the information terminal 100 and is executed by a processor of the information terminal 100. The memory 503 is constituted by a storage apparatus such as a RAM or a ROM included in the information terminal 100 and stores a group of data included in the application 501.

As the processor of the information terminal 100 executes the application 501, functions of the input control unit 103, the display control unit 104, the ROI managing unit 105, the display box managing unit 106, the history information managing unit 107, the disease name list managing unit 108, the distribution list managing unit 109, the communication control unit 110, and the box layout managing unit 111, which are shown in FIG. 2, are realized.

However, in the present embodiment, the information terminal 100 may be only mounted with the application 501, mounted with the application 501 and the OS 502, mounted with the application 501, the OS 502, and the memory 503, or mounted with the application 501, the OS 502, the memory 503, and other hardware not illustrated. The information terminal 100 according to the present embodiment can be realized by any of the implementations.

Figure 5:
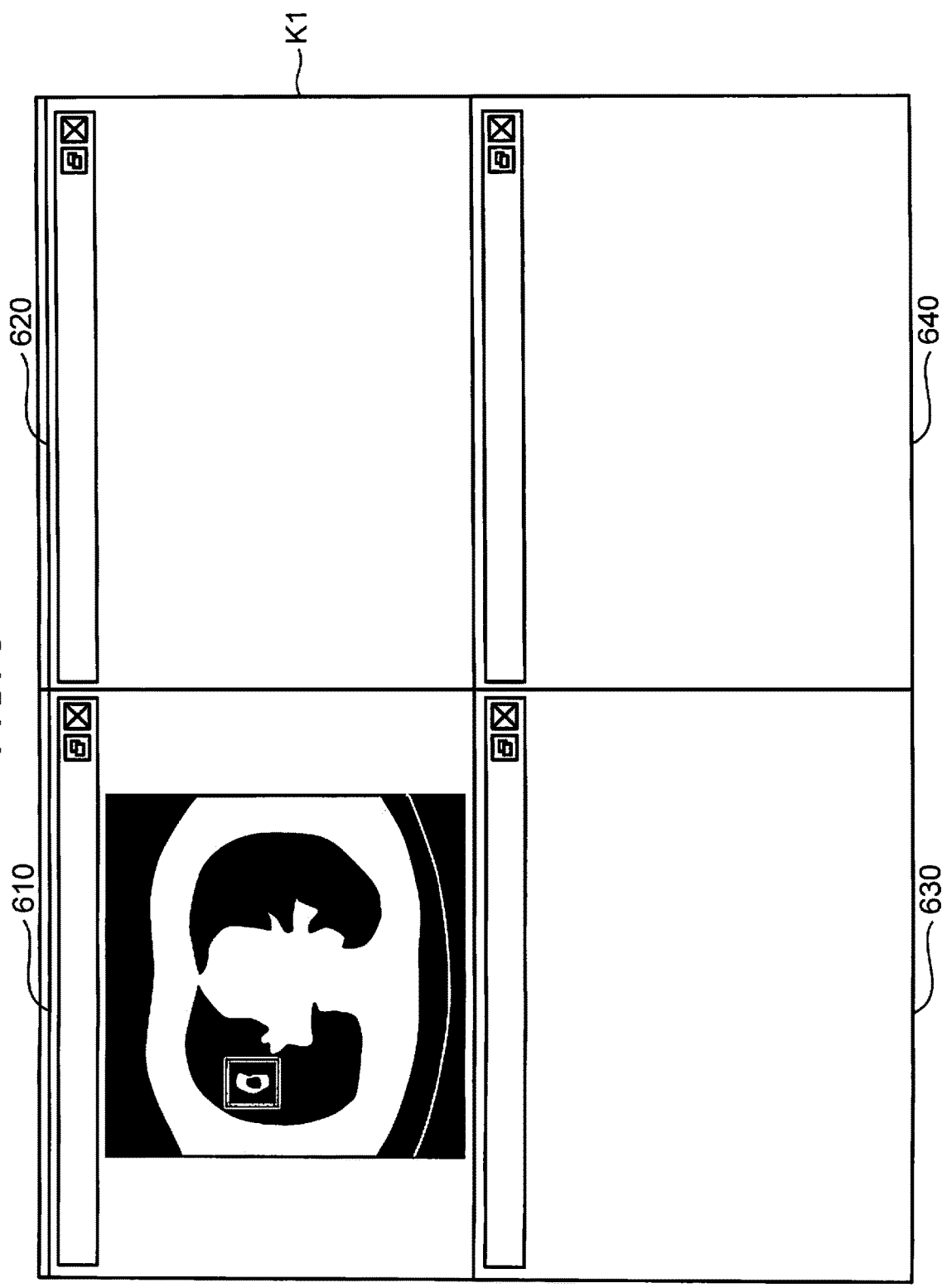
FIG. 5 is a diagram showing an example of a basic screen that is displayed on a display immediately after starting a similar case retrieval application on an information terminal.

FIG. 5 is a diagram showing an example of a basic screen K1 that is displayed on a display 101*a* immediately after starting the similar case retrieval application on the information terminal 100. The basic screen K1 shown in FIG. 5 is constituted by four medical image viewers 610 to 640. A medical image is normally recorded in a DICOM (Digital Imaging and Communication in Medicine) format and the medical image viewers 610 to 640 are viewers capable of handling DICOM. A medical image handled in the present embodiment is assumed to be a chest CT image that is constituted by a large number of tomographic images (hereinafter, referred to as slice images) in the DICOM format. However, this is simply an example and CT images of another site (for example, the head, the abdomen, a leg, and an arm) may be adopted instead.

In a chest CT image displayed on the medical image viewers 610 to 640, slice images are switched by an operation of a mouse or a keyboard. In this case, the slice images constituting a chest CT image are arranged in an order from, for example, the neck toward the abdomen.

For example, when a mouse pointer is positioned on the medical image viewer 610 and a rotation of a mouse wheel is sensed by the input control unit 103, the display control unit 104 switches a slice image that is displayed on the medical image viewer 610 in accordance with an amount of the sensed rotation. For example, when the mouse wheel is rotated by one click toward the rear of the mouse on the medical image viewer 610, the display control unit 104 switches a slice image being displayed to a slice image at a next slice position. On the other hand, for example, when the mouse wheel is rotated by one click toward the front of the mouse on the medical image viewer 610, the display control unit 104 switches a slice image being displayed to a slice image at an immediately previous slice position. Therefore, a user such as a radiologist switches slice images displayed on the medical image viewer 610 as appropriate by rotating the mouse wheel forward or backward to retrieve a desired slice image.

Moreover, as the medical image, an MRI (Magnetic Resonance Imaging) image or a plain radiographic image may be adopted instead of a chest CT image. In addition, while the number of medical image viewers is set to four in the example shown in FIG. 5, this is simply an example and another number such as six and eight may be adopted instead. While an increase in the number of medical image viewers increases the number of images that can be simultaneously compared, a display area per image decreases. Therefore, for the number of medical image viewers, a configuration that can be appropriately modified in accordance with a display size of the display 101*a* may be adopted. In this case, it is assumed that the number of medical image viewers can be changed at will by a user or an administrator.

Before the similar case retrieval application is started, a slice image of a chest CT image of a patient is displayed across an entire region of the display 101*a*. In addition, in this state, as the similar case retrieval application is started by a user such as diagnostic interpreter, the slice image that had been displayed across the entire region of the display 101*a* is displayed on the medical image viewer 610.

In other words, when the user starts the similar case retrieval application, a retrieval query image that had been displayed across the entire region of the display 101*a* is initially displayed on the medical image viewer 610. Moreover, the display control unit 104 may display a region of interest (ROI) that is an object of similar case retrieval so as to overlap with the retrieval query image. A retrieval query image is an example of the medical image that is the diagnostic interpretation object.

In FIG. 5, while no images are displayed on the other medical image viewers 620 to 640, when there are a plurality of examination images of a patient that are diagnosis objects and a plurality of examination images are displayed on the display 101*a* before the similar case retrieval application is started, the display control unit 104 may display the plurality of examination images without modification on the medical image viewers 620 to 640.

Figure 6:
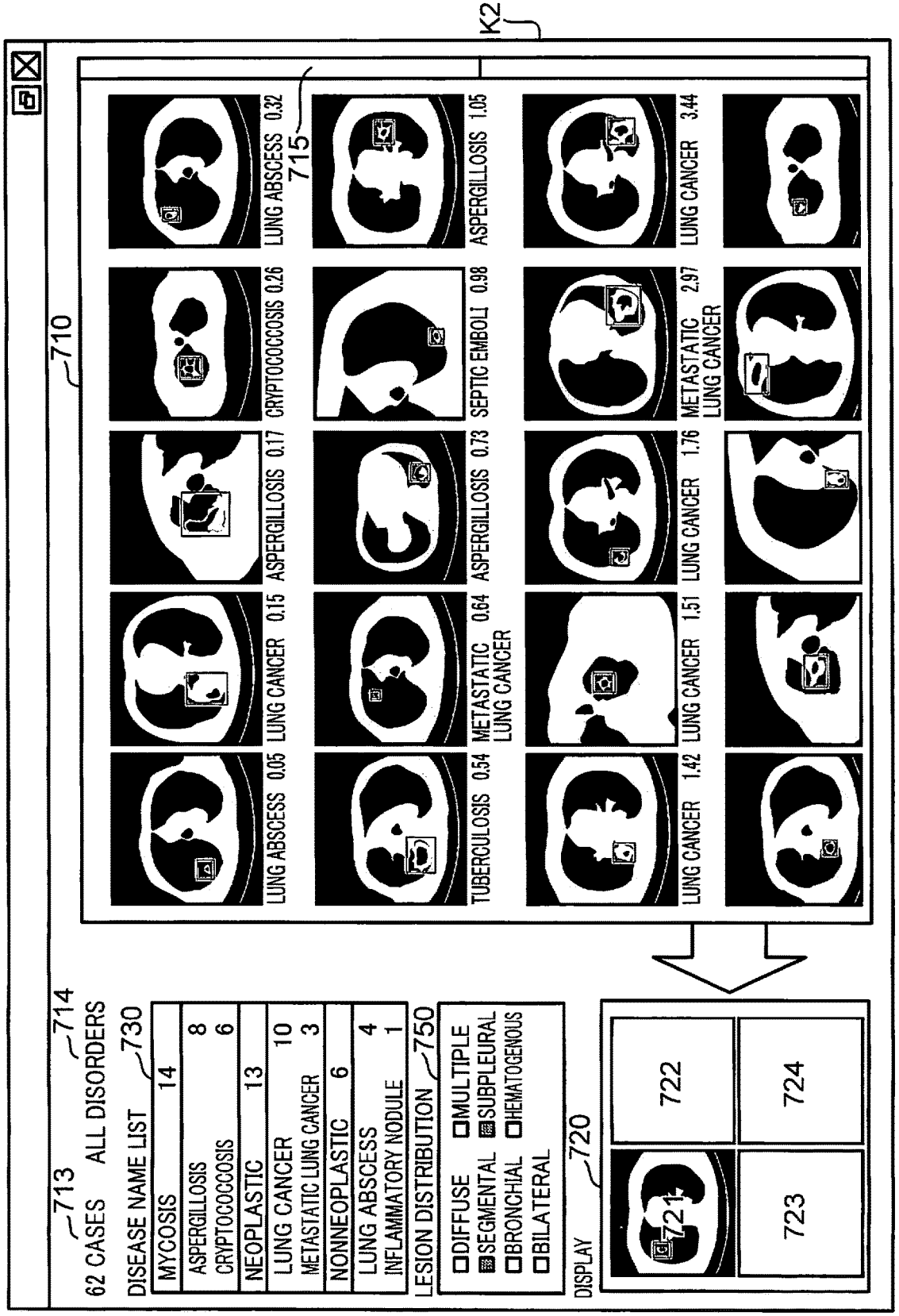
FIG. 6 is a diagram showing an example of a basic screen that is displayed on a display immediately after starting a similar case retrieval application on an information terminal.

FIG. 6 is a diagram showing an example of a basic screen K2 that is displayed on a display 101*b* immediately after starting the similar case retrieval application on the information terminal 100. The basic screen K2 shown in FIG. 6 includes a case display region 710, a layout region 720, a disease name list display region 730, and a distribution list display region 750. Moreover, the layout region 720 is an example of the first display region and the case display region 710 is an example of the second display region.

The case display region 710 is a region for displaying thumbnail images of similar cases that are similar to the retrieval query image in an order of degrees of similarity. In this case, the thumbnail image of the similar case is an example of the similar medical image.

Since a large number of similar cases are displayed in the case display region 710, performing a conversion of resolution or a pixel value in the case display region 710 results in an extended processing time. Therefore, thumbnail images are created in advance from original slice images and saved in the case retrieval system 300.

Hereinafter, additional explanation of a conversion of resolution or a pixel value will be provided. While the resolution of an original slice image is 512×512 pixels, since the resolution of a thumbnail image is much lower, resolution conversion must be performed. In consideration thereof, a thumbnail image is generated by performing a low resolution process and a gradation conversion process on an original slice image.

For example, a gradation conversion process is performed as follows. In a slice image acquired by CT, each pixel value (CT value) takes a value of 2000 grayscale ranging from −1000 to +1000 (in HU: Hounsfield Units) and cannot be displayed as-is on an ordinary 8-bit grayscale display. In addition, even if the image can be displayed, it is difficult for a person to distinguish a pulmonary emphysema region (CT value: −1000 HU), a normal lung field tissue (CT value: about −900 HU), a ground-glass region (CT value: −800 HU), a soft tissue (CT value: −100 to −50 HU), water (CT value: 0 HU), and bone (CT value: 1000 HU) among 2000 grayscale with the naked eye.

Therefore, normally, with a slice image, a window level and a window width are set with respect to each pixel value, the pixel value is reconstructed into an 8-bit pixel value, and the slice image is displayed on the display. In this case, a window level represents a CT value at a center of a window and a window width represents a vertical width of the center of the window.

For example, when a DICOM image is reconstructed in a lung window setting, the window level is set to −550 to −800 and the window width is set to 1000 to 1600. Therefore, a thumbnail image is also generated by reducing a pixel value to 8 bits from an original slice image with the process described above.

Moreover, the thumbnail image displayed in the case display region 710 is a thumbnail image representing a similar case whose distance from a feature vector of a diagnosis object case is equal to or less than a predetermined threshold. In this case, for example, a Euclidean distance is used as the distance. Alternatively, a different distance scale such as a city block distance may be adopted as the distance. The closer the distance between two comparison object images, the more similar. In addition, as the feature vector, a feature vector obtained not from a thumbnail image but from a slice image that is an original image is adopted.

Figure 7:
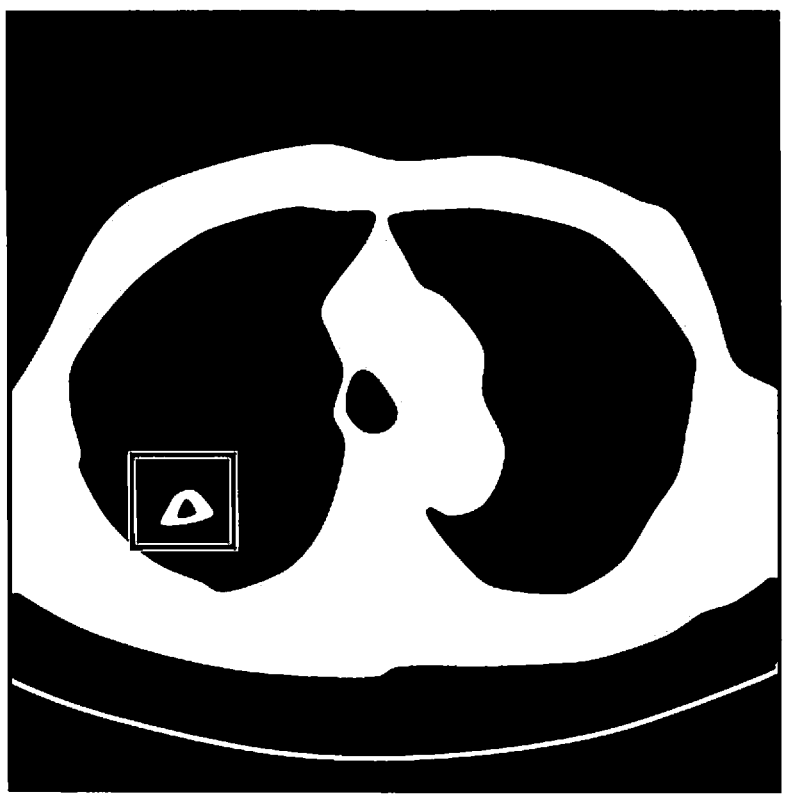
FIG. 7 is an extracted view showing a display region of one similar case that is displayed in a case display region.

FIG. 7 is an extracted view showing a display region of one similar case that is displayed in the case display region 710. A thumbnail image is displayed in the display region of the similar case and a definitively diagnosed disease name display region 711 and a distance display region 712 are arranged below the thumbnail image. A definitively diagnosed disease name of a similar case that is an object is displayed in the definitively diagnosed disease name display region 711. A definitively diagnosed disease name refers to a disease name representing a finalized diagnosis of a similar case that is an object. The distance display region 712 displays a distance between a feature vector of a slice image of a similar case that is an object and a feature vector of a retrieval query image. In the example shown in FIG. 7, since "nontuberculous mycobacteria" is displayed in the definitively diagnosed disease name display region 711, the thumbnail image is a thumbnail image of a similar case that has been definitively diagnosed as "nontuberculous mycobacteria". In addition, since "0.05" is displayed in the distance display region 712, it is shown that a distance between the slice image of the similar case and the retrieval query image is "0.05".

Returning now to FIG. 6, a number of retrieved results display region 713 is arranged in, for example, a top left part of the basic screen K2. The number of retrieved results display region 713 displays the number of similar cases which are similar to the diagnosis object case as acquired from the case retrieval system 300 as a result of a retrieving process.

Moreover, when the number of similar cases is significantly large, the case display region 710 cannot display all similar cases at the same time. In consideration thereof, a scroll bar 715 that is elongated in a vertical direction is provided on the right side of the case display region 710, for example. The display control unit 104 displays a thumbnail image displayed in the case display region 710 by scrolling the thumbnail image in a vertical direction in accordance with an amount of movement of the scroll bar 715. Accordingly, the user can display a similar case previously in a non-displayed state in the case display region 710 and observe the similar case.

Moreover, the scroll bar 715 may be elongated in a horizontal direction. In this case, the display control unit 104 may display a thumbnail image displayed in the case display region 710 by scrolling the thumbnail image in a horizontal direction in accordance with an amount of movement of the scroll bar 715. Alternatively, when a direction key of the keyboard is pressed in a state where the mouse pointer is positioned on the case display region 710, the display control unit 104 may display a thumbnail image displayed in the case display region 710 by scrolling the thumbnail image in a direction of the pressed key while the key is being pressed.

Moreover, while the information terminal 100 is configured to acquire a thumbnail image whose distance from a retrieval query image is equal to or less than a predetermined threshold from the case retrieval system 300, this is simply an example. For example, the information terminal 100 may always acquire a constant number of thumbnail images from the case retrieval system 300 in a descending order of degrees of similarity. Alternatively, the information terminal 100 may acquire thumbnail images from the case retrieval system 300 so as to always include a constant number of thumbnail images representing a given definitively diagnosed disease name.

Moreover, as a method of displaying thumbnail images in the case display region 710, a display method can be adopted which involves displaying a thumbnail image whose distance from a retrieval query image is shortest at a left end of an uppermost row, displaying thumbnail images so that distances sequentially increases rightward, and once reaching a right end of the same row, displaying a thumbnail image with a next longer distance at a left end of a second-from-top row, for example. In other words, a display method can be adopted which involves displaying thumbnail images in an ascending order of distances so as to meander from top left to bottom right in the case display region 710.

Obviously, the present embodiment may adopt other display methods. For example, a display method can be adopted which involves displaying a thumbnail image whose distance is shortest at an upper end of a leftmost column, displaying thumbnail images so that distances sequentially increases downward, and once reaching a lower end of the same column, displaying a thumbnail image with a next longer distance at an upper end of a second-from-left column. In addition, a configuration may be adopted in which the user can switch among the plurality of display methods.

Furthermore, while distance is adopted as a degree of similarity in the example described above, any indicator such as cosine similarity may be adopted as long as the indicator represents a degree of similarity between images. When cosine similarity is adopted, the degree of similarity between two images that are comparison objects increases as the value approaches 1.

Moreover, while details will be provided later, similar cases displayed in the case display region 710 can be narrowed down by a disease name displayed in the disease name list display region 730 or by a lesion distribution displayed in the distribution list display region 750. A currently set narrowing condition of similar cases is displayed in a display condition display region 714. Since the example shown in FIG. 6 shows a state immediately after similar case retrieval and the similar cases have not been narrowed down in any way, "all disorders" are displayed in the display condition display region 714.

The layout region 720 is arranged in a bottom left part of the basic screen K2 shown in FIG. 6, for example. In addition, the layout region 720 is used to display an image which the user wishes to observe in detail among the similar case thumbnail images displayed in the case display region 710 on a medical image viewer of the display 101a. As shown in FIG. 5, four medical image viewers 610 to 640 are arranged in two rows and two columns on the display 101a. In addition, four display boxes 721 to 724 exist in two rows and two columns in the layout region 720. In this manner, the number and arrangement of the medical image viewers 610 to 640 displayed on the display 101a and the number and arrangement of the display boxes 721 to 724 in the layout region 720 are matched with each other. As shown in FIG. 5, in conformance of a retrieval query image displayed in the medical image viewer 610, a thumbnail image of the retrieval query image is initially displayed in the display box 721. Moreover, the display box 721 that displays the thumbnail image of the retrieval query image is an example of the first display box.

The other display boxes 722 to 724 display thumbnail images of similar cases in conjunction with the medical image viewers 620 to 640. Specifically, when the input control unit 103 senses one of the thumbnail images displayed in the case display region 710 being dragged and dropped in any one of the display boxes 722 to 724, the display control unit 104 displays the one thumbnail image in the display box and, at the same time, displays a slice image corresponding to the thumbnail image on the medical image viewer corresponding to the display box. In this manner, the medical image viewers 610 to 640 correspond one-to-one with the display boxes 721 to 724.

In the example shown in FIG. 6, since the display boxes 722 to 724 are empty, the medical image viewers 620 to 640 shown in FIG. 5 are also blank. Moreover, the display boxes 722 to 724 that display similar cases are examples of the second display box.

By dragging and dropping using a mouse, the user moves a thumbnail image that the user wishes to observe in detail from the case display region 710 to the layout region 720. For example, assuming that the user has moved a thumbnail image to the display box 722, a slice image corresponding to the thumbnail image is displayed on the medical image viewer 620 corresponding to the display box 722. In a similar manner, assuming that the user has moved a thumbnail image to the display box 723, a slice image corresponding to the thumbnail image is displayed on the medical image viewer 630 corresponding to the display box 723. In other words, when a thumbnail image is moved to any display box among the display boxes 721 to 724, a thumbnail image of a similar case is displayed adjacent to a thumbnail image of a retrieval query image. Therefore, the user can compare a diagnosis object case with a similar case on a thumbnail image level and can promptly determine a degree of similarity between both cases. In other words, since an amount of information in a thumbnail image is smaller than that of a slice image, the user can make a rough estimate as to how similar the diagnosis object case and the similar case arranged adjacent to each other in the layout region 720 are to each other. Therefore, the user can efficiently narrow down a final candidate of a similar case which needs to be compared in detail at a slice image level with the diagnosis object case from the large number of similar cases displayed in the case display region 710.

In a similar manner, the display 101a also displays slice images of the retrieval query image and a similar case in the same arrangement relationship as in the layout region 720. Therefore, once an operation for narrowing down a final candidate of a similar case in the layout region 720 is finished, the diagnosis object case and a similar case that has been narrowed down as a final candidate are displayed on a slice image level in the display 101a without having to input any operation. As a result, the user can make a smooth transition to a next operation step that is to diagnostically interpret a diagnosis object and a similar case that is a final candidate in detail.

The disease name list display region 730 to which a heading reading "disease name list" is attached is arranged in an upper part of a left side of the basic screen K2 shown in FIG. 6. Definitively diagnosed disease names of all similar cases acquired as a similar case retrieval result are displayed in the disease name list display region 730. After a diagnosis is made and a definitively diagnosed disease name is assigned, a diagnosis object case is accumulated as a similar case in the case retrieval system 300. Therefore, a definitively diagnosed disease name assigned by a diagnosis is assigned in advance to each similar case.

FIG. 8 is an enlarged view of the disease name list display region 730. In FIG. 8, definitively diagnosed disease names are displayed divided into broadly categorized disease names (731, 734, 737, 741, and 744) and finely categorized disease names (732, 733, 735, 736, 738, 739, 740, 742, 743, and 745). In the example shown in FIG. 8, mycosis 731, neoplastic 734, nonneoplastic 737, mycobacteriosis 741, and other 744 are displayed as broadly categorized disease names.

In addition, in the example shown in FIG. 8, aspergillosis 732 and cryptococcosis 733 are displayed as finely categorized disease name of mycosis 731. Furthermore, lung cancer 735 and metastatic lung cancer 736 are displayed as finely categorized disease names of neoplastic 734. Moreover, lung abscess 738, sarcoidosis 739, and septic emboli 740 are displayed as finely categorized disease names of nonneoplastic 737. In addition, nontuberculous mycobacteria (NTM) 742 and tuberculosis 743 are displayed as finely categorized disease names of mycobacteriosis 741. Furthermore, bronchiectasis 745 is displayed as a finely categorized disease name of other 744.

Figure 9:
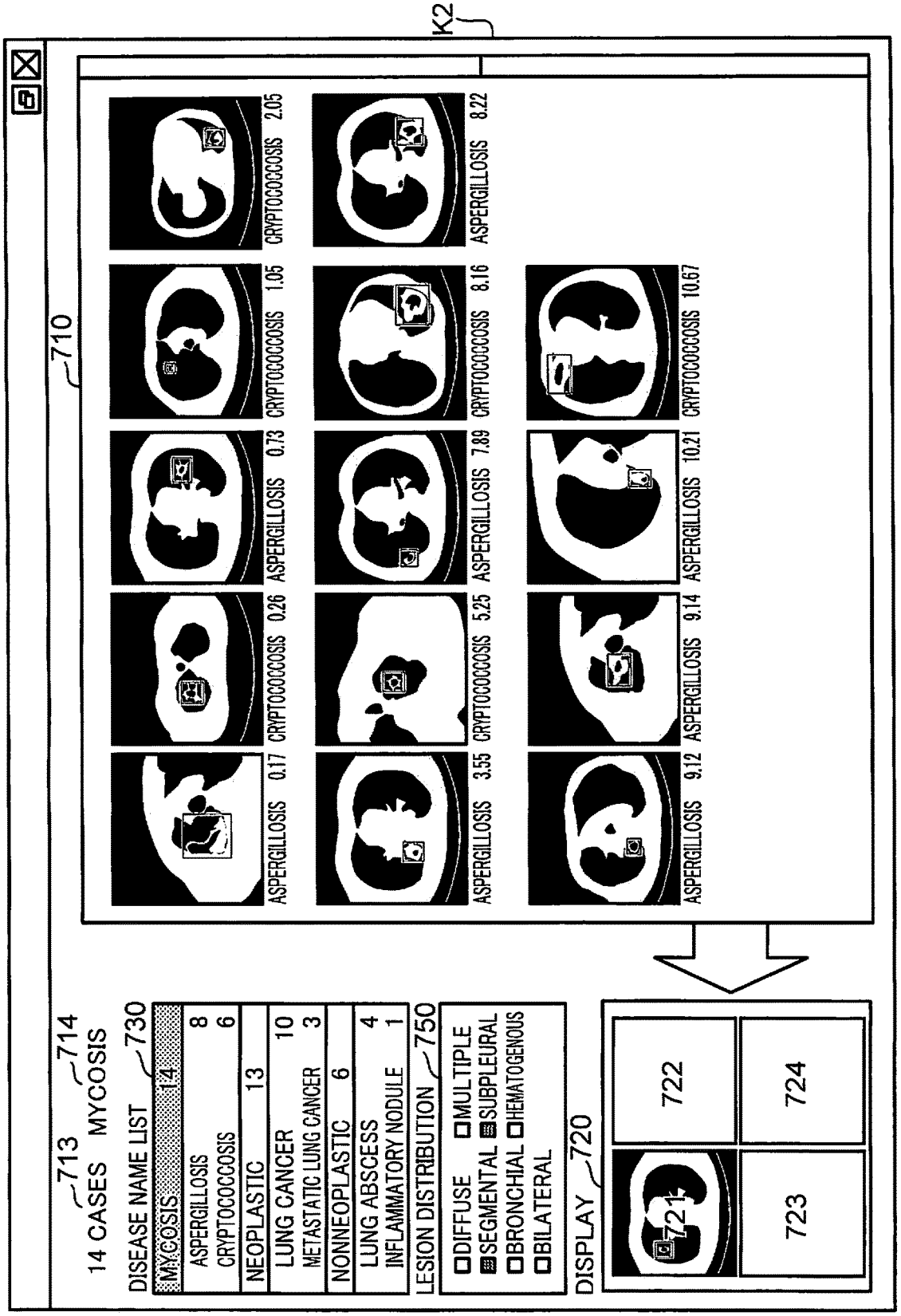
FIG. 9 is a diagram showing a basic screen when similar cases are narrowed down by "mycosis".
Figure 10:
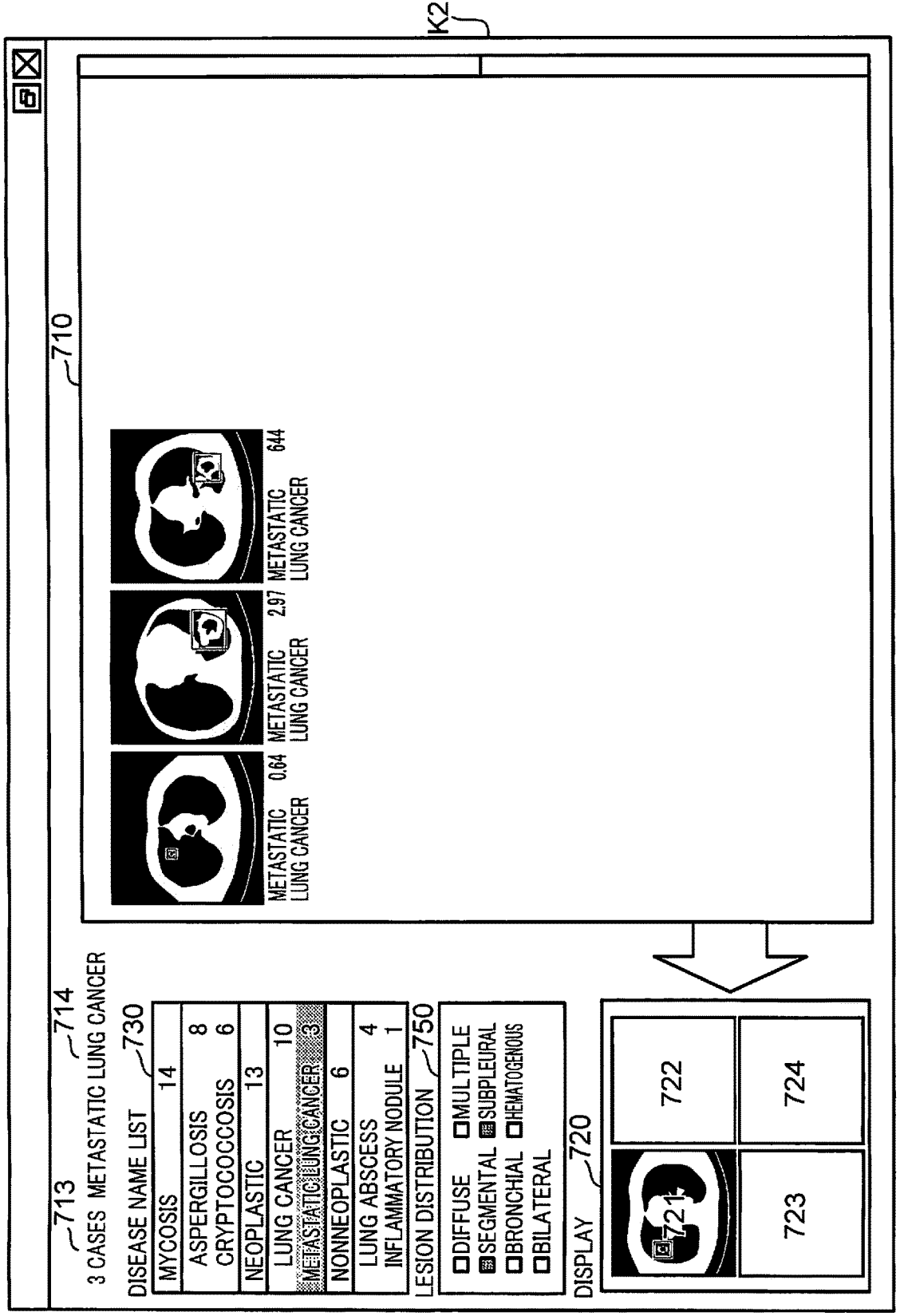
FIG. 10 is a diagram showing a basic screen when similar cases are narrowed down by "metastatic lung cancer".

In addition, the number of cases corresponding to a disease name is displayed besides broadly categorized disease names and finely categorized disease names. By selecting an arbitrary row of a broadly categorized disease name or a finely categorized disease name in the disease name list display region 730, the user can narrow down a similar case to be displayed in the case display region 710. While 62 similar cases including various disorders are set as display objects in a state immediately following similar case retrieval as shown in FIG. 6, when the row of mycosis 731 in FIG. 8 is clicked using a mouse, the display control unit 104 only displays similar cases of mycosis in the case display region 710 as shown in FIG. 9. Furthermore, when the row of metastatic lung cancer 736 in FIG. 8 is clicked using a mouse, the display control unit 104 only displays similar cases of metastatic lung cancer in the case display region 710 as shown in FIG. 10.

At this point, the display control unit 104 displays narrowed-down disease names in the display condition display region 714 so as to show what kind of narrowing condition applies to the similar cases currently displayed in the case display region 710. FIG. 9 is a diagram showing the basic screen K2 when similar cases are narrowed down by "mycosis". FIG. 10 is a diagram showing the basic screen K2 when similar cases are narrowed down by "metastatic lung cancer".

In the example shown in FIG. 9, since similar cases are narrowed down by "mycosis", "mycosis" is displayed in the display condition display region 714. In the example shown in FIG. 10, since similar cases are narrowed down by "metastatic lung cancer", "metastatic lung cancer" is displayed in the display condition display region 714.

In addition, at this point, the display control unit 104 shows the number of similar cases currently displayed in the case display region 710 by displaying the number in the number of retrieved results display region 713. In the example shown in FIG. 9, since there are 14 similar cases corresponding to "mycosis", "14" is displayed in the number of retrieved results display region 713. In the example shown in FIG. 10, since there are 3 similar cases corresponding to "metastatic lung cancer", "3" is displayed in the number of retrieved results display region 713.

Due to this function, only similar cases with disease names that are assumed to be objects of image diagnosis by a radiologist are displayed in the case display region 710 and the radiologist can readily check whether or not the diagnosis object case is consistent with the assumed disease names.

The distribution list display region 750 to which a heading reading "lesion distribution" is attached is arranged in a middle part of the left side of the basic screen K2 shown in FIG. 6. Types of lesion distributions of all similar cases acquired from the case retrieval system 300 as a result of similar case retrieval are displayed in the distribution list display region 750.

FIG. 11 is an enlarged view of the distribution list display region 750. In the example shown in FIG. 11, names of seven lesion distributions are displayed and a check mark is arranged to the left of the name of each lesion distribution. In the example shown in FIG. 11, diffuse 751, segmental 752, bronchial 753, bilateral 754, multiple 755, subpleural 756, and hematogenous 757 are displayed as lesion distributions.

These lesion distributions are defined in advance and a distribution flag value (applicable: 1, not applicable: 0) indicating whether or not a similar case corresponds to any of diffuse 751 to hematogenous 757 is assigned to each similar case. Similar cases include those in which all distribution flag values are set to not applicable (: 0) and those in which a plurality of all distribution flag values are set to applicable (: 1).

The case retrieval system 300 according to the present embodiment retrieves a similar case having a region of interest that is similar to a region of interest set by the user in a slice image of a diagnosis object case. There may exist lesions other than the slice image to which a region of interest is set by the user. In addition, there may be cases where, after retrieving a similar case based on the slice image to which a region of interest is set, the user wishes to compare a slice image other than the slice image with the retrieved similar case. In such a case, the user inputs a slice feeding operation on the medical image viewer 610 to cause the medical image viewer 610 to display another slice image and performs an operation for comparing the slice image with the retrieved similar case. In this case, if only similar cases related to a lesion of interest among all retrieved similar cases are displayed in the case display region 710, an operation of extracting a slice image having a desired lesion from slice images other than the slice image to which a region of interest is set can be performed smoothly. In consideration thereof, in the present embodiment, a function for narrowing down retrieved similar cases by a desired lesion distribution is provided to enable this operation to be performed in a smooth manner.

In the present embodiment, as lesion distributions in a lung field region, the lesion distributions represented by diffuse 751 to hematogenous 757 shown in FIG. 11 are adopted. In addition, as shown in FIG. 11, with respect to check boxes and disease name distributions, the display control unit 104 displays lesion distributions that can be narrowed down in an active state and displays lesion distributions that cannot be narrowed down in an inactive state. In this case, a state in which brightness is higher than the inactive state is adopted as the active state and a state in which brightness is lower than the active state is adopted as the inactive state.

In the example shown in FIG. 11, diffuse 751, bronchial 753 to multiple 755, and hematogenous 757 are displayed in the active state and segmental 752 and subpleural 756 are displayed in the inactive state. This is because, among all similar cases acquired by a similar case retrieval, the distribution flag values of diffuse 751, bronchial 753 to multiple 755, and hematogenous 757 are currently set to 1 (applicable) in at least one of the similar cases while the distribution flag values of segmental 752 and subpleural 756 are currently set to 0 (not applicable) in all of the acquired similar cases.

When the input control unit 103 senses that a check mark has been input to one or more check boxes among the check boxes in the active state, the display control unit 104 displays only similar cases corresponding to lesion conditions for which a check mark had been input in the case display region 710.

Moreover, for segmental 752 and subpleural 756, the distribution flag value is set to 0 (not applicable) in all of the similar cases acquired as a retrieval result. Therefore, when a configuration that enables a check mark to be input for segmental 752 or subpleural 756 is adopted and a check mark is input for these lesion distributions, no similar case is to be displayed in the case display region 710. As a result, inputting a check mark becomes meaningless. In consideration thereof, in the present embodiment, in order to avoid such circumstances, a lesion distribution for which the distribution flag value is set to 0 (not applicable) in all of the similar cases acquired as a retrieval result is displayed in the inactive state.

Figure 13:
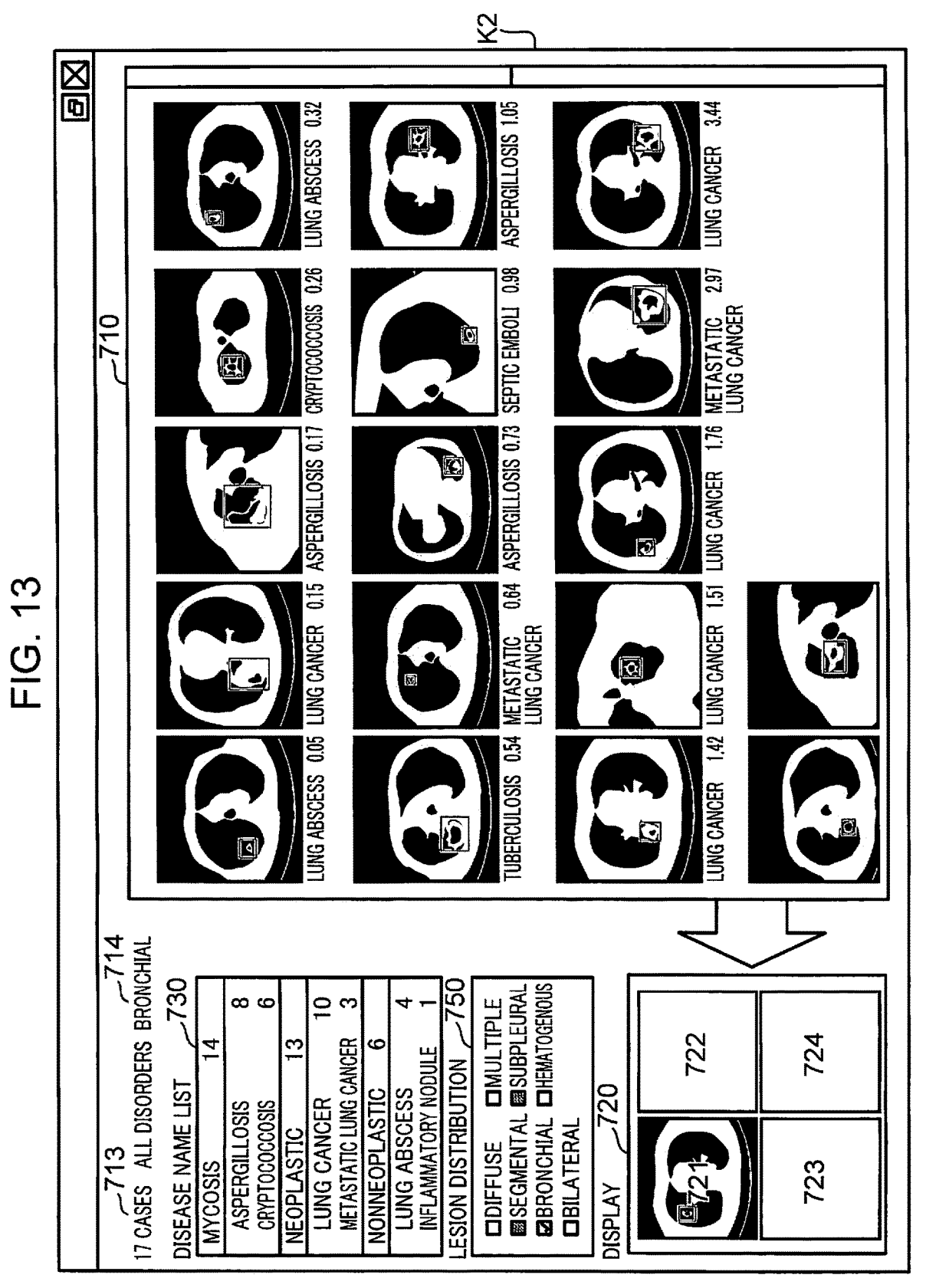

FIG. 12 is a diagram showing the distribution list display region 750 in which a check mark is input. FIG. 13 is a diagram showing the basic screen K2 having been narrowed down by a bronchial lesion distribution. When a check mark is input to the check box of bronchial 753 as shown in FIG. 12, the display control unit 104 displays only similar cases with a bronchial lesion distribution in the case display region 710 as shown in FIG. 13. In this example, there are 17 similar cases with a bronchial lesion distribution. Therefore, the display control unit 104 displays "17" in the number of retrieved results display region 713. In addition, the display control unit 104 displays a disease name that is a display object and "bronchial" that is the name of the lesion distribution in the display condition display region 714. In the example shown in FIG. 13, since similar cases have not been narrowed down by a disease name listed in the disease name list display region 730, the display condition display region 714 displays "all disorders".

Figure 15:
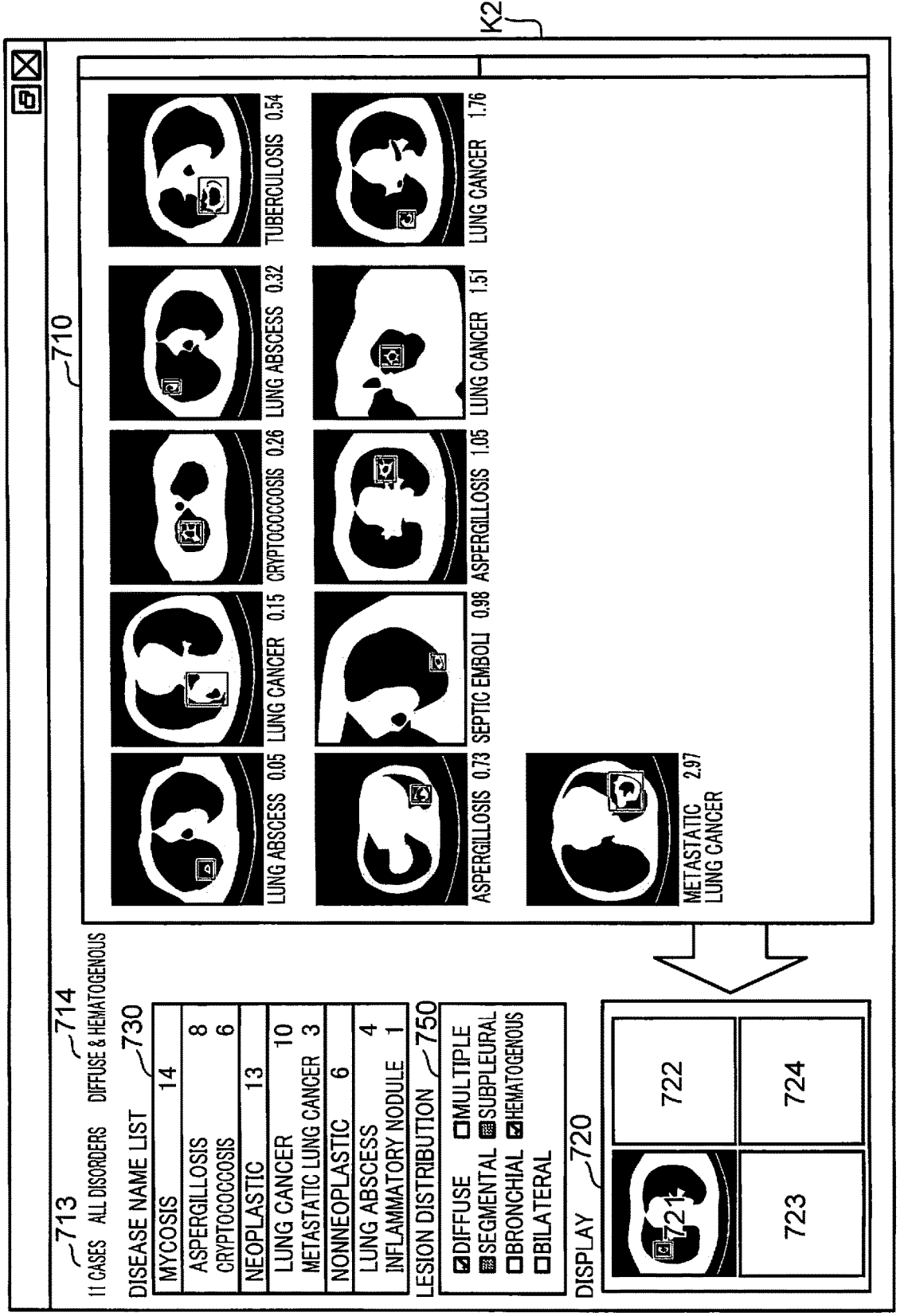
FIG. 15 is a diagram showing a basic screen having been narrowed down by a plurality of lesion distributions.

FIG. 14 is a diagram showing the distribution list display region 750 in which a plurality of check marks are input. FIG. 15 is a diagram showing the basic screen K2 having been narrowed down by a plurality of lesion distributions. In the example shown in FIG. 14, check marks are input for diffuse 751 and hematogenous 757. Therefore, the display control unit 104 displays similar cases with diffuse and hematogenous lesion distributions in the case display region 710 as shown in FIG. 15. In this example, there are 11 similar cases with diffuse and hematogenous lesion distributions. Therefore, the display control unit 104 displays "11" in the number of retrieved results display region 713. In addition, the display control unit 104 displays a disease name that is a display object (in this case, "all disorders" since similar cases have not been narrowed down by a disease name) and "diffuse and hematogenous" that are the names of the lesion distributions in the display condition display region 714.

Figure 18:
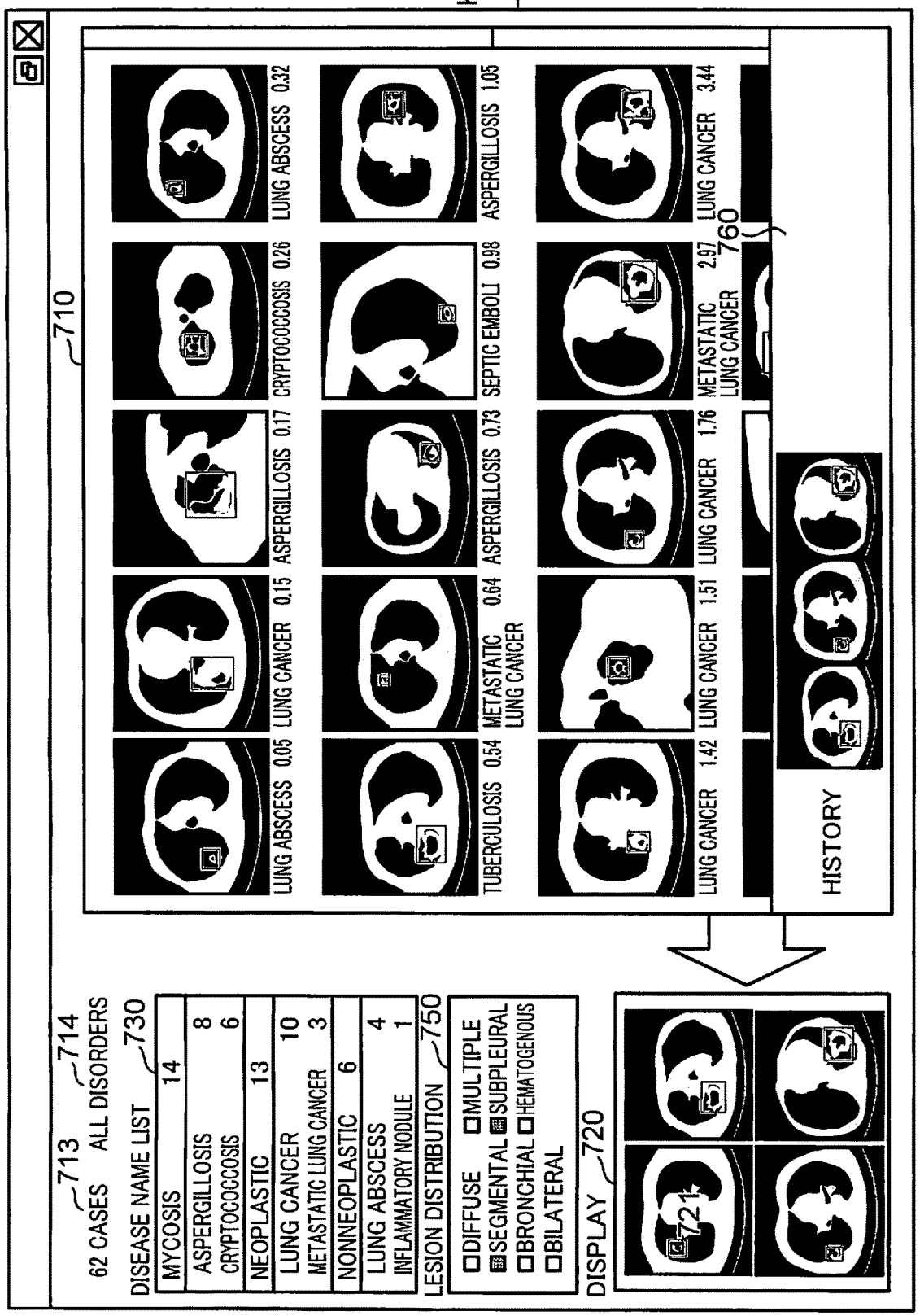
FIG. 18 is a diagram showing a basic screen displaying a history management region.

Next, the history management region 760 that is not displayed on the basic screen K2 shown in FIG. 6 will be described. FIG. 18 is a diagram showing the basic screen K2 displaying the history management region 760. The history management region 760 is an example of the third display region. When the input control unit 103 senses an operation for positioning the mouse cursor near a lowermost part of the case display region 710 or for pressing a key assigned in advance, the display control unit 104 displays the history management region 760 explicitly labeled "history" at a left end thereof so as to overlap with the basic screen K2 as shown in FIG. 18. The history management region 760 is a rectangular strip-shaped display region that is displayed in a lower part of the basic screen K2 and a horizontal width thereof is approximately the same as a horizontal width of the case display region 710. In addition, in the history management region 760, thumbnail images moved to the layout region 720 among the thumbnail images of similar cases displayed in the case display region 710 and thumbnail images directly moved to the history management region 760 are arranged from left to right as history.

Moreover, the history management region 760 is displayed in a lower part of the basic screen K2 because among the similar cases displayed in the case display region 710, the higher a similar case is in the case display region 710, the more similar the similar case is to the diagnosis object case and therefore the more important. Therefore, a situation where important similar cases become hidden can be avoided even when the history management region 670 is displayed. Moreover, the history management region 760 other than a region in which thumbnail images are displayed is translucently displayed. Therefore, thumbnail images in the case display region 710 that is hidden behind the history management region 760 are prevented from being completely hidden.

In this case, the display control unit 104 displays thumbnail images to be displayed in the history management region 760 in a smaller size than the thumbnail images to be displayed in the case display region 710. The thumbnail images displayed in the history management region 760 are images which have already been displayed once in the layout region 720 and the case display region 710 and on the medical image viewers 610 to 640 and which have already been confirmed once by the user. Therefore, displaying the thumbnail images in a smaller size than the thumbnail images displayed in the case display region 710 does not pose a problem. In consideration thereof, in the present embodiment, the thumbnail images displayed in the history management region 760 are set smaller than the thumbnail images displayed in the case display region 710 and the layout region 720. Accordingly, as many thumbnail images as possible can be displayed in the history management region 760 that has a limited display space.

Moreover, since the history management region 760 is a display region that is elongated in a horizontal direction, when there are a large number of thumbnail images moved to the layout region 720 and the history management region 760, all of the moved thumbnail images cannot be displayed.

Figure 19:
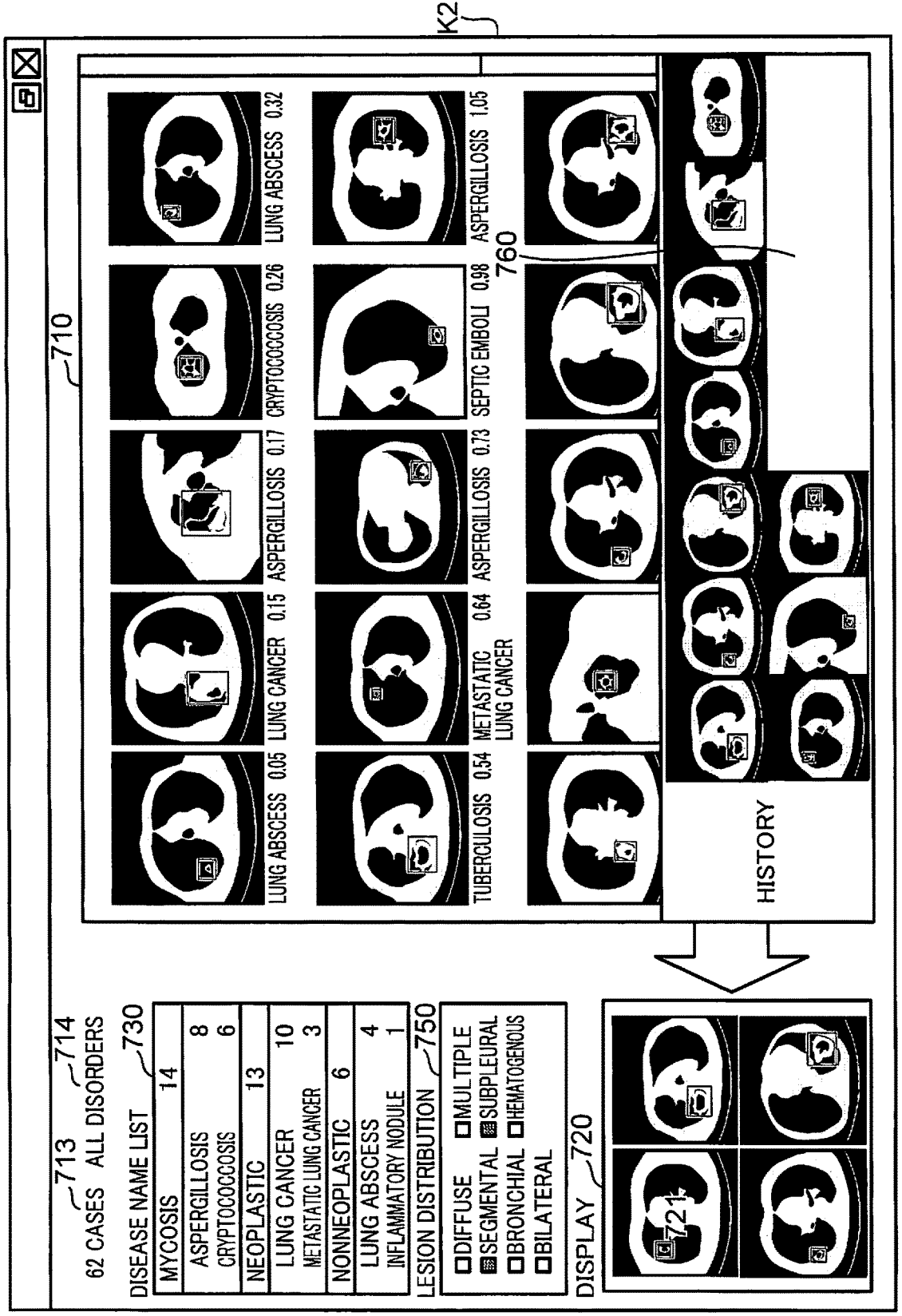
FIG. 19 is a diagram showing a basic screen displaying a history management region in which a display space is expanded to two rows.

In consideration thereof, in the present embodiment, when the history management region 760 becomes full of thumbnail images, the display control unit 104 expands the display space of the history management region 760 to two rows as shown in FIG. 19 so that all of the moved thumbnail images can be displayed. FIG. 19 is a diagram showing the basic screen K2 displaying the history management region 760 in which the display space is expanded to two rows. In the example shown in FIG. 19, first to seventh thumbnail images in the order of movement to the layout region 720 and the history management region 760 are displayed in a first row and three thumbnail images moved eighth and thereafter in the order of movement are displayed in a second row.

Moreover, the display control unit 104 may sequentially expand the number of rows of the history management region 760 such as by expanding the number of rows of the history management region 760 to three rows when the history management region 760 with a display space expanded to two rows becomes full of thumbnail images, expanding the number of rows of the history management region 760 to four rows when the history management region 760 after expansion becomes full of thumbnail images, and so on.

Figure 20:
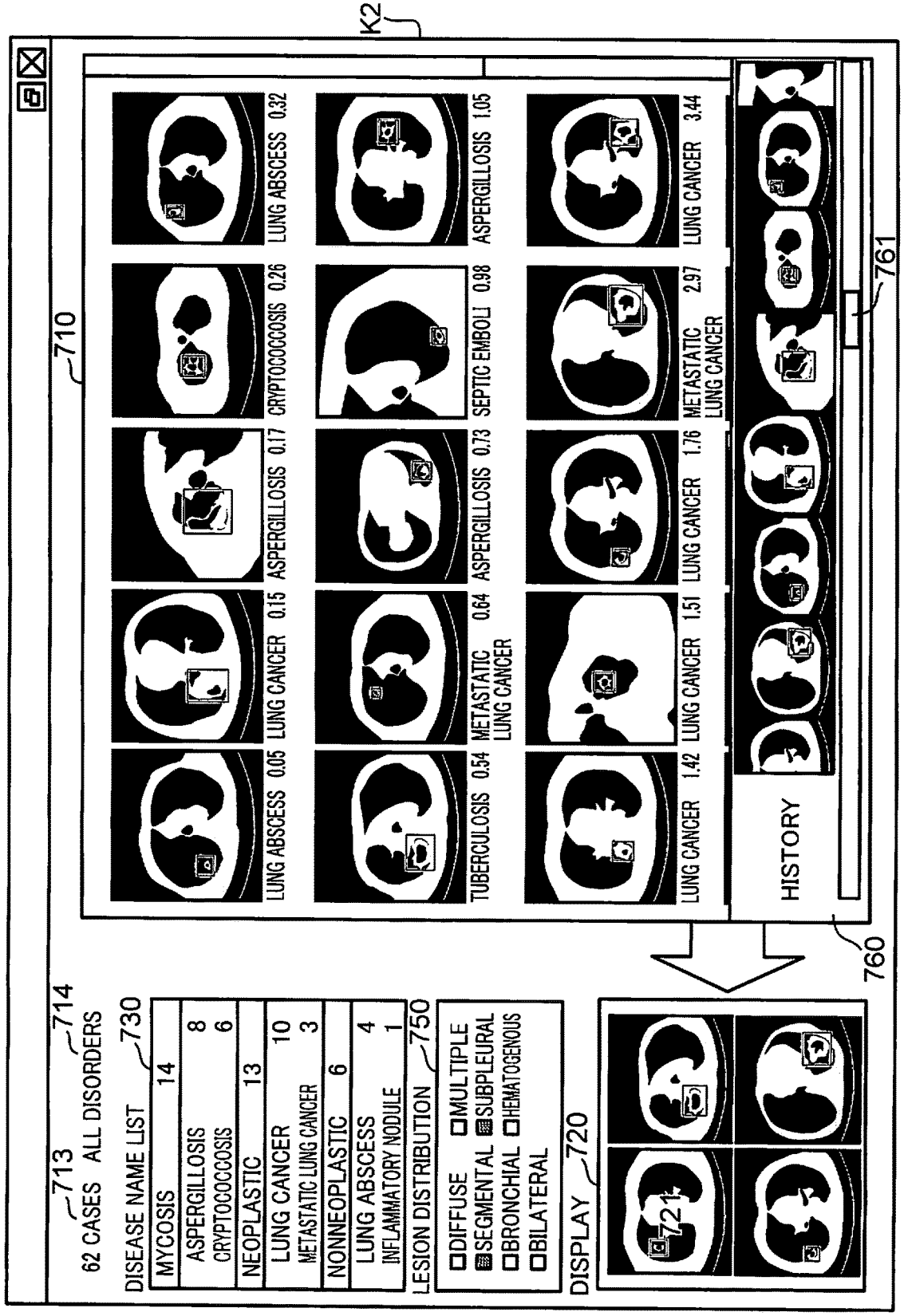
FIG. 20 is a diagram showing a history management region in which a scroll bar is displayed.

In addition, as shown in FIG. 20, the display control unit 104 may display a scroll bar 761 that is elongated in a horizontal direction in a lower part of the history management region 760 instead of increasing the number of rows of the history management region 760. FIG. 20 is a diagram showing the history management region 760 in which the scroll bar 761 is displayed. In this case, when the scroll bar 761 is moved horizontally, the display control unit 104 may scroll thumbnail images displayed in the history management region 760 in the horizontal direction in accordance with an amount of movement of the scroll bar 761. Accordingly, thumbnail images that cannot be displayed in a display space corresponding to one row can be displayed in the history management region 760 that only has a display space corresponding to one row.

Figure 21:
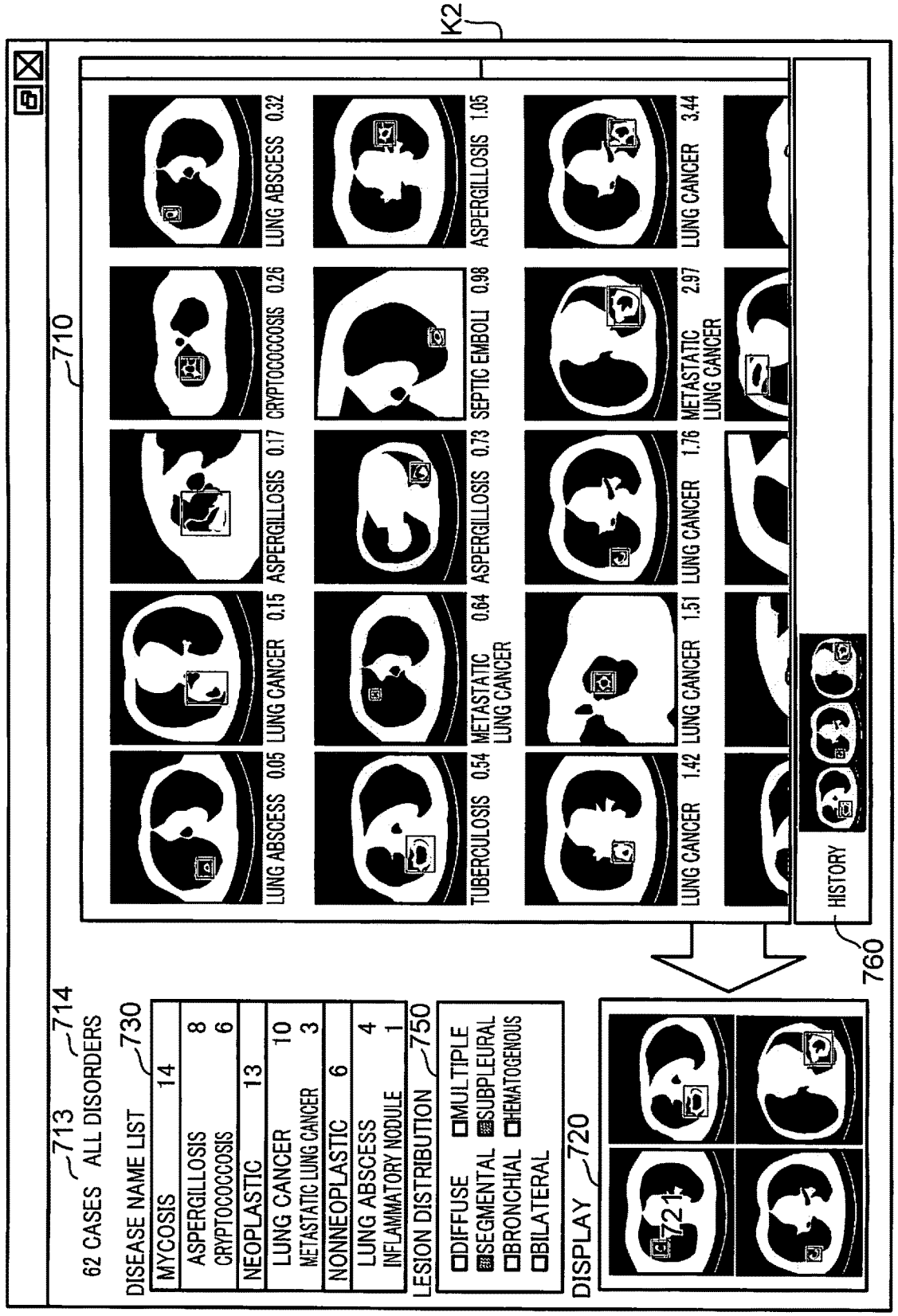
FIG. 21 is a diagram showing a basic screen in a case when a mode that displays a history management region from an initial state is adopted.

Moreover, in the present embodiment, while a mode is adopted in which the history management region 760 is hidden in an initial state and appears when necessary, the history management region 760 may be displayed in an initial state as shown in FIG. 21. FIG. 21 is a diagram showing a basic screen in a case where a mode that displays the history management region 760 from an initial state is adopted.

In the example shown in FIG. 21, in order to display as many thumbnail images in the history management region 760 as possible, the thumbnail images to be displayed in the history management region 760 are set even smaller than a case where the mode shown in FIG. 18 is adopted. In this case, when the mode shown in FIG. 21 is adopted, the display control unit 104 may expand the history management region 760 shown in FIG. 21 so as to assume a same size as the history management region 760 shown in FIG. 16 as the mouse cursor is brought close to the history management region 760 that is constantly displayed.

Figure 16:
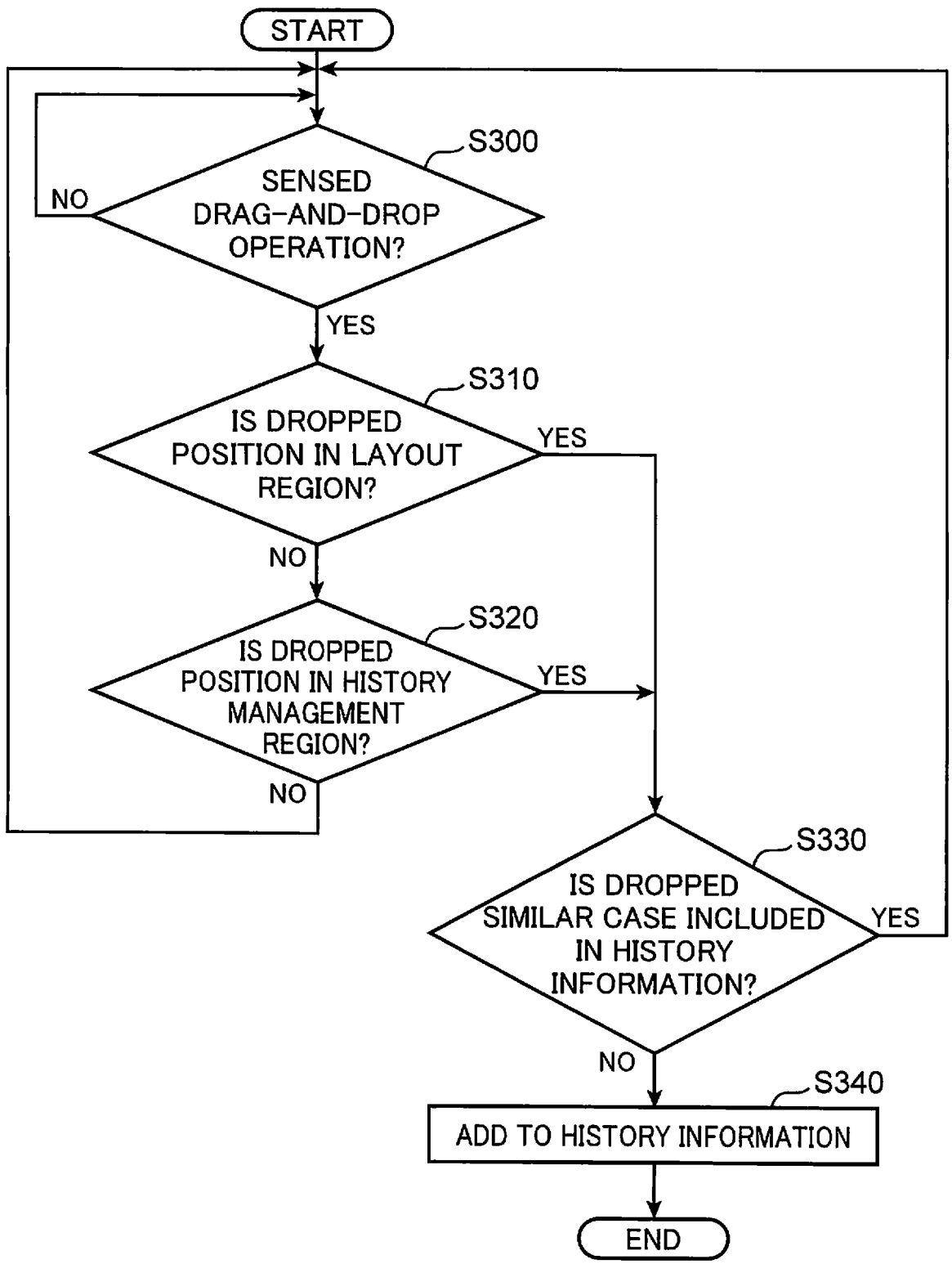
FIG. 16 is a flow chart showing a process for registration to history information.

Moreover, the thumbnail images displayed in the history management region 760 are registered in history information 1701 (refer to FIG. 17) that is managed by the history information managing unit 107. Therefore, the display control unit 104 identifies a thumbnail image displayed in the history management region 760 by referring to history information. Hereinafter, a registration process to history information 1701 will be described. FIG. 16 is a flow chart showing a registration process to history information 1701. First, when the input control unit 103 senses an operation where a thumbnail image displayed in the case display region 710 is dragged and dropped (YES in S300), a judgment is made on whether or not a position at which the thumbnail image is dropped is in the layout region 720 (S310). On the other hand, if a drag-and-drop operation is not detected, (NO in S300), the process of S300 is repeated.

When a position where the thumbnail image is dropped is inside the layout region 720 (YES in S310), the process advances to S330. On the other hand, when the position where the thumbnail image is dropped is outside the layout region 720 (NO in S310), the process advances to S320.

In S320, the input control unit 103 judges whether or not the dropped position is inside the history management region 760. When the dropped position is inside the history management region 760 (YES in S320), the process advances to S330. On the other hand, when the dropped position is outside the history management region 760 (NO in S320), the process returns to S300.

In S330, the history information managing unit 107 judges whether or not a similar case ID of the dropped thumbnail image is already included in the history information 1701. FIG. 17 is a diagram showing a data configuration of the history information 1701. The history information 1701 is information for managing a thumbnail image to be displayed in the history management region 760. The history information 1701 includes a "history ID" field and a "similar case ID" field. The "history ID" is information indicating an order of registration in which a similar case had been registered in the history information 1701. In this case, as the "history ID", a natural number that is incremented by 1 every time a new similar case is registered in the history information 1701 is adopted. The "similar case ID" is an identifier for uniquely identifying a similar case. In the example shown in FIG. 17, a symbol string constituted by "SIM" followed by a numerical value is adopted. Moreover, the "similar case ID" is associated with thumbnail image data 4500 in the similar case data 4000 shown in FIG. 26. Therefore, if a similar case ID is known, a corresponding thumbnail image can be identified.

When the similar case of the dropped thumbnail image is included in the history information 1701 (YES in S330), since a corresponding similar case need not be registered in the history information 1701, the process returns to S300. On the other hand, when the similar case of the dropped thumbnail image is not included in the history information 1701 (NO in S330), the history information managing unit 107 adds the similar case ID of the dropped thumbnail image to the history information 1701 (S340). In this case, the history information managing unit 107 issues a value obtained by adding 1 to a latest "history ID" that is already registered in the history information 1701 as a new "history ID", associates a "similar case ID" that is an addition object with the "history ID", and registers the "similar case ID" in the history information 1701.

Therefore, when displaying thumbnail images in the history management region 760, the display control unit 104 sequentially arranges the thumbnail images from a left end to a right end of the history management region 760 in an ascending order of "history IDs" in the history information 1701. At this point, the display control unit 104 may identify thumbnail image data 4500 from similar case data 4000 corresponding to the "similar case ID" registered in the history information 1701.

Next, the significance of accumulating similar cases in the history information 1701 will be described. While thumbnail images of a large number of similar cases are displayed in the case display region 710, the user selects similar cases that are similar to a diagnosis object case from the displayed similar cases. The selected similar cases are moved to the layout region 720. However, since there is a limit to the number of similar cases that can be displayed at the same time in the layout region 720, similar cases that are overwritten and erased from the layout region 720 must be saved.

This is because situations may arise where the user desires to compare a similar case erased from the layout region 720 with the diagnosis object case once again and, in such situations, searching a corresponding similar case from the case display region 710 can be a hassle for the user.

In addition, in the present embodiment, besides a similar case dragged and dropped in the layout region 720 being registered in the history information 1701, a similar case that is directly dragged and dropped in the history management region 760 is also registered in the history information 1701.

There may be cases where the user picks out, in advance, several similar cases of interest from the large number of similar cases displayed in the case display region 710 to be viewed carefully at a later time. In such a case, it is useful to have a function for causing a thumbnail image of a similar case to be directly dragged and dropped in the history management region 760 and have the thumbnail image displayed in the history management region 760. Accordingly, the present embodiment is mounted with such a function.

Moreover, in the description given above, the history management region 760 displays a thumbnail image dragged and dropped to the layout region 720. However, this is simply an example. For example, a mode may be adopted in which the history management region 760 displays a thumbnail image which had been originally dragged and dropped to the layout region 720 but had subsequently been overwritten by another thumbnail image and erased from the layout region 720 as well as a thumbnail image that had been directly dragged and dropped to the history management region 760. In this case, a thumbnail image currently being displayed in the layout region 720 is no longer displayed in the history management region 760.

When adopting this mode, the history information managing unit 107 may register similar case IDs of the thumbnail image erased from the layout region 720 and the thumbnail image directly dragged and dropped to the history management region 760 in the history information 1701.

FIG. 22 is a diagram showing a data configuration of the patient information 1000. The patient information 1000 is accumulated and managed in the patient information accumulating unit 201 for each patient by the patient information managing unit 202 of the medical information management system 200. Personal information of a patient such as gender and age, clinical information of the patient such as medical history, and examination information of the patient such as a blood test are registered in the patient information 1000. As shown in FIG. 22, the patient information 1000 includes a patient ID 1100, a name 1200, an age 1300, a gender 1400, a medical history 1500, a family medical history 1600, a chief complaint 1700, examination information 1800, and a definitive diagnosis 1900.

The patient ID 1100 is an identifier unique to a patient. The name 1200, the age 1300, the gender 1400, the medical history 1500, the family medical history 1600, and the chief complaint 1700 are, respectively, the name, the age, the gender, the medical history, the family medical history, and the chief complaint of the patient represented by the patient ID 1100. As shown in FIG. 23, the examination information 1800 represents information related to one or more examinations previously undergone by the patient.

FIG. 23 is a diagram showing a data configuration of examination information 1800 that is registered in the patient information 1000 shown in FIG. 22. The examination information 1800 is information related to an examination performed on a patient and is created one piece at a time in correspondence to each examination. The examination information 1800 includes an examination ID 1810, an examination date/time 1820, an examination type 1830, and an examination result 1840. The examination ID 1810 is an identifier unique to an examination. The examination date/time 1820 represents a date and time when the examination had been performed. The examination type 1830 represents a type of the examination. Examples of examination types include a blood test, a respiratory function test, an endoscopic examination, plain radiography, and a CT scan.

In a case of a blood test, various indicators including a white blood cell count, LDH, and GPT correspond to the examination result 1840. In addition, for example, a judgment made by a radiologist based on various indicators also corresponds to the examination result 1840. Furthermore, in a case of an image-based examination such as plain radiography and a CT scan, the examination result 1840 includes pointer information to a photographed image or pointer information to a report containing an image diagnosis result. Moreover, images photographed in the course of an examination are accumulated in the DICOM format in the medical image data accumulating unit 203 of the medical information management system 200.

In addition, when the examination type 1830 is an image-based examination such as plain radiography, a CT, an MRI, and a PET, medical image data thereof are accumulated in a medical image database 2000 stored by the medical image data accumulating unit 203 of the medical information management system 200.

Figure 24:
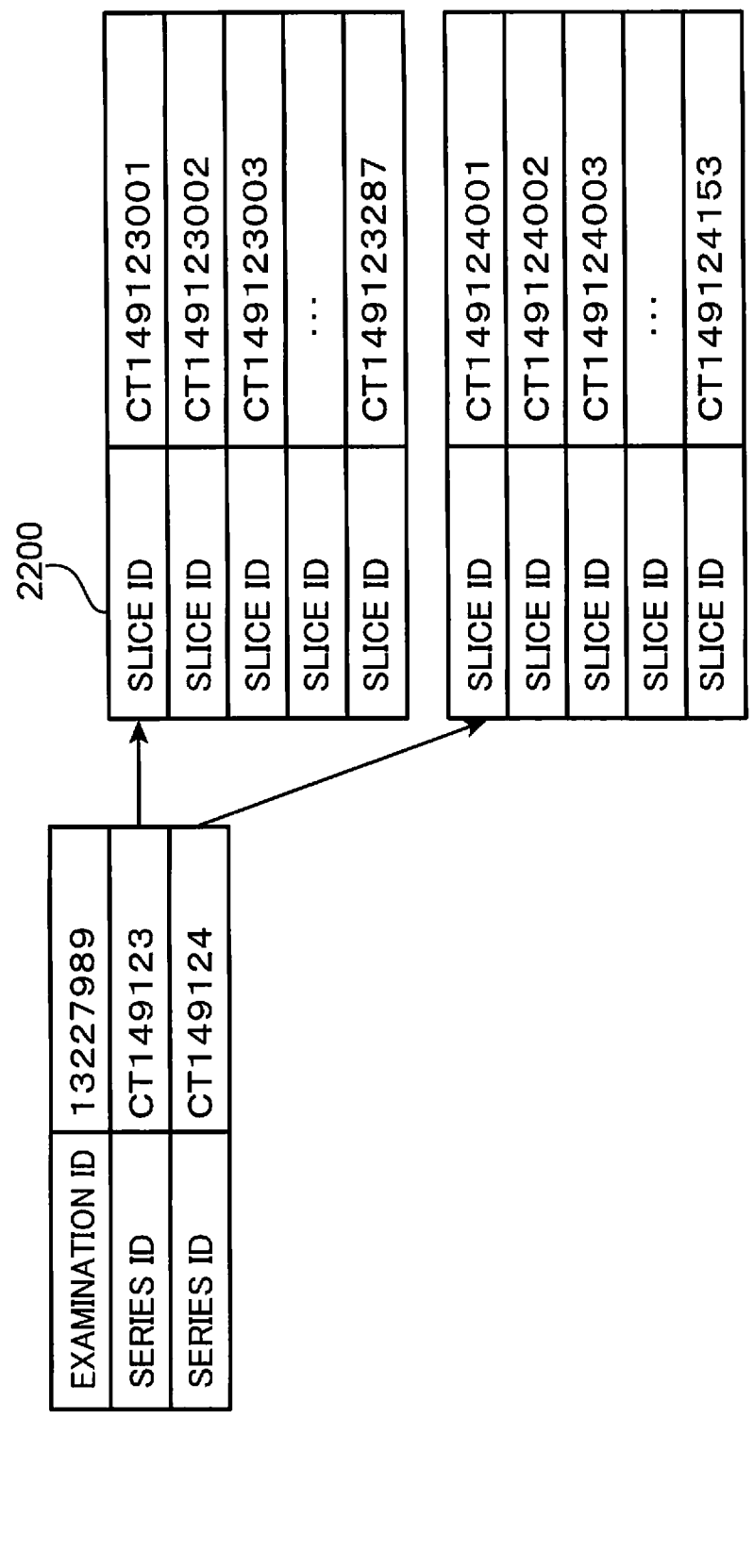
FIG. 24 is a diagram showing a data configuration of a medical image database.

FIG. 24 is a diagram showing a data configuration of the medical image database 2000. The medical image database 2000 includes the examination ID 1810 and a series ID 2100. Since there are cases where a plurality of types of photography (for example, a plain CT and a contrast-enhanced CT) are performed in one examination, there may be cases where a plurality of series IDs 2100 are associated with one examination ID 1810. In other words, the number of acquired series corresponds to the number of types of photography.

In addition, besides each type of photography, a series is obtained for each reconstruction condition of a photographed image. For example, when a photographed image is reconstructed in a lung window setting and a mediastinal window setting, one series is obtained for each of the settings. Moreover, in an image reconstructed in a lung window setting, blood vessels, bronchi, alveoli, and the like of the lungs are displayed highlighted. In addition, in an image reconstructed in a mediastinal window setting, a mediastinum including blood vessels and lymph nodes are displayed highlighted. Since a lung window setting and a mediastinal window setting are obtained by reconstructing an image obtained in one photographic session, when two photographic sessions are performed with plain CT and contrast-enhanced CT and images are reconstructed in a lung window setting and a mediastinal window setting for each of the two photographic sessions, two series in the lung window setting are obtained and two series in the mediastinal window setting are obtained.

In an image-based examination by a CT and an MRI, since a plurality of slice images are acquired by one photographic session, a plurality of slice IDs 2200 are associated with one series ID 2100. Since two series IDs "CT149123" and "CT149124" are associated with the examination ID "13227989" in FIG. 24, it is shown that two CT image series have been obtained from the examination. It is also shown that a plurality of slice IDs 2200 are associated with each of the series IDs "CT149123" and "CT149124".

When the examination type 1830 is an image-based examination such as plain radiography, a CT, an MRI, and a PET, a diagnostic report 3000 such as that shown in FIG. 25 is accumulated in the diagnostic report managing unit 205 of the medical information management system 200. A diagnostic result by a radiologist with respect to each examination is registered in the diagnostic report 3000. FIG. 25 is a diagram showing a data configuration of the diagnostic report 3000.

The diagnostic report 3000 includes the examination ID 1810, findings 3100, and a diagnosis 3200. The examination ID 1810 is the same as the examination ID 1810 shown in FIG. 23. Accordingly, the diagnostic report 3000 and the examination information 1800 are associated with each other. A text representing findings of the radiologist with respect to the examination is registered in the findings 3100. A text representing a diagnosis of the radiologist with respect to the examination is registered in the diagnosis 3200.

FIG. 26 is a diagram showing a data configuration of similar case data 4000. The similar case data 4000 is data that is referred to when retrieving a similar case that is similar to a diagnosis object case. One piece of similar case data 4000 is created corresponding to one similar case. Moreover, the similar case data 4000 is an example of the additional information of similar case data. The similar case data 4000 is accumulated for each similar case in the similar case data accumulating unit 301 of the case retrieval system 300. As shown in FIG. 26, the similar case data 4000 includes a similar case ID 4100, a slice ID 4200, region of interest information 4300, image feature data 4400, thumbnail image data 4500, lesion distribution information 4600, a definitive diagnosis (broadly categorized disease name) 4700, and a definitive diagnosis (finely categorized disease name) 4800.

The similar case ID 4100 is an identifier of the similar case data 4000. In this case, since one piece of similar case data is generated for each region of interest set in a slice image of a similar case, the similar case ID 4100 can also be considered an identifier of a region of interest. In the example shown in FIG. 26, the similar case ID 4100 is constituted by a symbol string constituted by "SIM" followed by a numeral.

Figure 27:
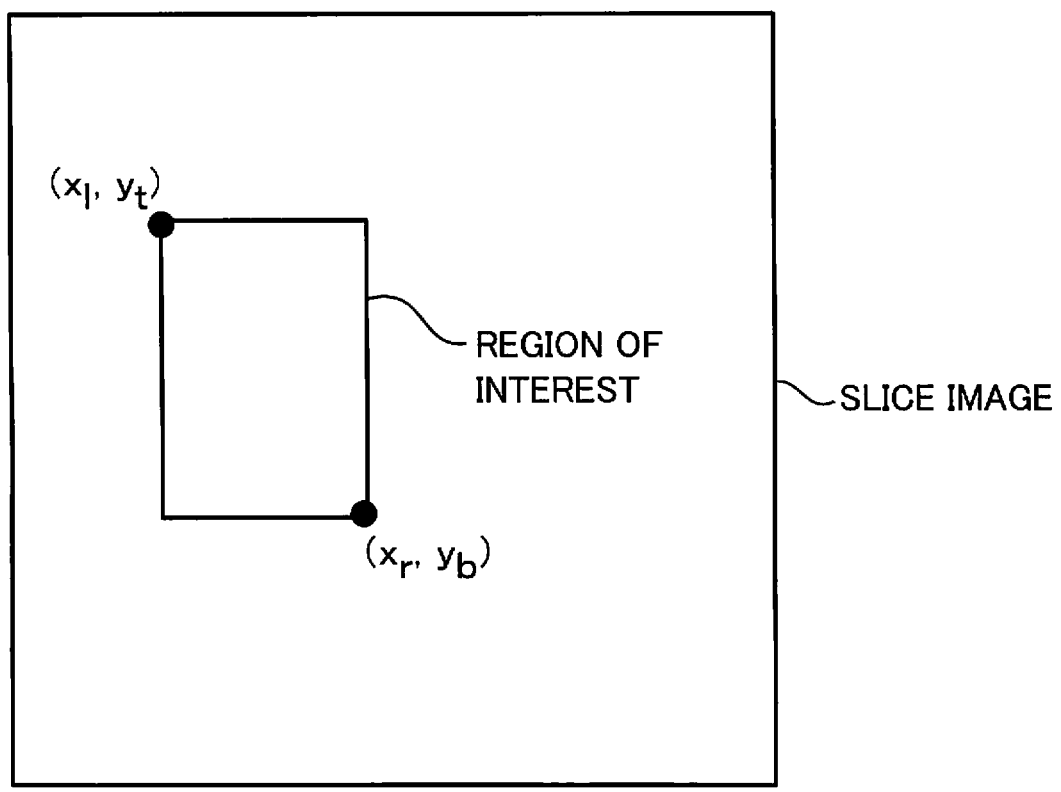
FIG. 27 is a diagram schematically showing a region of interest set in a slice image.

The slice ID 4200 is an identifier of a slice image in which a region of interest is set and is the same as the slice ID 2200 shown in FIG. 24. The region of interest information 4300 is information indicating a position of a region of interest set in the slice image. FIG. 27 is a diagram schematically showing a region of interest set in a slice image. In the example shown in FIG. 27, the region of interest is set in a rectangular shape. Therefore, the region of interest information 4300 is constituted by four values including coordinates (xl, yt) of a top left vertex and coordinates (xr, yb) of a bottom right vertex of the region of interest. Obviously, a region of interest may have a shape other than a rectangle. In such a case, a parameter capable of uniquely specifying the region is adopted as the region of interest information 4300. For example, when the region of interest has a circular shape, center coordinates and a radius of a circle are adopted as the region of interest information 4300.

The image feature data 4400 is a feature value of a prescribed number of dimensions (in this case, N-number of dimensions) that is extracted from the region of interest as defined by the region of interest information 4300. The thumbnail image data 4500 is image data of a thumbnail image generated to be displayed in the case display region 710 based on a slice image in the DICOM format as identified by a slice ID. In this case, in the thumbnail image data 4500, pixel values of a thumbnail image are arranged in a raster scanning sequence from a top left vertex to a bottom right vertex of the thumbnail image, for example. As described earlier, a DICOM image obtained by a CT examination is a 11 bit (pixel value: −1000 to +1000) image with 512×512 pixels. In consideration thereof, in the present embodiment, in order to facilitate display of a thumbnail image, a thumbnail image with a 8 bit pixel value is created in advance by subjecting a DICOM image that is a source of the thumbnail image to a low resolution process and a gradation conversion process and is registered in the similar case data 4000. Alternatively, for example, a thumbnail image may be created by the medical information management system 200 and transmitted to the case retrieval system 300 or the case retrieval system 300 may acquire a DICOM image from the medical information management system 200 to create a thumbnail image.

The lesion distribution information 4600 is a distribution flag value (1: applicable, 0: not applicable) indicating whether or not a similar case that is an object corresponds to any of lesion distributions represented by diffuse 4610 to hematogenous 4670 determined in advance.

The definitive diagnosis (broadly categorized disease name) 4700 represents a broadly categorized disease name that is confirmed with respect to a similar case that is an object. The definitive diagnosis (broadly categorized disease name) 4700 is used when narrowing down similar cases by a broadly categorized disease name.

The definitive diagnosis (finely categorized disease name) 4800 represents a finely categorized disease name that is confirmed with respect to a similar case that is an object. The definitive diagnosis (finely categorized disease name) 4800 is used when narrowing down similar cases by a finely categorized disease name.

As for the definitive diagnosis (broadly categorized disease name) 4700, a broadly categorized disease name which uniquely corresponds to the definitive diagnosis (finely categorized disease name) 4800 is defined in advance and stored in the similar case data 4000 using the correspondence relationship.

As for the definitive diagnosis (finely categorized disease name) 4800, the series ID 2100 is identified from the slice IDs 2200 shown in FIG. 24 in the medical image data accumulating unit 203. Subsequently, the examination ID 1810 is identified by the patient information accumulating unit 201 from the identified series ID, corresponding patient information 1000 (FIG. 22) is identified from the examination ID 1810, and a definitive diagnosis 1900 of a corresponding patient is identified from the identified patient information 1000.

Next, a flow from the start of a diagnostic interpretation operation to the start of a similar case retrieval by the information terminal 100 in cooperation with the medical information management system 200 and the case retrieval system 300 will be described.

Figure 28:
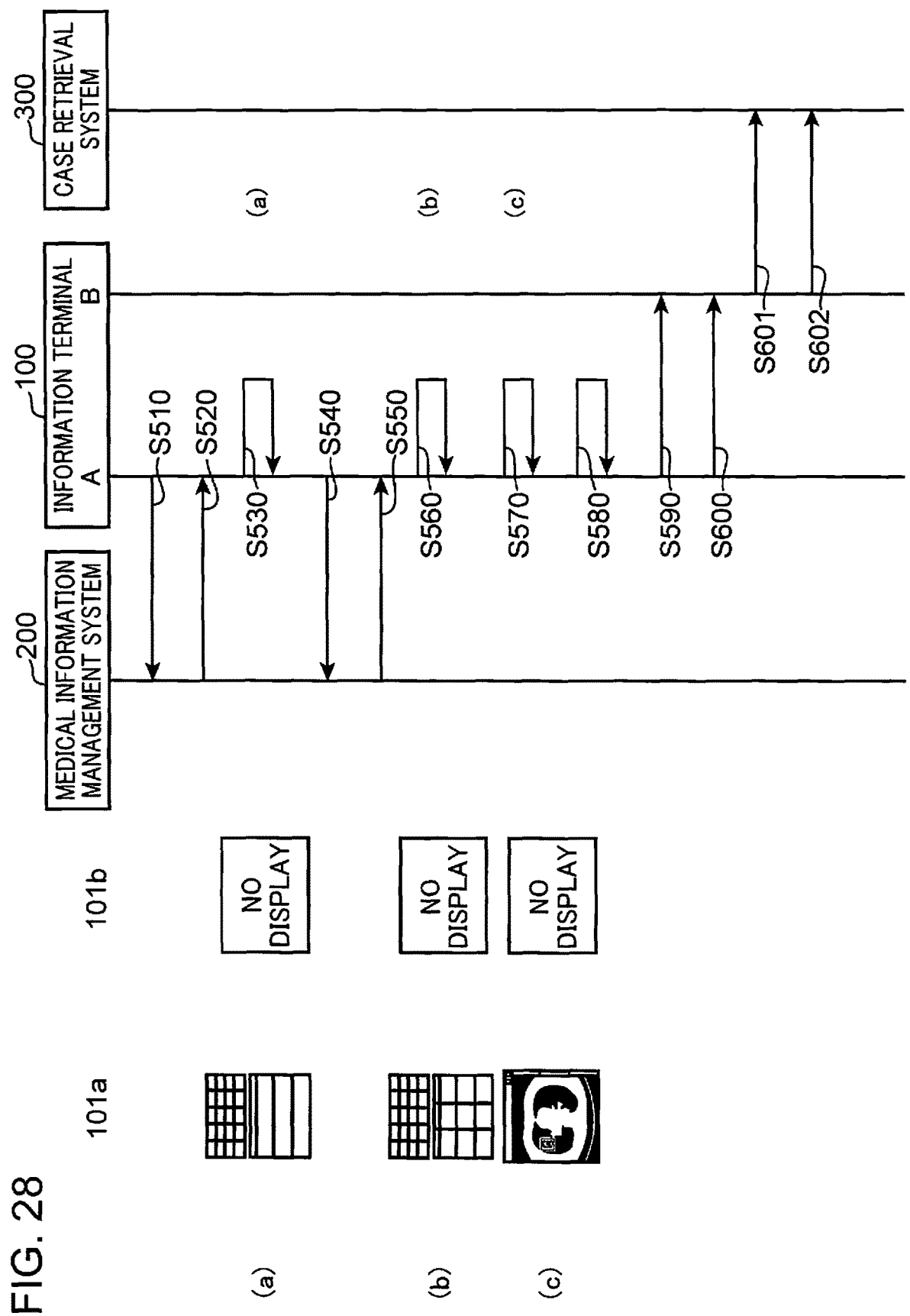
FIG. 28 is a sequence diagram showing a process in which an information terminal first acquires a diagnosis object case from a medical information management system and then issues a request for similar case retrieval to a case retrieval system, and the case retrieval system subsequently receives the request for similar case retrieval.

FIG. 28 is a sequence diagram showing a process in which the information terminal 100 first acquires a diagnosis object case from the medical information management system 200 and then issues a request for similar case retrieval to the case retrieval system 300, and the case retrieval system 300 subsequently receives the request for similar case retrieval. Moreover, in FIG. 28, two columns of rectangles shown to the left of the sequence diagram represent screens displayed on the displays 101a and 101b due to the processes of corresponding steps. In addition, in FIG. 28, "A" shown near the information terminal represents a medical information management application and "B" represents a similar case retrieval application. It is assumed that the medical information management application has been started prior to the start of the present sequence.

First, the information terminal 100 accepts a display request for an examination list to be a diagnostic interpretation object of a user (a radiologist to perform the diagnostic interpretation) through the operating unit 102, and transmits the display request for the examination list to the communication control unit 206 of the medical information management system 200 through the input control unit 103 and the communication control unit 110 (S510).

The patient information managing unit 202 of the medical information management system 200 lists examinations for which image-based examination has been performed but diagnostic interpretation has not been completed and generates a diagnostic interpretation object examination list. In addition, the patient information managing unit 202 transmits the generated examination list to the communication control unit 110 of the information terminal 100 through the communication control unit 206 (S520). In this case, the examination list includes patient information 1000 and examination information 1800 of a corresponding patient.

The display control unit 104 of the information terminal 100 displays the examination list received by the communication control unit 110 on the display 101 (S530).

In this case, the display 101a displays the examination list and the display 101b displays nothing.

FIG. 29 is a screen diagram of an examination list. The examination list includes a region 800 for displaying examinations for which diagnostic interpretation has not been completed and a region 810 for displaying information related to a series included in the examinations. Fields of a "patient ID", a "patient name", an "examination date/time", an "examination ID", and an "examination type" are provided in the region 800. The patient ID 1100 and the name 1200 registered in the patient information 1000 are displayed in the "patient ID" and "patient name" fields, and the examination date/time 1820, the examination ID 1810, and the examination type 1830, which are registered in the examination information 1800, are displayed in the "examination date/time", "examination ID", and "examination type" fields. The region 810 is a region for displaying details of an examination selected by the user in the region 800 and is provided with fields of a "series ID", a "definition", and an "image". In this case, since an examination (corresponding to rows) have not been selected by the user in the region 800, nothing is displayed in the region 810.

The user selects an examination for which diagnostic interpretation is to be performed from the examinations displayed in the region 800. When the selection is sensed by the input control unit 103, as shown in FIG. 28, the communication control unit 110 transmits a display request for all series included in the examination ID of the selected examination to the medical information management system 200 (S540).

When the communication control unit 206 of the medical information management system 200 receives the display request, the patient information managing unit 202 refers to the medical image database 2000 shown in FIG. 24, acquires all slice images of all series included in the examination ID specified by the display request, and transmits the slice images to the information terminal 100 through the communication control unit 206 (S550). For example, in the example shown in FIG. 24, when the examination with the examination ID "13227989" is selected by the user, all slice images included in the series with the series IDs "CT149123" and "CT149124" are transmitted in S550.

When the communication control unit 110 of the information terminal 100 acquires images of all series, the display control unit 104 displays a series list that displays information related to all series included in the specified examination ID as a list in the region 810 (S560).

In this case, a series list of the series corresponding to the examination selected in the region 800 is displayed in the region 810 of the examination list displayed on the display 101a. Meanwhile, nothing is displayed on the display 101b.

FIG. 30 is a screen diagram of the examination list after an examination is selected. In the region 800 shown in FIG. 30, the background of a selected row is highlighted. In the example shown in FIG. 30, an examination on "Taro Pana" in the second row is selected in the region 800. Therefore, in the region 810, the "series ID", the "definition", and the "image" of the selected examination are displayed. In this case, the series ID associated with the examination ID of the selected examination in the medical image database 2000 is displayed in the "series ID" field and a thumbnail image of one slice image representing the displayed series ID is displayed in the "image" field. As the one slice image that represents the series ID, an image at a prescribed slice position is adopted. The prescribed slice position may be a top slice position or a central slice position. The "definition" indicates a photographic condition or a reconstruction condition with respect to a corresponding series. Although not shown, for example, the "definition" is registered in association with a series ID in the medical image database 2000 shown in FIG. 24.

Figure 73C:
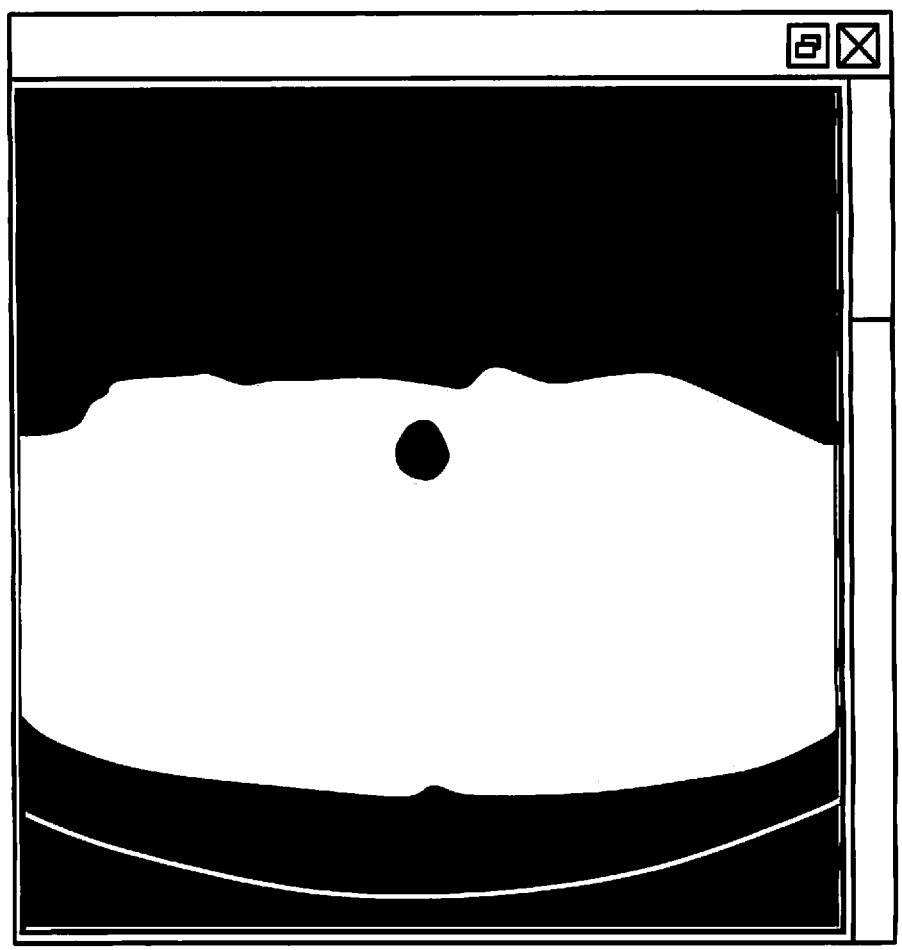
FIG. 73C is a diagram showing a slice image that is displayed on a display when a series is selected by a user.

When a diagnostic interpretation object series is selected by the user in the region 810 and the input control unit 103 senses the selection, the display control unit 104 displays a top slice image of the selected series on the display 101a as shown in FIG. 73C (S570). FIG. 73C is a diagram showing a slice image that is displayed on the display 101a when a series is selected by the user. FIG. 73C is a diagram showing a top slice of a chest CT radiograph and is a slice image taken at a shoulder position that is slightly closer to the head than the pulmonary apex. At this point, the display control unit 104 displays all slice images of the selected series on the display 101a so that the slice images can be series-fed. Meanwhile, nothing is displayed on the display 101b. For example, the user positions a mouse pointer on the display 101a and inputs a slice feeding operation by rotating a mouse wheel, whereby the input control unit 103 senses the operation. As a result, the display control unit 104 switches the slice image displayed on the display 101a to a slice image at a different slice position in accordance with an amount of rotation of the mouse wheel. The user performs image diagnosis while inputting a slice feeding operation. In addition, when the user hesitates in performing the image diagnosis, the user starts the similar case retrieval application.

At this point, the similar case retrieval application may be started when a shortcut key determined in advance is input on a keyboard of the operating unit 102 or when a menu of a medical image viewer is displayed by a right click of the mouse and a similar case retrieval menu is specified from the menu. When an instruction to start the similar case retrieval application is issued, management of the information terminal 100 is handed over to the ROI managing unit 105 and the information terminal 100 enters a region of interest (ROI) standby state.

Figure 31:
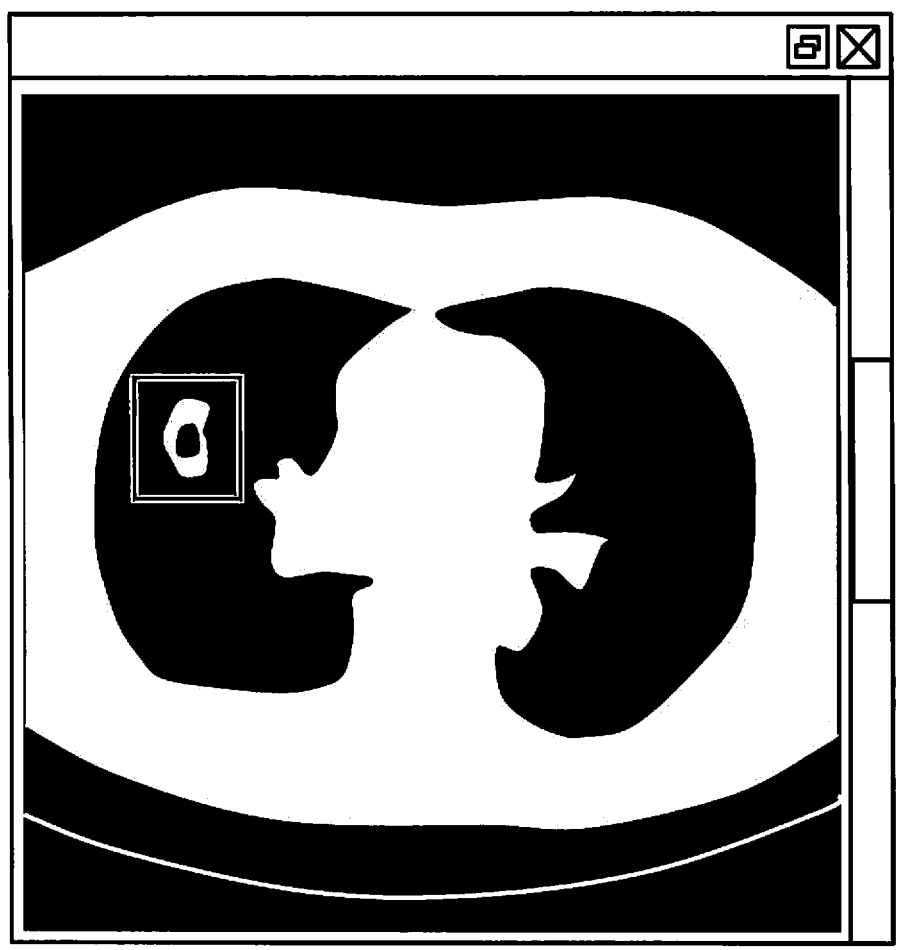
FIG. 31 shows an example of a screen after a region of interest has been set with respect to a lesion.

The user sets a region of interest (ROI) to a lesion on the slice image displayed on the display 101a through the operating unit 102 (S580). At this point, as shown in FIG. 27, for example, the user left-clicks the mouse to input coordinates of a top left vertex of the region of interest. Subsequently, the user may input a bottom right vertex of the region of interest by dragging the mouse diagonally rightward and downward while holding the left click of the mouse and then releasing the left click. FIG. 31 shows an example of a screen after a region of interest has been set with respect to a lesion.

When the input control unit 103 senses an operation for setting a region of interest, the ROI managing unit 105 receives coordinate data of the top left and bottom right vertices of the region of interest from the input control unit 103 and generates region of interest information with the received coordinate data. In addition, the ROI managing unit 105 transmits the generated region of interest information to the communication control unit 110 (S590).

At the same time, the ROI managing unit 105 transmits a slice image of the diagnosis object case to the communication control unit 110 (S600). In this case, in S550, one slice image (retrieval query image) to which a region of interest has been set by the user in a series selected by the user is transmitted among the slice images of all series received by the information terminal 100 from the medical information management system 200.

Next, the communication control unit 110 receives the region of interest information transmitted from the ROI managing unit 105 and transmits the region of interest information to the communication control unit 304 of the case retrieval system 300 (S601).

At the same time, the communication control unit 110 receives the slice image transmitted from the ROI managing unit 105 and transmits the slice image to the communication control unit 304 of the case retrieval system 300 (S602).

While a slice image itself is transmitted in S600 and S601, only a slice ID of the slice image may be transmitted instead. In this case, the case retrieval system 300 having received the slice ID may acquire a slice image from the medical information management system 200 by specifying the slice ID.

Next, a process until the case retrieval system 300 performs similar case retrieval and the information terminal 100 initially displays a similar case retrieval result will be described.

Figure 32:
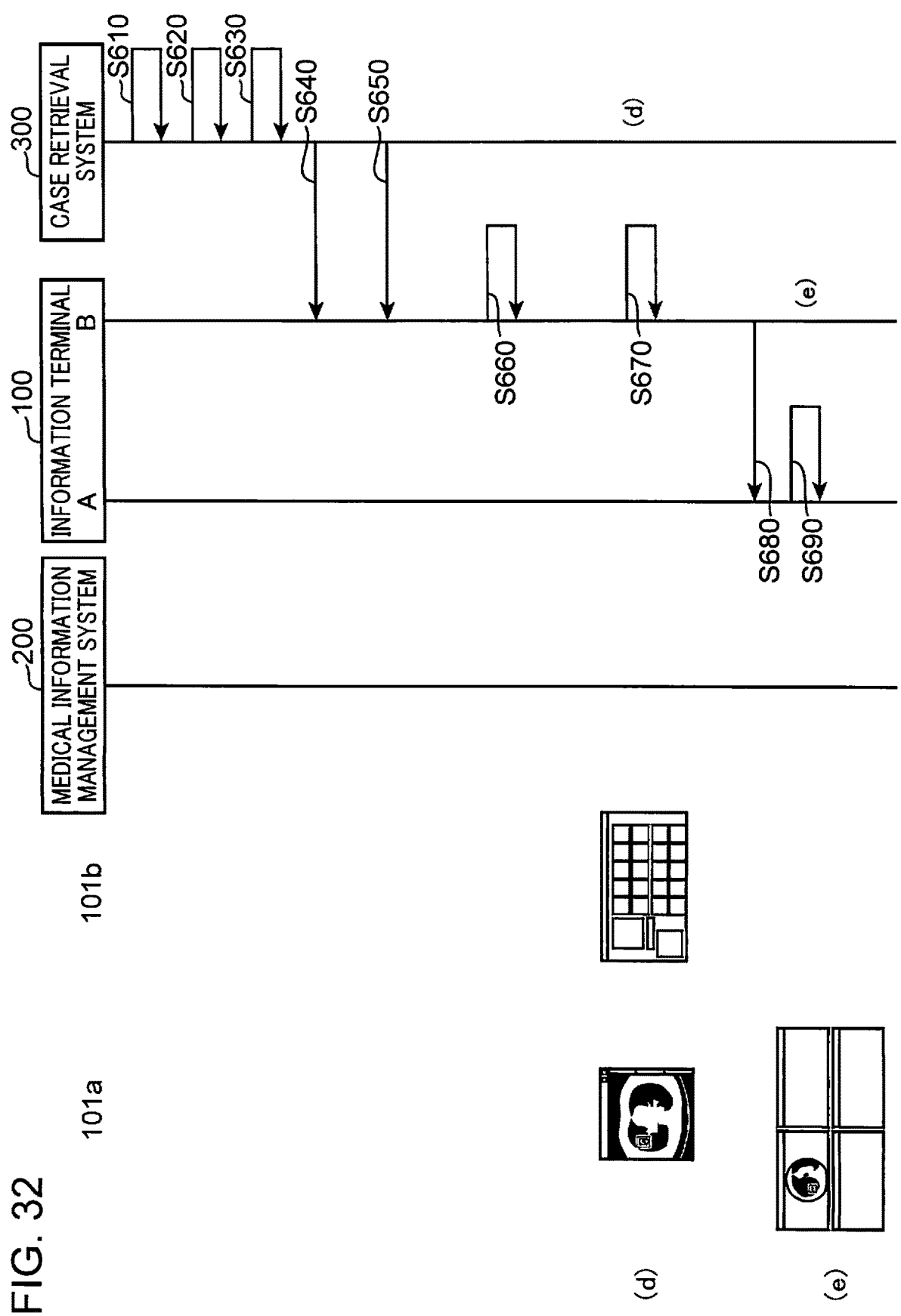
FIG. 32 is a sequence diagram showing a process in which, after a case retrieval system receives a request for similar case retrieval, the case retrieval system sends back a similar case retrieval result to an information terminal.

FIG. 32 is a sequence diagram showing a process in which, after the case retrieval system 300 receives a request for similar case retrieval, the case retrieval system 300 sends back a similar case retrieval result to the information terminal 100.

The image feature extracting unit 302 of the case retrieval system 300 extracts an image feature of a plurality of number of dimensions determined in advance from the region of interest set in the retrieval query image (S610).

As an "image feature", an image feature related to a shape of an organ or a lesion portion in a medical image, an image feature related to brightness distribution, or the like can be adopted. For example, Non Patent Literature "Nemoto, Shimizu, Hagihara, Kobatake, and Nawano; Improvement of Tumor Detection Performance in Mammograms by Feature Selection from a Large Number of Features and Proposal of Fast Feature Selection Method; IEICE TRANSACTIONS on Information and Systems D-II, Vol. 388-D-II, No. 2, pp. 416-426, February 2005" describes using an image feature with 490 dimensions. In the present embodiment, for example, the image feature described in this Non Patent Literature is adopted. However, this is simply an example and other image features may be adopted instead.

The similar case retrieving unit 303 compares the image feature extracted by the image feature extracting unit 302 and an image feature of each similar case accumulated in the similar case data accumulating unit 301 with each other (S620). At this point, the similar case retrieving unit 303 compares both image features with each other by calculating a distance between image feature data extracted from the retrieval query image and image feature data 4400 registered in the similar case data 4000 (FIG. 26) accumulated for each similar case in the similar case data accumulating unit 301.

Next, the similar case retrieving unit 303 sorts similar cases with distances that are equal to or shorter than a prescribed threshold in an ascending order of distance and decides the similar cases to be transmission objects (S630). Next, among the similar case data 4000 accumulated in the similar case data accumulating unit 301, the communication control unit 304 transmits the similar case ID 4100, the slice ID 4200, the region of interest information 4300, the thumbnail image data 4500, the lesion distribution information 4600, the definitive diagnosis (broadly categorized disease name) 4700, and the definitive diagnosis (finely categorized disease name) 4800 of a similar case decided as the transmission object as well as the distance calculated by the similar case retrieving unit 303 to the information terminal 100 (S640).

Hereinafter, a process is executed for generating an initial basic screen K2 (FIG. 6) on which a similar case retrieval result is displayed. First, management information that is used when generating the layout region 720 on the initial basic screen K2 will be described.

First, the communication control unit 304 of the case retrieval system 300 transmits layout information to the information terminal 100 (S650). In this case, layout information refers to information that specifies the number of rows and the number of columns of display boxes constituting the layout region 720.

Next, when the communication control unit 110 of the information terminal 100 receives the layout information, the display box managing unit 106 registers the number of rows and the number of columns of display boxes specified by the transmitted layout information in display box management information 4410 (FIG. 44) and, at the same time, registers the slice ID of the retrieval query image in display box management information (FIG. 44) (S660).

FIG. 44 is a diagram showing a data configuration of the display box management information 4410. The display box management information 4410 includes a table 4411 in which number of rows and the number of columns are registered and a table 4412 in which a slice ID of the slice image displayed in each display box is registered. Therefore, the display box managing unit 106 registers the number of rows and the number of columns of display boxes specified by the layout information transmitted from the case retrieval system 300 in the number of row field and the number of column field of the table 4411. In addition, in the present embodiment, a thumbnail image of the retrieval query image is displayed in a top left display box 721 among the four display boxes 721 to 724. Therefore, the display box managing unit 106 registers the slice ID of the retrieval query image transmitted from the medical information management system 200 in a 1st-row, 1st-column item of the table 4412.

In this case, default values of the number of rows and the number of columns of display boxes constituting the layout region 720 are set in advance by the case retrieval system 300. The default values of the number of rows and the number of columns are, for example, two rows and two columns. Therefore, "2 rows and 2 columns" are registered in the display box management information 4410 shown in FIG. 44.

In the example shown in FIG. 6, the display boxes 721 to 724 are displayed in two rows and two columns in the layout region 720. The number of rows and the number of columns in the layout region 720 can be set at will by the user.

Figure 41:
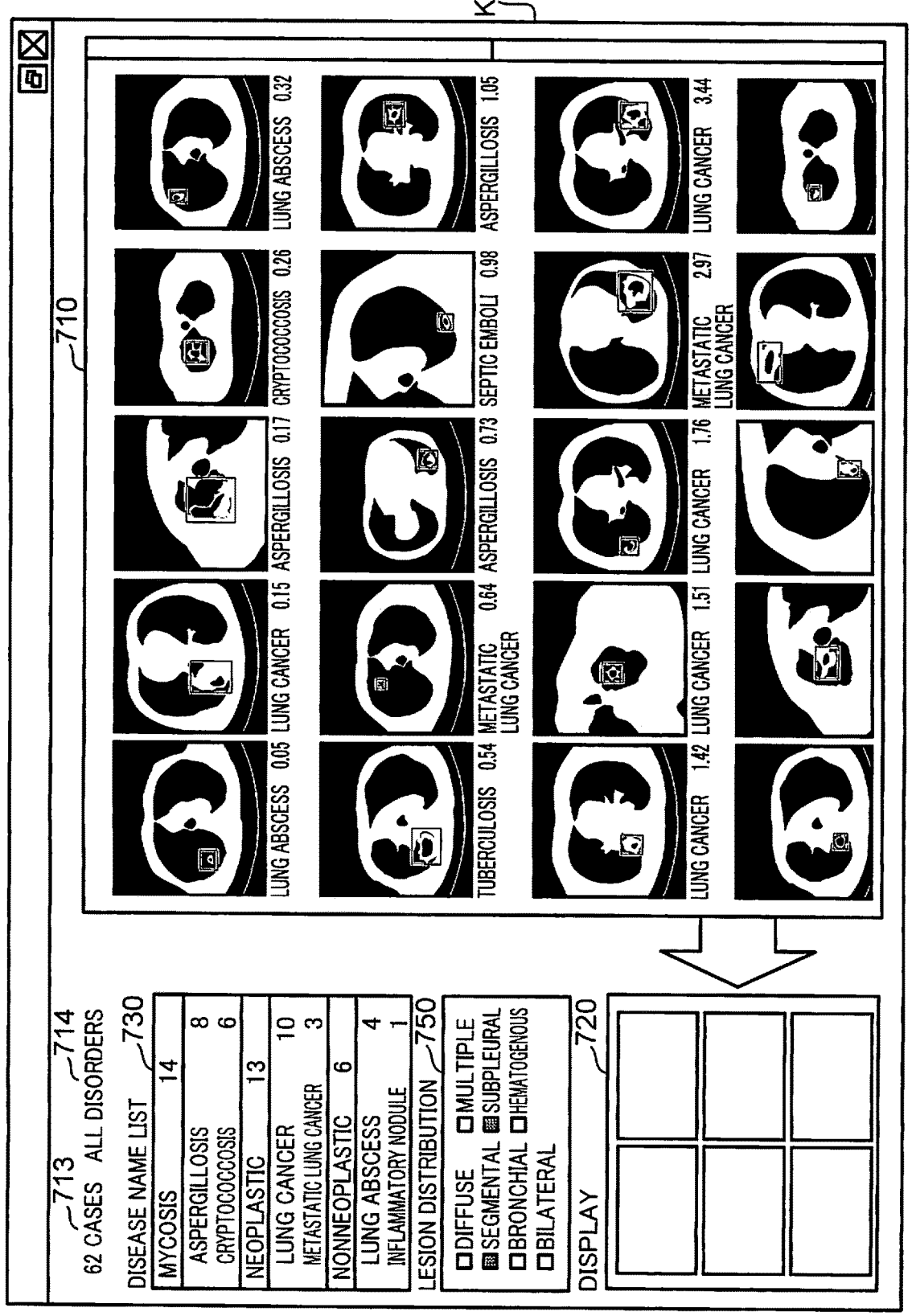
FIG. 41 is a diagram showing a basic screen having a layout region in which display boxes are set in three rows and two columns.

FIG. 41 is a diagram showing the basic screen K2 having the layout region 720 in which display boxes are set in three rows and two columns. If the display boxes constituting the layout region 720 are to be generalized as M rows and N columns, when M≠N, it is desirable that M>N when the display 101 is an upright display and desirable that M<N when the display 101 is a horizontal display.

An important feature of the present embodiment is that a thumbnail image of a diagnosis object case is displayed in one display box among the display boxes constituting the layout region 720. In other words, by displaying a similar case and a diagnosis object case adjacent to each other, the user can more easily determine the degree of similarity between both cases. Therefore, the arrangement of the display boxes in the layout region 720 is desirably set to three rows and three columns at the most.

In addition, when the arrangement of the display boxes is three rows and two columns, the thumbnail image of the retrieval query image is favorably displayed in the 2nd-row, 1st-column display box or the 2nd-row, 2nd-column display box. Furthermore, when the arrangement of the display boxes is two rows and three columns, the thumbnail image of the retrieval query image is favorably displayed in the 1st-row, 2nd-column display box or the 2nd-row, 2nd-column display box. Moreover, when the arrangement of the display boxes is three rows and three columns, the thumbnail image of the retrieval query image is favorably displayed in the 2nd-row, 2nd-column display box. Accordingly, the similar case is to be always displayed adjacent to the diagnosis object case in the layout region 720.

Layout information of the layout region 720 set by the user is registered in layout management information 4200 shown in FIG. 42 or 43.

Moreover, the box layout managing unit 111 that stores the layout management information 4200 may be included in the case retrieval system 300.

Even for the same user, a layout of the layout region 720 may be changed so as to accommodate a size or a screen type (upright or horizontal) of the display 101 of the information terminal 100. Therefore, as shown in FIG. 43, the layout information set by the user may be registered in the layout management information 4200 in association with a user ID and a terminal ID. FIG. 43 is a diagram showing an example of the layout management information 4200. In the layout management information 4200, a "user ID", a "terminal ID", the "number of columns", the "number of rows", and a "position of diagnosis object case" are associated with each other. In this case, the "user ID" is an identifier that is assigned to a user who uses the information terminal 100 in advance. The "terminal ID" is an identifier of the information terminal 100 that is expected to be used by a corresponding user.

In the example shown in FIG. 43, since the user with a user ID "U01" is expected to use terminal IDs "T02" and "T04", the user ID "U01" is associated with the terminal IDs "T02" and "T04". The number of rows and the number of columns of the layout region 720 as set by a corresponding user are registered in the "number of columns" and the "number of rows". The "position of diagnosis object case" represents a position of a display box that displays the diagnosis object case. For example, in the information terminal 100 with the terminal ID "T04", the layout region 720 is set to two rows and three columns, and (2,1) indicating the 2nd row and 1st column is registered as the "position of diagnosis object case" so that the diagnosis object case is displayed adjacent to all of the similar cases.

Moreover, while a mode in which layout information is managed in association with a user ID and a terminal ID has been shown in FIG. 43, layout information may be managed in association with only a user ID. FIG. 42 is a diagram showing an example of the layout management information 4200. In the layout management information 4200 shown in FIG. 42, the "terminal ID" field has been omitted from the layout management information 4200 shown in FIG. 43. Otherwise, the layout management information 4200 shown in FIG. 42 is the same as the layout management information 4200 shown in FIG. 43. Moreover, in the mode shown in FIG. 42, since one user had been expected to use one information terminal 100, the "terminal ID" field is omitted.

When layout information is managed by the case retrieval system 300, layout information of a corresponding user is transmitted to the information terminal 100 in S650 in FIG. 32.

Next, using the similar case data transmitted in S640 and the display box management information 4410 stored in S660, the display control unit 104 generates the initial basic screen K2 on which a similar case retrieval result is displayed (S670).

In this case, the basic screen K2 shown in FIG. 6 is displayed on the display 101b. In addition, the retrieval query image is displayed on the display 101a.

Figure 33:
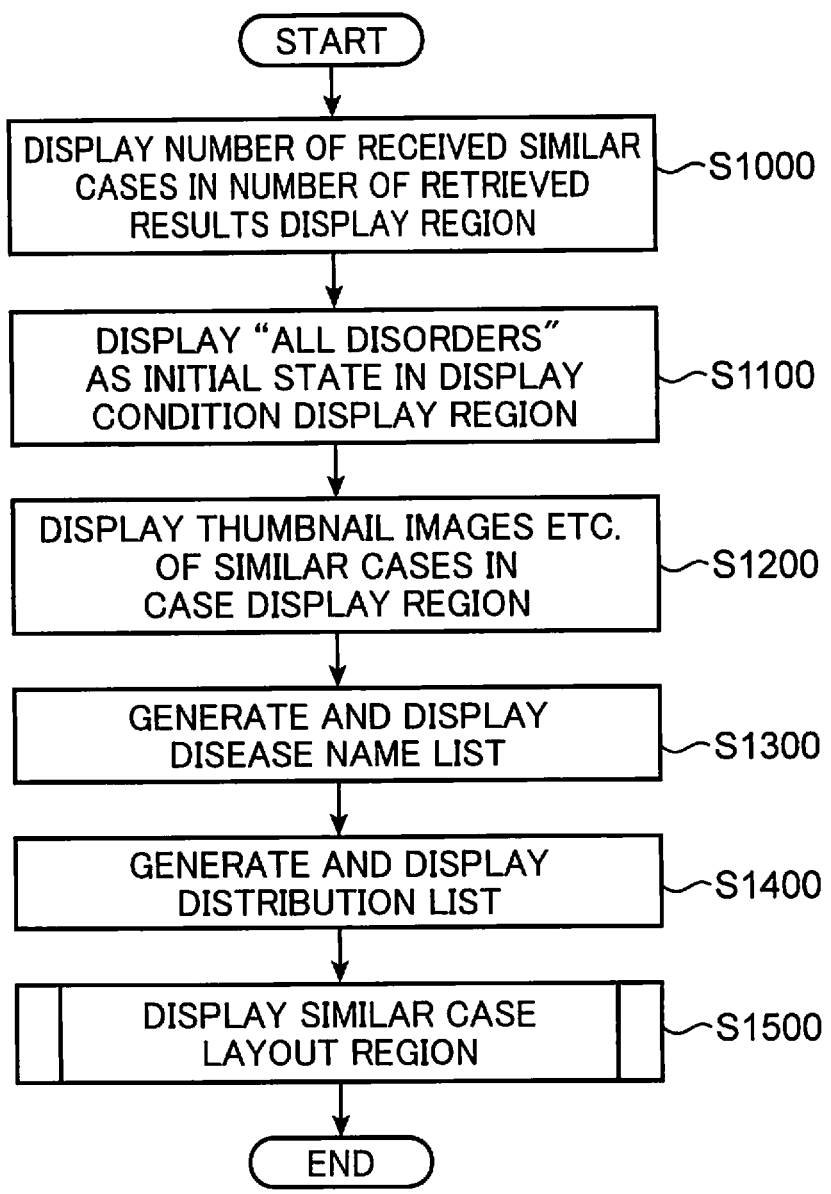
FIG. 33 is a flow chart showing details of a process for generating an initial basic screen shown in S670 in FIG. 32.

FIG. 33 is a flow chart showing details of the process for generating the initial basic screen K2 shown in S670 in FIG. 32.

First, in S1000, the display control unit 104 counts the number of similar cases received in S640 shown in FIG. 32 and displays the count value in the number of retrieved results display region 713.

Next, in S1100, the display control unit 104 displays "all disorders" in the display condition display region 714. "All disorders" is displayed at this point because, on the initial basic screen K2, similar cases have not yet been narrowed down by a disease name or a lesion distribution by the user.

Next, in S1200, the display control unit 104 displays thumbnail images of similar cases in the case display region 710 for the number of similar cases for which thumbnail images can be displayed in the case display region 710 among the similar cases received in S640 shown in FIG. 32 and, at the same time, displays a definitive diagnosis and a degree of similarity in association with each thumbnail image.

In the example shown in FIG. 6, the maximum value of the number of similar cases that can be displayed in the case display region 710 is 20. This maximum value is determined in advance. Alternatively, a configuration may be adopted in which the user can change the maximum value at will. When the number of similar cases received in S640 shown in FIG. 32 is larger than the maximum value, the display control unit 104 displays the scroll bar 715 that is elongated in a vertical direction at a right end of the case display region 710. Accordingly, the user can move the scroll bar 715 and view thumbnail images of similar cases which had been hidden on the initial basic screen K2.

Next, in S1300, a disease name list is generated and displayed. First, a disease name list is generated from the similar cases received in S640 shown in FIG. 32. The disease name list is a list in which the similar cases received in S640 are classified according to definitively diagnosed disease names.

Let us assume that the number of similar cases received in S640 is expressed as NC. The disease name list managing unit 108 generates the disease name list using the definitive diagnosis (broadly categorized disease name) 4700 and the definitive diagnosis (finely categorized disease name) 4800 respectively registered in the NC-number of pieces of similar case data 4000. The generated disease name list is managed by the disease name list managing unit 108 as table format data as shown in FIG. 35.

FIG. 35 is a diagram showing a data configuration of a disease name list that is generated in S1300 shown in FIG. 33. The disease name list includes fields of a "disease name ID", a "broadly categorized disease name", a "finely categorized disease name", the "number of cases", and a "similar case ID". The "disease name ID" is an identifier assigned to each definitively diagnosed disease name. In this case, one disease name ID is assigned to one combination of a broadly categorized disease name and a finely categorized disease name.

The "broadly categorized disease name" is the definitively diagnosed disease name represented by the definitive diagnosis (broadly categorized disease name) 4700 registered in the similar case data 4000. The "finely categorized disease name" is the definitively diagnosed disease name represented by the definitive diagnosis (finely categorized disease name) 4800 registered in the similar case data 4000. The "number of cases" is the number of similar cases corresponding to the definitively diagnosed disease name represented by the "disease name ID". The "similar case ID" is a similar case ID representing a similar case corresponding to the disease name represented by the "disease name ID".

The disease name list managing unit 108 extracts the definitive diagnosis (broadly categorized disease name) 4700 and the definitive diagnosis (finely categorized disease name) 4800 for all pieces of similar case data 4000 received in S640 and classifies the same similar case data 4000 as the similar case of a same definitively diagnosed disease name for both definitive diagnoses. In addition, the disease name list managing unit 108 counts the number of similar cases with the same definitively diagnosed disease name and registers the number of similar cases in the "number of cases" field in a record of a corresponding definitively diagnosed disease name. Furthermore, the disease name list managing unit 108 registers a similar case ID of a similar case classified as a same definitively diagnosed disease name in the "similar case ID" field in a record of a corresponding definitively diagnosed disease name.

In the example shown in FIG. 35, a disease name ID "DIS528" is assigned to a definitively diagnosed disease name whose broadly categorized disease name is "neoplastic" and whose finely categorized disease name is "lung cancer". In addition, since the number of similar cases corresponding to the definitively diagnosed disease name is 10, 10 is registered in the "number of cases" field of a corresponding record and similar case IDs "SIM258", "SIM551", "SIM1209", "SIM2341", and the like of similar cases corresponding to the definitively diagnosed disease name are registered in the "similar case ID" field of the corresponding record.

Subsequently, the display control unit 104 generates the disease name list display region 730 using the disease name list generated as described above and displays the disease name list display region 730 on the display 101.

Figure 37:
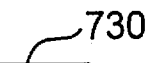
FIG. 37 is a diagram showing a second display example of a disease name list display region.

FIGS. 36, 37, and 38 are, respectively, diagrams showing a first display example, a second display example, and a third display example of the disease name list display region 730. As shown in FIG. 36, in the first display example, similar cases obtained as a result of a similar case retrieval are displayed associated with the number of cases of a finely categorized disease name in a descending order of the number of cases as a list.

As shown in FIG. 37, in the second display example, similar cases obtained as a result of a similar case retrieval are displayed associated with the number of cases of a broadly categorized disease name in a descending order of the number of cases as a list.

As shown in FIG. 38, in the third display example, similar cases obtained as a result of a similar case retrieval are displayed associated with the number of cases of a broadly categorized disease name in a descending order of the number of cases as a list and, for each broadly categorized disease name, the finely categorized disease names included in the broadly categorized disease name are displayed associated with the number of cases in a descending order of the number of cases as a list. In this case, a definitively diagnosed disease name is expressed by a hierarchical structure of a broadly categorized disease name and a finely categorized disease name.

FIG. 39 is a diagram showing a screen transition of the disease name list display region 730 shown in FIG. 37. As shown in an upper part of FIG. 39, when the input control unit 103 senses an operation by a user for selecting one broadly categorized disease name among the broadly categorized disease names displayed as a list, the display control unit 104 displays the finely categorized disease names belonging to the selected broadly categorized disease name in association with the number of cases in a descending order of the number of cases as shown in a lower part of FIG. 39. At this point, for example, the user may select one broadly categorized disease name by double-clicking or single-clicking one desired broadly categorized disease name among the broadly categorized disease names displayed as a list in the disease name list display region 730. In the example shown in FIG. 39, since nonneoplastic has been double-clicked, the finely categorized disease names belonging to nonneoplastic are displayed as a list.

In the lower part of FIG. 39, when a region in which the finely categorized disease names are displayed as a list is double-clicked or single-clicked by the user, the display control unit 104 may hide the finely categorized disease names that had been displayed in the corresponding region.

Moreover, the display control unit 104 may judge the finely categorized disease names belonging to the broadly categorized disease name by referring to the disease name list (FIG. 35). For example, in the example shown in FIG. 35, since aspergillosis and cryptococcosis are associated with mycosis, the display control unit 104 may determine that aspergillosis and cryptococcosis belong to mycosis.

Returning now to FIG. 33, in S1400, a distribution list is generated and displayed. First, a distribution list is generated from the similar cases received in S640. The distribution list is a list in which the similar cases received in S640 are classified according to lesion distributions.

The disease name list managing unit 108 generates a distribution list using lesion distribution information 4600 registered in each similar case data 4000 of the NC-number of cases. The generated distribution list is managed by the distribution list managing unit 109 as table format data as shown in FIG. 40.

FIG. 40 is a diagram showing a data configuration of a distribution list that is generated in S1400 shown in FIG. 33. The disease name list includes fields of a "distribution name", the "number of cases", and a "similar case ID". The "distribution name" is a name of plurality of lesion distributions determined in advance such as diffuse and segmental. The "number of cases" represents the number of similar cases corresponding to a lesion distribution. The "similar case ID" is a similar case ID representing a similar case corresponding to a lesion distribution.

The distribution list managing unit 109 extracts lesion distribution information 4600 for all pieces of similar case data 4000 received in S640, counts the number of lesion distributions for which 1 (applicable) is set to the distribution flag value in the extracted lesion distribution information 4600, and registers the count value in the "number of cases" field of a record of a corresponding lesion distribution. In addition, the distribution list managing unit 109 registers a similar case ID of a similar case for which 1 is set to the distribution flag value in the "similar case ID" field in the record of a corresponding lesion distribution.

In the example shown in FIG. 40, since there are three similar cases corresponding to diffuse, 3 is registered in the "number of cases" of the record of diffuse. In addition, similar case IDs "SIM2521", "SIM4123", and "SIM5225" representing similar cases corresponding to diffuse are registered in the "similar case ID" field of the record of diffuse.

Subsequently, the display control unit 104 generates the distribution list display region 750 using the distribution list generated as described above and displays the distribution list display region 750 on the display 101.

FIG. 11 shows the distribution list display region 750 generated using the distribution list shown in FIG. 40. In FIG. 40, since the numbers of cases of segmental and subpleural are zero, in FIG. 11, segmental 752 and subpleural 756 are displayed in an inactive state and since other lesion distributions have one or more cases, the other lesion distributions are displayed in an active state.

Returning now to FIG. 33, in S1500, the layout region 720 is displayed. This process is performed by the display control unit 104.

Figure 34:
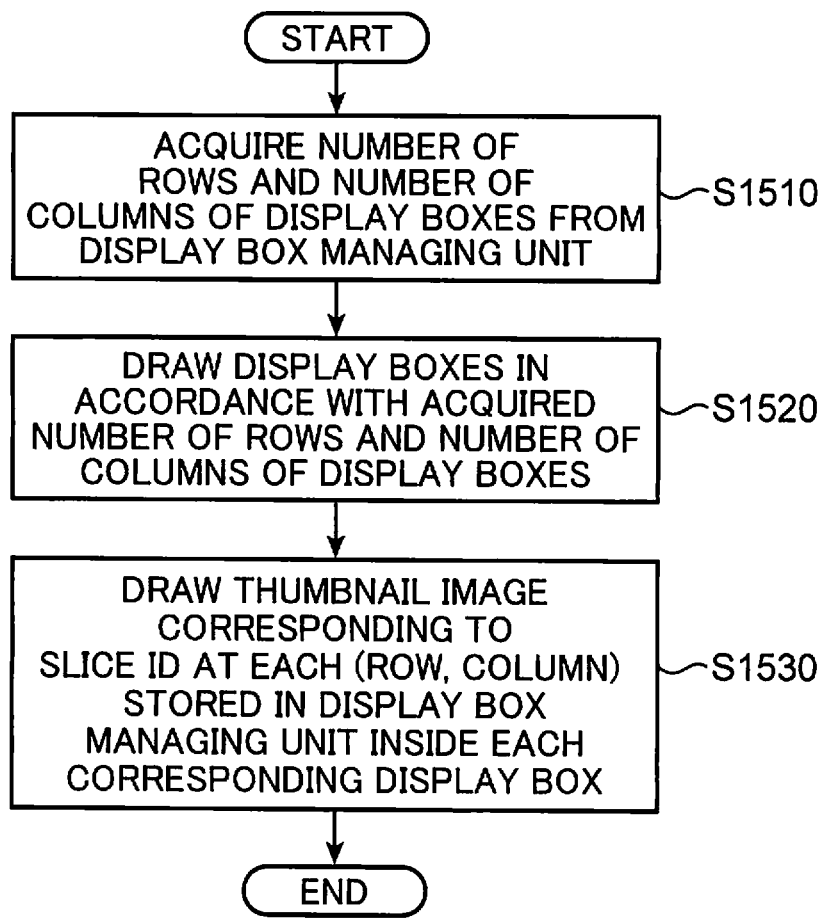
FIG. 34 is a flow chart showing a process of S1500 shown in FIG. 33.

FIG. 34 is a flow chart showing a process of S1500 shown in FIG. 33. In S1510, the display control unit 104 acquires the number of rows and the number of columns of display boxes constituting the layout region 720 from the display box management information 4410 set in S660. In the example of the display box management information 4410 shown in FIG. 44, since two rows and two columns are set as the number of rows and the number of columns, information reading "2 rows and 2 columns" is acquired. Moreover, when the user has changed the number of rows and the number of columns of display boxes, the number of rows and the number of columns of display boxes constituting the layout region 720 are acquired from the layout management information 4200 shown in FIG. 42 or 43.

Next, in S1520, the display control unit 104 draws display boxes in accordance with the number of rows and the number of columns of display boxes acquired in S1510.

Finally, in S1530, the display control unit 104 identifies a slice ID of each display box from the display box management information 4410 and draws a thumbnail image corresponding to the identified slice ID in each corresponding display box.

In the example shown in FIG. 44, the slice ID of a diagnosis object case is stored in the 1st-row, 1st-column display box. Therefore, the display control unit 104 generates a thumbnail image from the slice ID of the diagnosis object case transmitted in S600 shown in FIG. 28 and draws the generated thumbnail image in the display box 721.

At this stage, since slice IDs are not stored in the remaining display boxes (the 1st-row, 2nd-column display box 722, the 2nd-row, 1st-column display box 723, and the 2nd-row, 2nd-column display box 724), the display control unit 104 does not display anything in these display boxes. A thumbnail image of a similar case is to be displayed in these display boxes by a process to be described later.

Returning now to FIG. 32, the communication control unit 110 transmits the display box management information 4410 stored in the display box managing unit 106 to the display control unit 104 (S680).

Next, the display control unit 104 starts a medical image viewer in a same display state and a same layout as a display state and a layout of the layout region 720 (S690).

Figure 45:
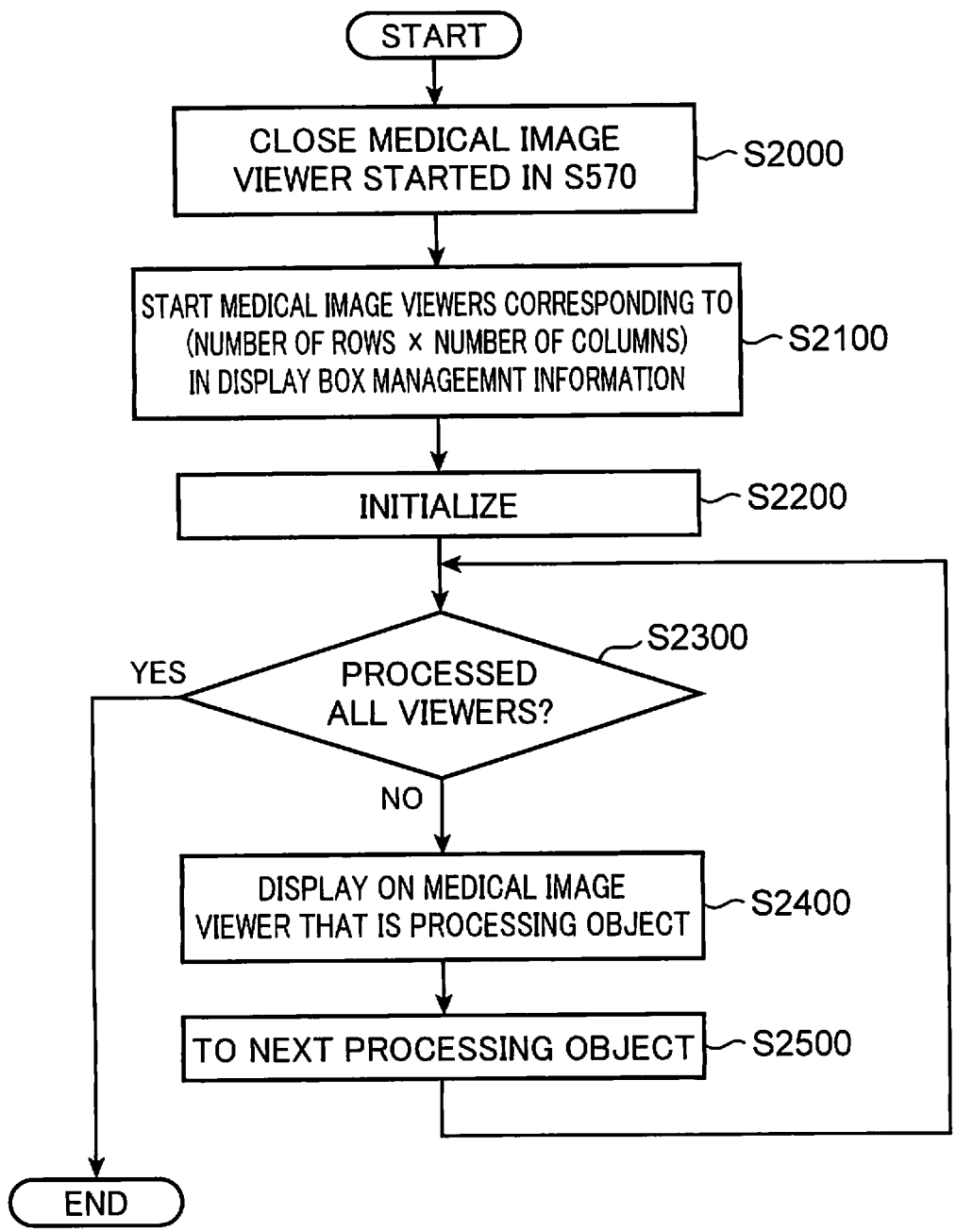
FIG. 45 is a flow chart showing a starting process of a medical image viewer.

FIG. 45 is a flow chart showing a starting process of a medical image viewer.

In S2000, the display control unit 104 closes the medical image viewer started in S570 in FIG. 28.

In S2100, the display control unit 104 starts medical image viewers corresponding to the number of display boxes registered in the display box management information 4410 in a layout with the number of rows and the number of columns registered in the display box management information 4410. In the display box management information 4410 shown in FIG. 44, four display boxes are registered in two rows and two columns. Therefore, as shown in FIG. 5, the display control unit 104 starts the four medical image viewers 610 to 640 in two rows and two columns. Moreover, when the number of rows and the number of columns of the layout region 720 is changed by the user, the medical image viewers corresponding to the number of display boxes registered in the layout management information 4200 shown in FIG. 42 or 43 are started in a layout with the number of rows and the number of columns registered in the layout management information 4200.

In S2200, the display control unit 104 initializes a variable for identifying a medical image viewer that is a processing object. In this case, since the 1st-row, 1st-column medical image viewer is the processing object, the variable is set to the 1st-row and 1st-column.

In S2300, the display control unit 104 checks whether or not processing of all (in this case, four) medical image viewers has been completed. If processed (YES in S2300), the process is completed, and if there is an unprocessed medical image viewer (NO in S2300), the process is advanced to S2400.

In S2400, the display control unit 104 displays a slice image having a slice ID associated with the number of rows and the number of columns set as a variable on the medical image viewer that is the processing object and associates a series including the slice ID with the medical image viewer.

For example, in the example of the display box management information 4410 shown in FIG. 44, a slice ID "CT12353515" is registered in the 1st-row, 1st-column. Therefore, the slice ID "CT12353515" is displayed on the medical image viewer 610. In addition, the display control unit 104 draws a rectangle representing a region of interest set in the initially displayed slice image so as to overlap with the slice image. The series including the slice ID registered in the 1st-row, 1st-column has already been acquired in S550 in FIG. 28. Furthermore, the region of interest has already been acquired in S580 in FIG. 28.

Returning now to FIG. 45, in S2500, a next medical image viewer is set as the medical image viewer that is a processing object. Processing objects are set so that, for example, the 1st-row, 1st-column is followed by the 1st-row, 2nd-column, which in turn is followed by the 2nd-row, 1st-column, which in turn is followed by the 2nd-row, 2nd-column, and so on.

In S2400 of a second loop, while the medical image viewer 620 of the 1st-row, 2nd-column becomes the processing object, a slice ID is not associated with a medical image viewer other than that of the 1st-row, 1st-column in the display box management information 4410 shown in FIG. 44. Therefore, the display control unit 104 does not execute any process on the 1st-row, 2nd-column medical image viewer and leaves the medical image viewer in a blank state. The same applies to the 2nd-row, 1st-column medical image viewer 630 and the 2nd-row, 2nd-column medical image viewer 640.

Upon conclusion of the flow chart, the initial-state basic screen K1 shown in FIG. 5 is displayed on the display 101a. On the 1st-row, 1st-column (top left) medical image viewer 610, the retrieval query image is displayed and a region of interest is drawn on top of the retrieval query image so as to overlap with the retrieval query image.

Figure 46:
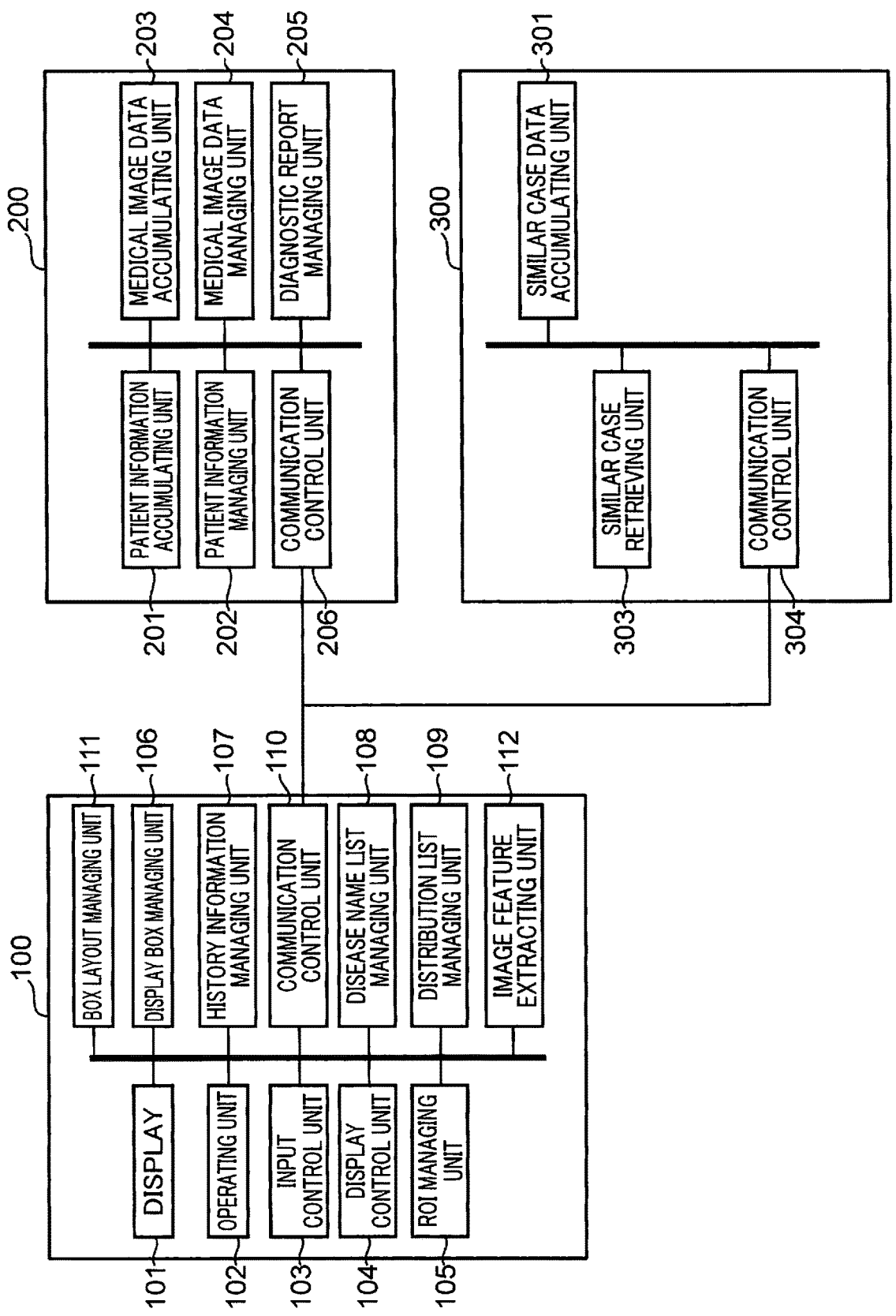
FIG. 46 is a block diagram of an information terminal, a medical information management system, and a case retrieval system when a mode is adopted in which the case retrieval system extracts an image feature.

While an example in which the case retrieval system 300 extracts an image feature has been shown, alternatively, the information terminal 100 may extract an image feature. FIG. 46 is a block diagram of the information terminal 100, the medical information management system 200, and the case retrieval system 300 when a mode is adopted in which the case retrieval system 300 extracts an image feature.

Differences from FIG. 2 are that the image feature extracting unit 112 has been added to the information terminal 100 and that the image feature extracting unit 302 has been omitted from the case retrieval system 300.

Figure 47:
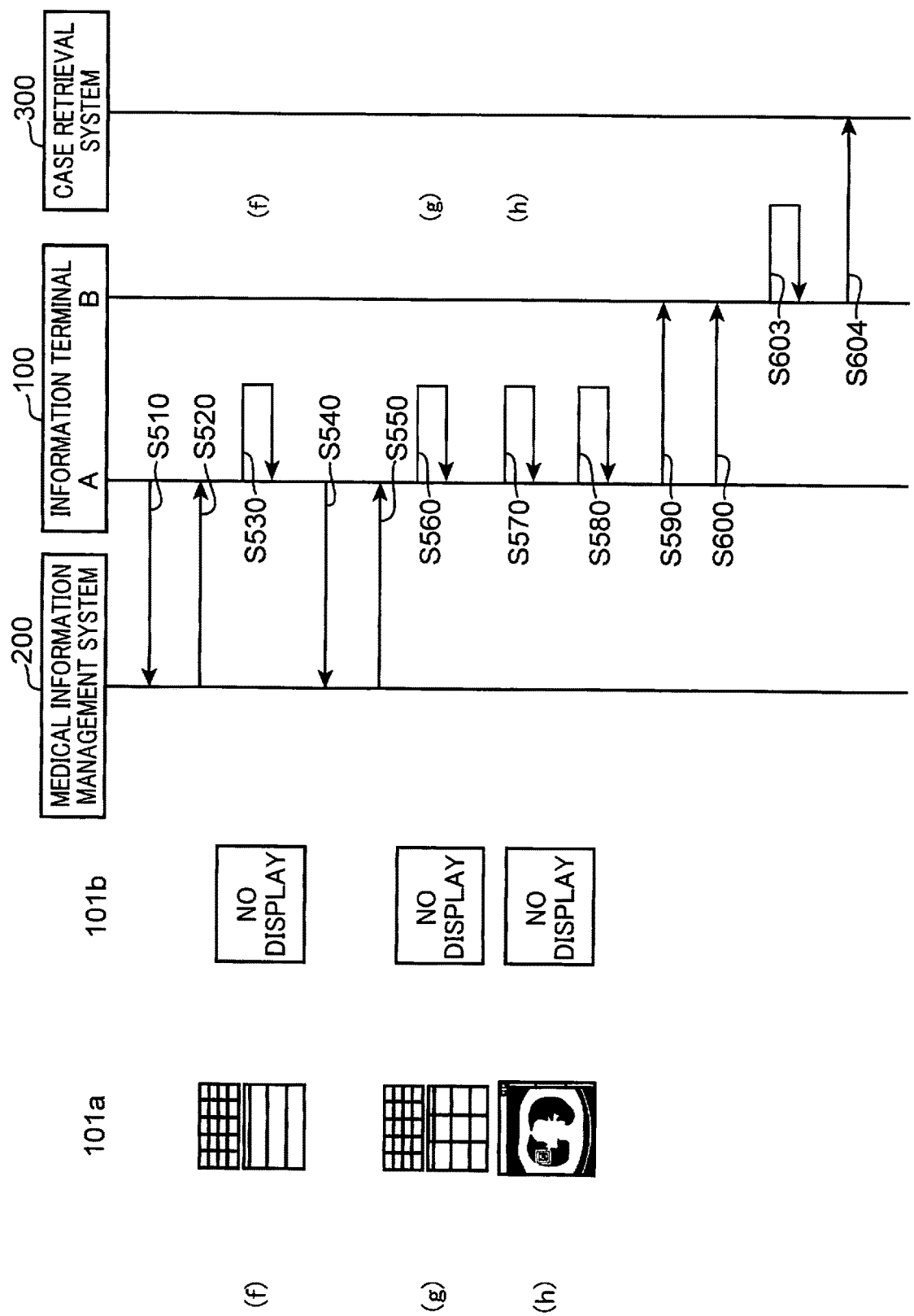
FIG. 47 is a sequence diagram showing a process in which, after an information terminal acquires a diagnosis object case from a medical information management system, a case retrieval system receives a request for similar case retrieval.

FIG. 47 is a sequence diagram showing a process in which, after the information terminal 100 acquires a diagnosis object case from the medical information management system 200, the case retrieval system 300 receives a request for similar case retrieval.

Differences from FIG. 28 are that, after a process by the ROI managing unit 105 for transmitting a slice image of a diagnosis object case to the communication control unit 110 (S600), extraction of an image feature is performed by the information terminal 100 (S603) and the extracted image feature is transmitted to the case retrieval system 300 (S604). The process content of image feature extraction (S604) is similar to the image feature extraction performed by the case retrieval system 300.

Figure 48:
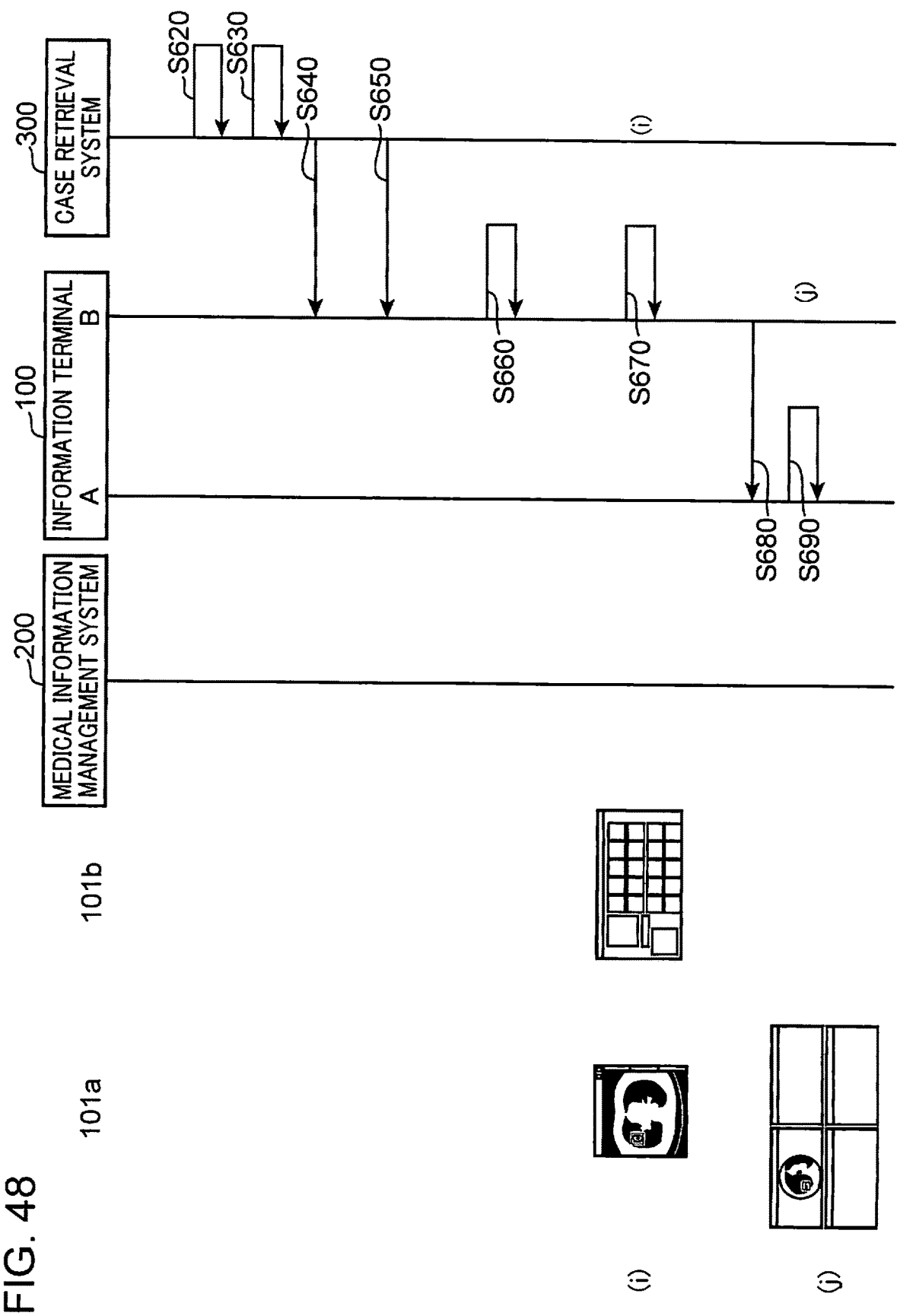
FIG. 48 is a sequence diagram showing a process in which, after a case retrieval system receives a request for similar case retrieval, the case retrieval system sends back a similar case retrieval result to an information terminal.

FIG. 48 is a sequence diagram showing a process in which, after the case retrieval system 300 receives a request for similar case retrieval, the case retrieval system 300 sends back a similar case retrieval result to the information terminal 100. A difference from FIG. 32 is that, since image feature extraction is performed by the information terminal 100, the image feature extraction (S610) included in FIG. 32 has been omitted in FIG. 48.

Next, a process that is performed when a thumbnail image of a similar case is dragged and dropped on the information terminal 100 will be described.

Figure 49:
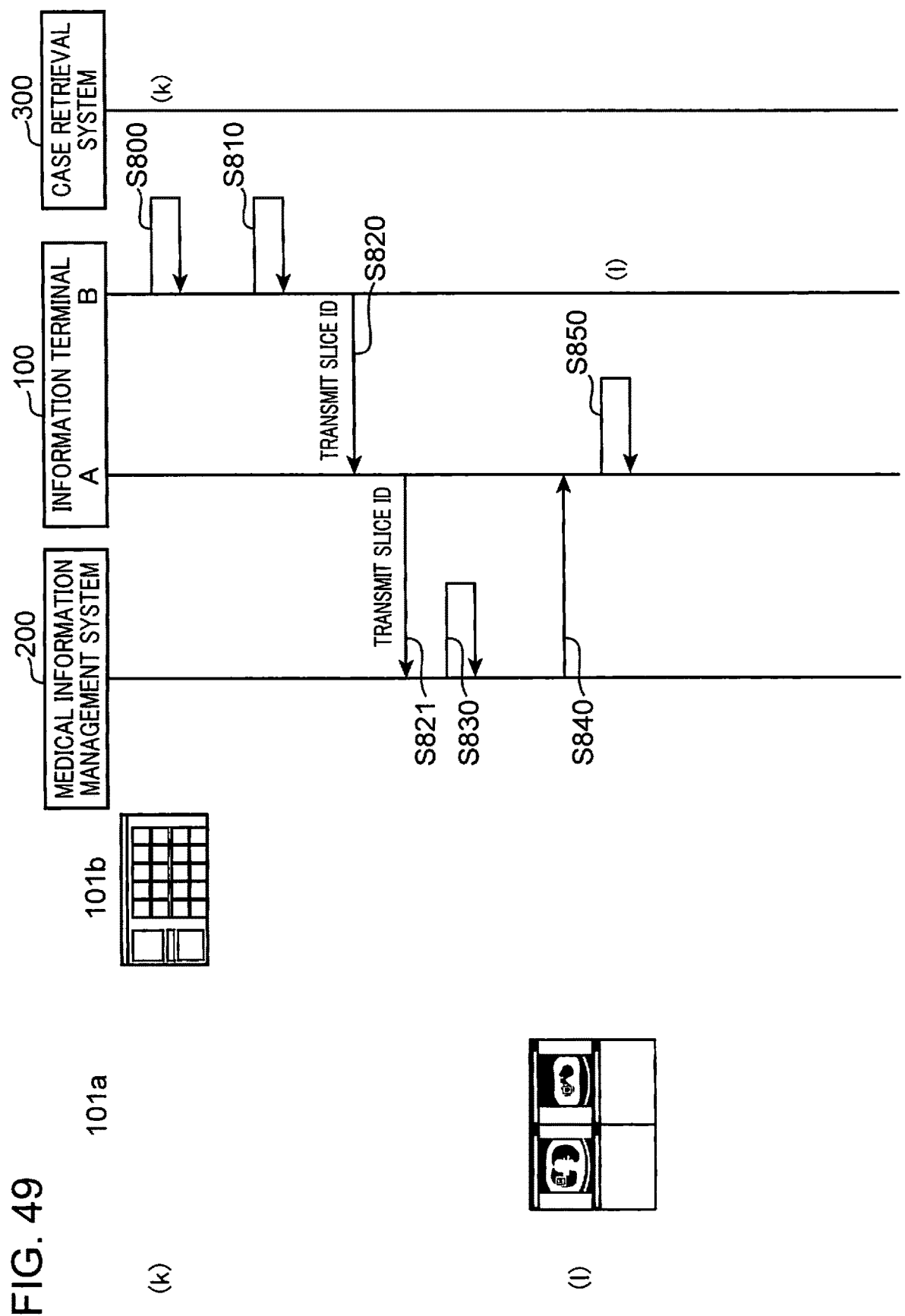
FIG. 49 is a sequence diagram showing a process when a thumbnail image of a similar case is dragged and dropped on an information terminal.

FIG. 49 is a sequence diagram showing a process when a thumbnail image of a similar case is dragged and dropped on the information terminal 100.

Figure 50:
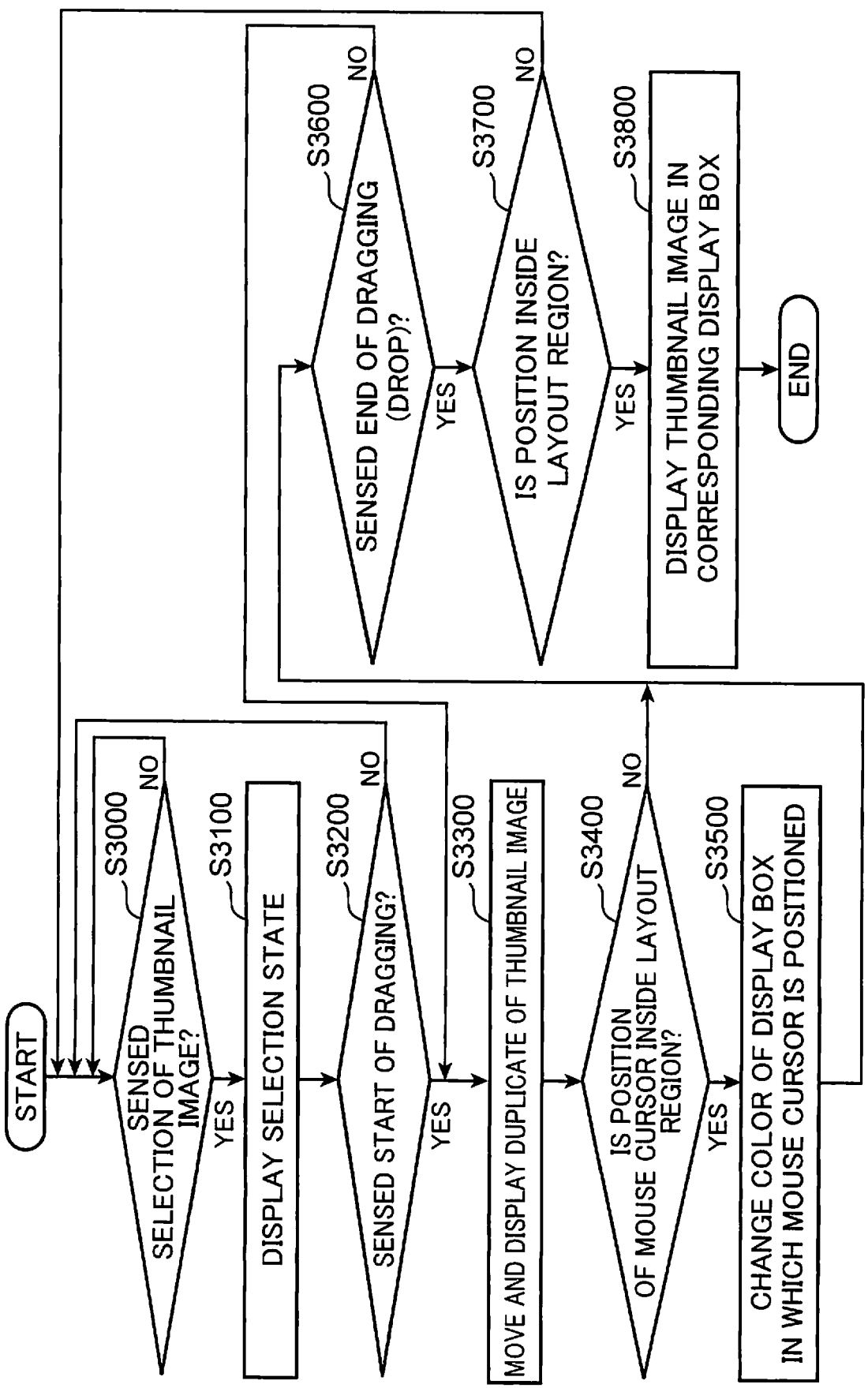
FIG. 50 is a flow chart showing details of a process of S800 shown in FIG. 49.

In S800, the input control unit 103 senses a movement of a thumbnail image of a similar case to a display box. FIG. 50 is a flow chart showing details of the process of S800 shown in FIG. 49.

Figure 51:
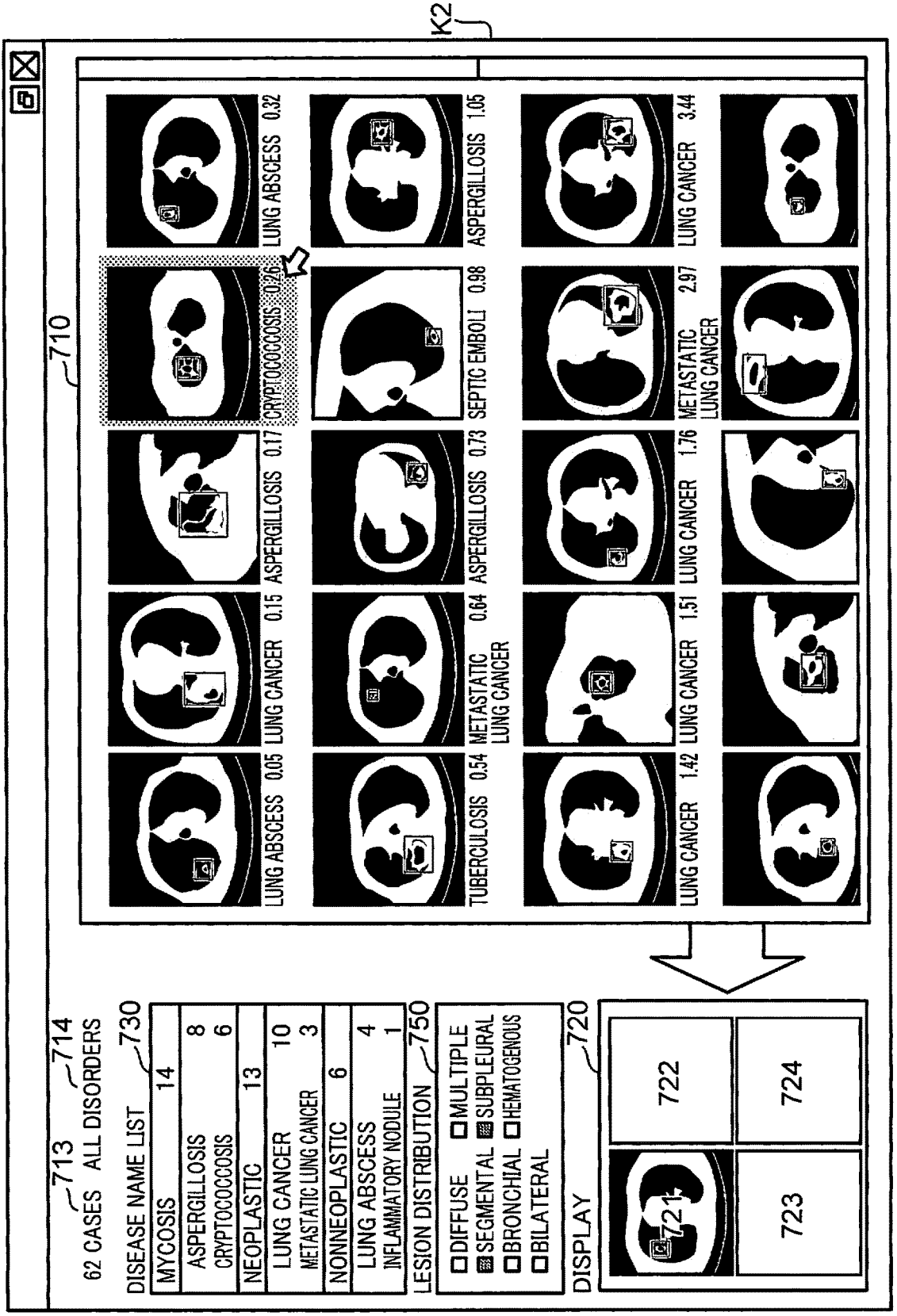
FIG. 51 is a diagram showing a basic screen when one thumbnail image among thumbnail images displayed in a case display region is selected.

The input control unit 103 of the information terminal 100 constantly monitors input made via the operating unit 102 that is a mouse or the like. In addition, when the input control unit 103 senses that an operation for clicking the mouse is input by the user and the operation causes one thumbnail image of a similar case displayed in the case display region 710 to be selected (YES in S3000), the display control unit 104 changes a color of a background of the selected thumbnail image (S3100). On the other hand, when the input control unit 103 does not sense that a thumbnail image has been selected (NO in S3000), the process is returned to 53000. FIG. 51 is a diagram showing the basic screen K2 when one thumbnail image among the thumbnail images displayed in the case display region 710 is selected.

In the example shown in FIG. 51, in the case display region 710, a thumbnail image of a similar case displayed in the 1st-row, 4th-column has been selected. Therefore, the color of the background of the thumbnail image has been changed. Specifically, a color of a frame-like region enclosing an outer periphery of the selected thumbnail image has been changed. Accordingly, the user can be notified that the thumbnail image has changed to a selected state.

In this case, as the color of the background, for example, a color that clearly differs from a color of a background of the case display region 710 is adopted. In the example shown in FIG. 51, for example, yellow is adopted. Moreover, while a mode in which the color of a frame-like region of a thumbnail image is changed has been shown in the example in FIG. 51, a mode in which the frame-like region blinks or a mode in which brightness of the frame-like region is increased may be adopted instead.

Figure 52:
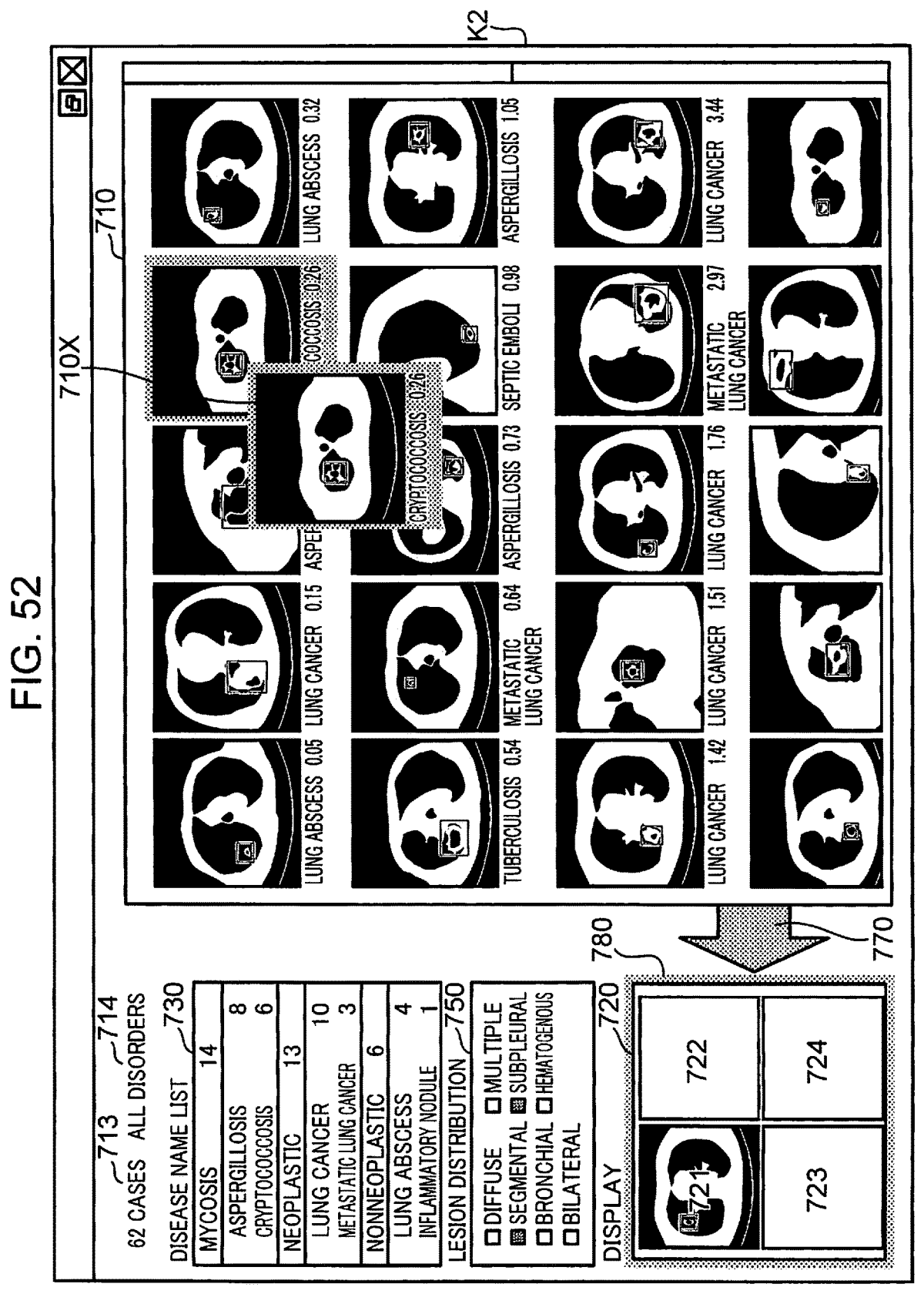

Next, when the input control unit 103 senses an operation for dragging the thumbnail image (YES in S3200), the display control unit 104, as shown in FIG. 52, generates a translucent duplicate 710X including the thumbnail image and the frame-like region enclosing the thumbnail image and moves and displays the duplicate 710X so as to track the dragging operation (S3300). On the other hand, when the input control unit 103 does not sense an operation for dragging the thumbnail image (NO in S3200), the process is returned to S3000.

FIG. 52 is a diagram showing the one thumbnail image selected in FIG. 51 being dragged. In addition, in S3300, the display control unit 104 changes a color of an arrow symbol 770 that connects the case display region 710 and the layout region 720 and a color of a frame region 780 that enclose the layout region 720. Accordingly, the user is prompted to continuously execute an operation for dragging the thumbnail image toward the layout region 720.

Moreover, while a mode in which colors of the arrow symbol 770 and the frame region 780 has been shown in FIG. 52, a mode in which brightness of the arrow symbol 770 and the frame region 780 is increased or a mode in which the arrow symbol 770 and the frame region 780 blink may be adopted instead.

Figure 53:
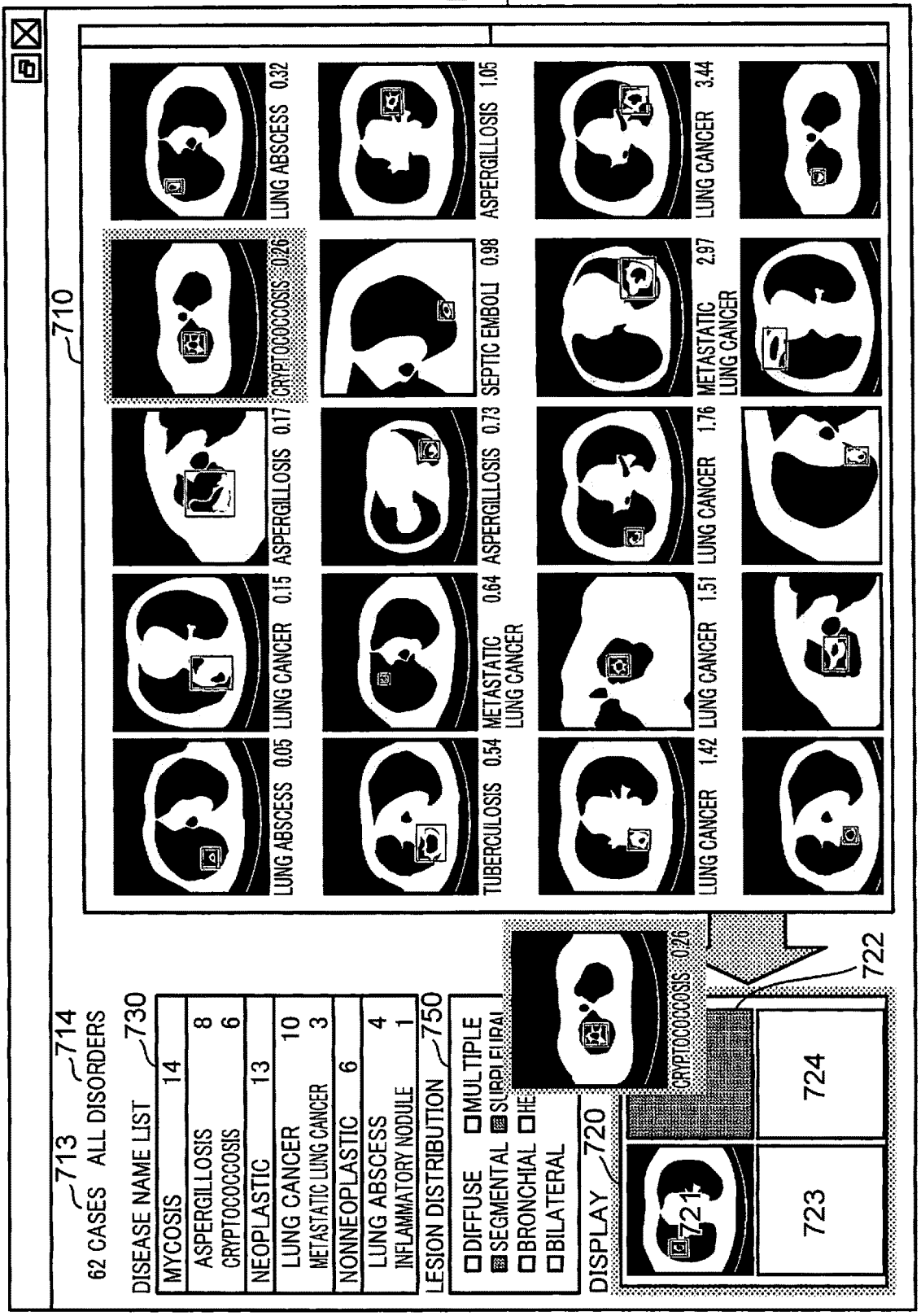
FIG. 53 is a diagram showing a basic screen on which a color of a display box has been changed.

When the user further continues the dragging operation and the input control unit 103 senses that a position of the mouse cursor has entered any of the display boxes 721 to 724 in the layout region 720 (YES in S3400), the display control unit 104 changes a color of any one of the display boxes 722 to 724 as shown in FIG. 53 (S3500). On the other hand, when the input control unit 103 does not sense that a position of the mouse cursor has entered the layout region 720 (NO in S3400), the process is advanced to S3600.

FIG. 53 is a diagram showing a basic screen on which a color of the display box 722 has been changed. In the example shown in FIG. 53, since the mouse cursor has entered the top right (1st-row, 2nd-column) display box 722, the color of the display box 722 has been changed. In this case, as the changed color of the display box 722, for example, a color that is clearly different from the color of the background of the display box 722 is adopted. In the example shown in FIG. 53, the display box 722 is changed to, for example, blue.

Accordingly, when dragging is ended at this stage, the user can be notified that the thumbnail image is to be displayed in the display box 722. While a mode in which the color of the display box 722 is changed has been shown, a mode in which brightness of the display box 722 is increased or the display box 722 blinks may be adopted instead.

Subsequently, when the input control unit 103 senses an operation for ending the dragging (YES in S3600), the input control unit 103 judges whether or not the position of the mouse cursor at the end of the dragging is inside the layout region 720 (S3700). On the other hand, when the input control unit 103 does not sense an operation for ending the dragging (NO in S3600), the process is returned to S3300. In addition, when the position of the mouse cursor at the end of the dragging is not inside the layout region 720 (NO in S3700), the input control unit 103 returns the process to S3700. In this case, for example, if a left button of the mouse had been clicked at the start of dragging, an operation for releasing the left button corresponds to the operation for ending the dragging.

Figure 54:
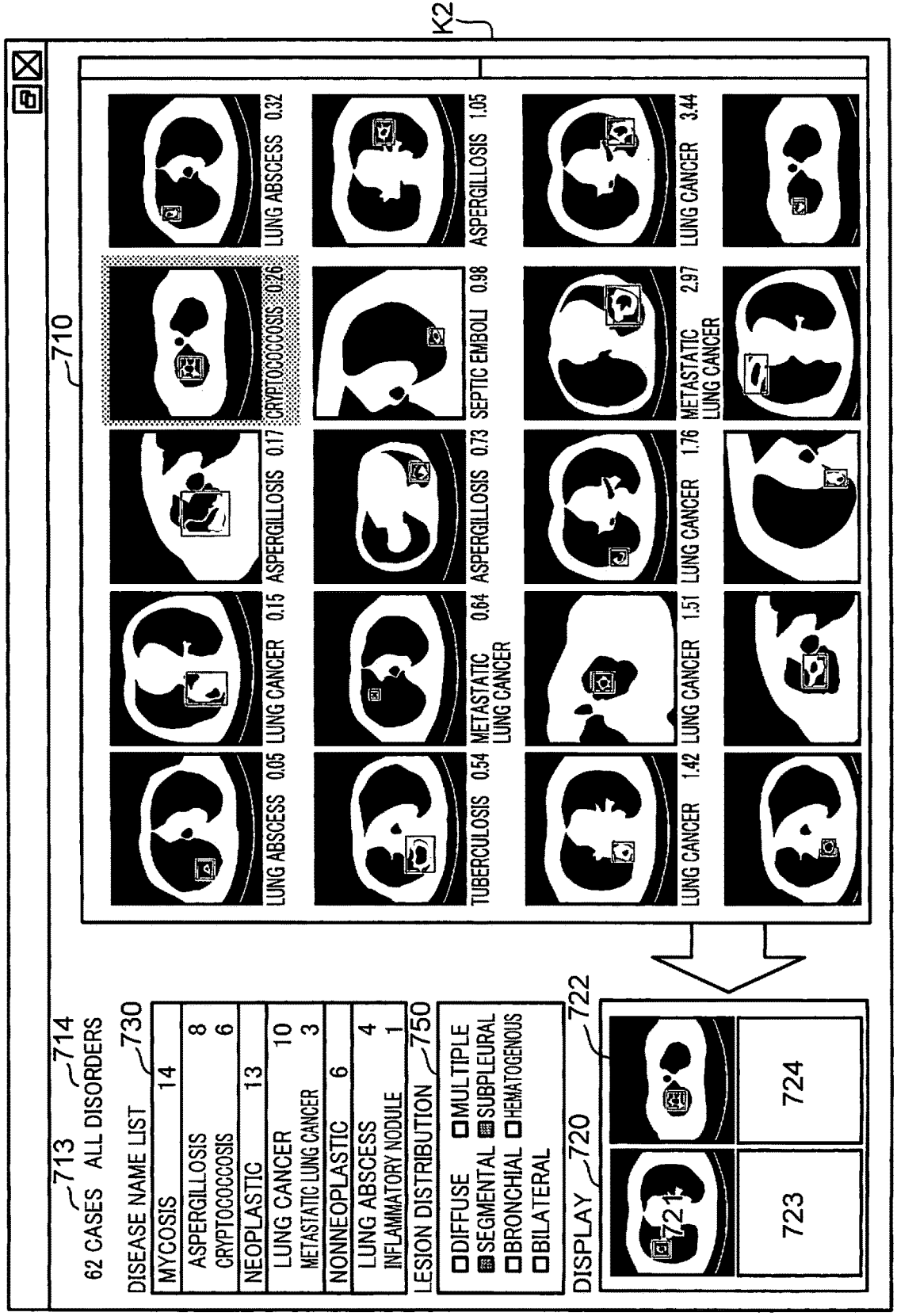
FIG. 54 is a diagram showing a basic screen when a thumbnail image is displayed in a layout region.

When the input control unit 103 judges that the position of the mouse cursor at the end of the dragging is inside the layout region 720 (YES in S3700), as shown in FIG. 54, the display control unit 104 displays the selected thumbnail image in any of the display boxes 722 to 724 (S3800). At this point, the duplicate 710X is erased. FIG. 54 is a diagram showing the basic screen K2 when the thumbnail image is displayed in the layout region 720.

Accordingly, the thumbnail image of the diagnosis object case and the thumbnail image of the similar case selected by the user are displayed adjacent to each other, albeit in small image sizes. Therefore, the user can readily compare the two thumbnail images with each other. In this case, a thumbnail image is displayed in any of the display boxes 722 to 724 because the thumbnail image of the diagnosis object case is already displayed in the display box 721. Moreover, when the position of the mouse cursor at the end of the dragging is inside the display box 721, the display control unit 104 may display the selected thumbnail image in any one of the display boxes in which a thumbnail image is not displayed. This concludes S800.

Returning now to FIG. 49, when the thumbnail image of the similar case is displayed in the display box 722, the display box managing unit 106 refers to the similar case data

4000 (FIG. 26) of the displayed thumbnail image, registers a slice ID corresponding to the thumbnail image in the display box management information 4410 (FIG. 44), and updates the display box management information 4410 (S810). In the example in FIG. 54, a thumbnail image is dropped in the 1st-row, 2nd-column display box 722. Therefore, the slice ID 4200 registered in the similar case data 4000 (FIG. 26) of the selected thumbnail image is registered in the 1st-row, 2nd-column field of the table 4412 in FIG. 44.

FIG. 55 is a diagram showing the display box management information 4410 in which a slice ID of a similar case has been registered. As is apparent from a comparison with FIG. 44, a slice ID "CT34298362" is newly registered in the 1st-row, 2nd-column field of the table 4412 of the display box management information 4410 shown in FIG. 55 and a slice ID of a similar case displayed in the layout region 720 is registered.

Returning to FIG. 49, when the display box management information 4410 is updated, the display box managing unit 106 notifies a slice ID related to the update to the communication control unit 110 (S820). When viewing this process from the perspective of application layers, the slice ID is notified by the similar case retrieval application "B" to the medical information management application "A" (S820).

The communication control unit 110 to which the slice ID is handed over transmits the slice ID to the communication control unit 206 of the medical information management system 200 (S821).

Figure 56:
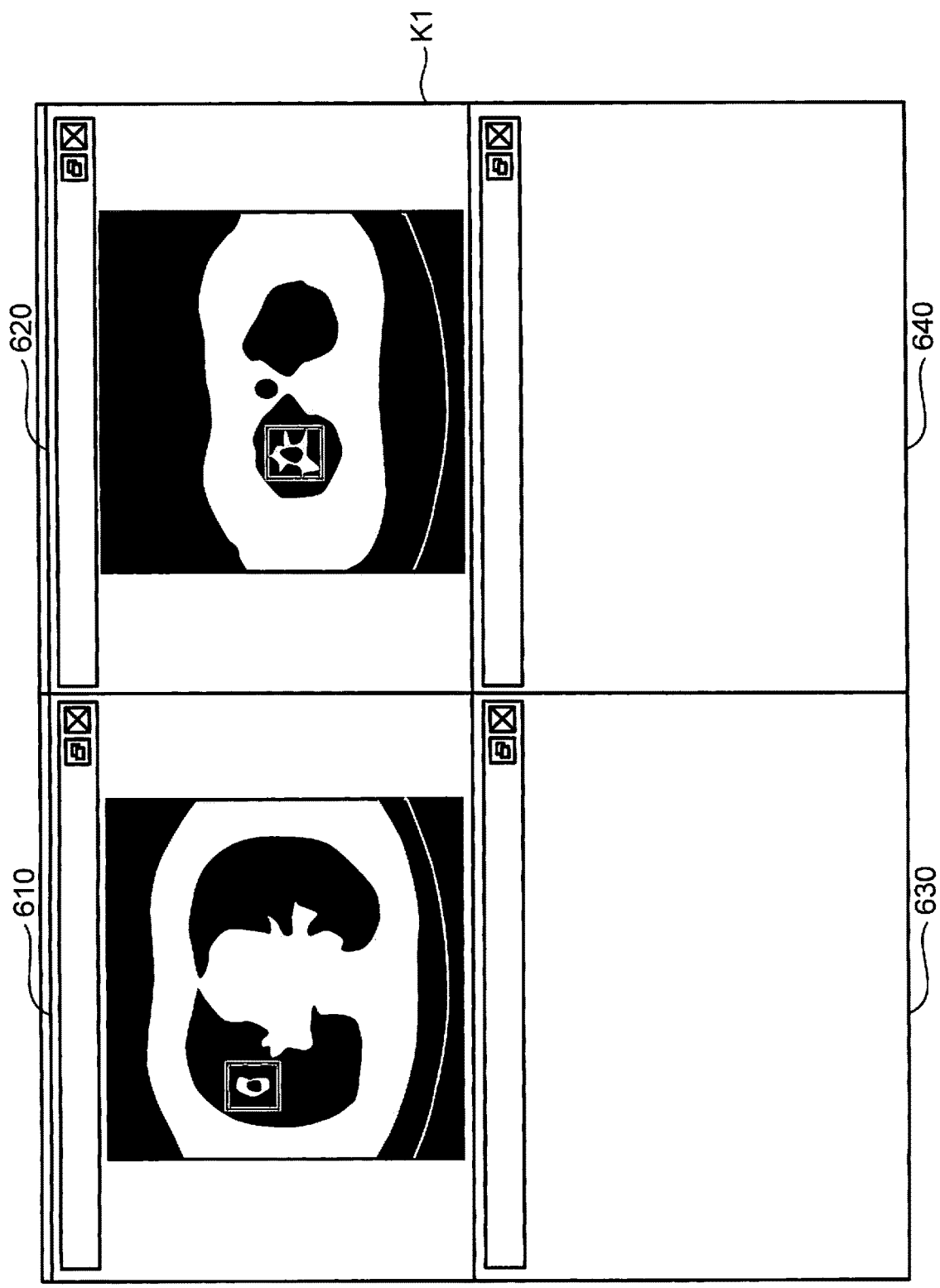
FIG. 56 is a diagram showing a basic screen of a display when a slice image is displayed on a medical image viewer.

Upon receiving the slice ID, the communication control unit 206 notifies the slice ID to the medical image data managing unit 204. The medical image data managing unit 204 refers to the medical image database 2000 (FIG. 24) and identifies a series ID including the slice ID, acquires all slice images of the series represented by the identified slice ID (S830), and hands over the slice images to the communication control unit 206. Subsequently, the communication control unit 206 transmits all slice images of the acquired series to the communication control unit 110 of the information terminal 100 (S840). When the communication control unit 110 receives all of the slice images, the display control unit 104 displays the slice images of the slice ID on a medical image viewer corresponding to the display box to which the slice ID has been registered in S810 (S850) and, at the same time, expands all slice images including the slice ID on a display memory corresponding to the medical image viewer. FIG. 56 is a diagram showing the basic screen K1 of the display 101*a* when a slice image is displayed on a medical image viewer. In the example shown in FIG. 56, a slice image is displayed on the medical image viewer 620. This is because the user had displayed the thumbnail image of the similar case in the display box 722.

As described above, when thumbnail images of a large number of similar cases displayed in the case display region 710 are dragged to the layout region 720, a thumbnail image of a diagnosis object case initially displayed after starting the similar case retrieval application and a thumbnail image of a similar case are displayed adjacent to each other in the layout region 720. Therefore, the user can compare the thumbnail images and determine a degree of similarity between cases in a simple manner.

In addition, a diagnosis object case and a similar case are displayed on a medical image viewer on the display 101*a* in a same image arrangement as the image arrangement in the layout region 720.

The user can compare a diagnosis object case and a similar case while slice-feeding and determine a degree of similarity in detail. FIGS. 57 to 60 are diagrams showing display relationships between the two displays 101*a* and 101*b*. Moreover, in FIGS. 57 to 60, upper parts represent the basic screen K1 that is displayed on the display 101*a* and lower parts represent the basic screen K2 that is displayed on the display 101*b*.

FIG. 57 shows the basic screens K1 and K2 displayed on the displays 101*a* and 101*b* immediately following start-up of the similar case retrieval application. Immediately following the start-up of the similar case retrieval application, a thumbnail image of a diagnosis object case is displayed in the display box 721 in the layout region 720 of the basic screen K2. Thumbnail images are not displayed in the other display boxes 722 to 724.

In conjunction therewith, on the basic screen K1, a slice image of the diagnosis object case is displayed on the medical image viewer 610 corresponding to the display box 721.

In FIG. 58, in the case display region 710 on the basic screen K2, a thumbnail image S801 of the 1st-row, 4th-column similar case is selected and the thumbnail image S801 is dragged to the display box 724. Therefore, on the basic screen K1, a slice image corresponding to the dragged thumbnail image S801 is displayed on the medical image viewer 640 corresponding to the display box 724.

In FIG. 59, in the case display region 710 on the basic screen K2, a thumbnail image S901 of the 3rd-row, 3rd-column similar case is selected and the thumbnail image S901 is dragged to the display box 722. Therefore, on the basic screen K1, a slice image corresponding to the dragged thumbnail image 5901 is displayed on the medical image viewer 620 corresponding to the display box 722.

Figure 60:
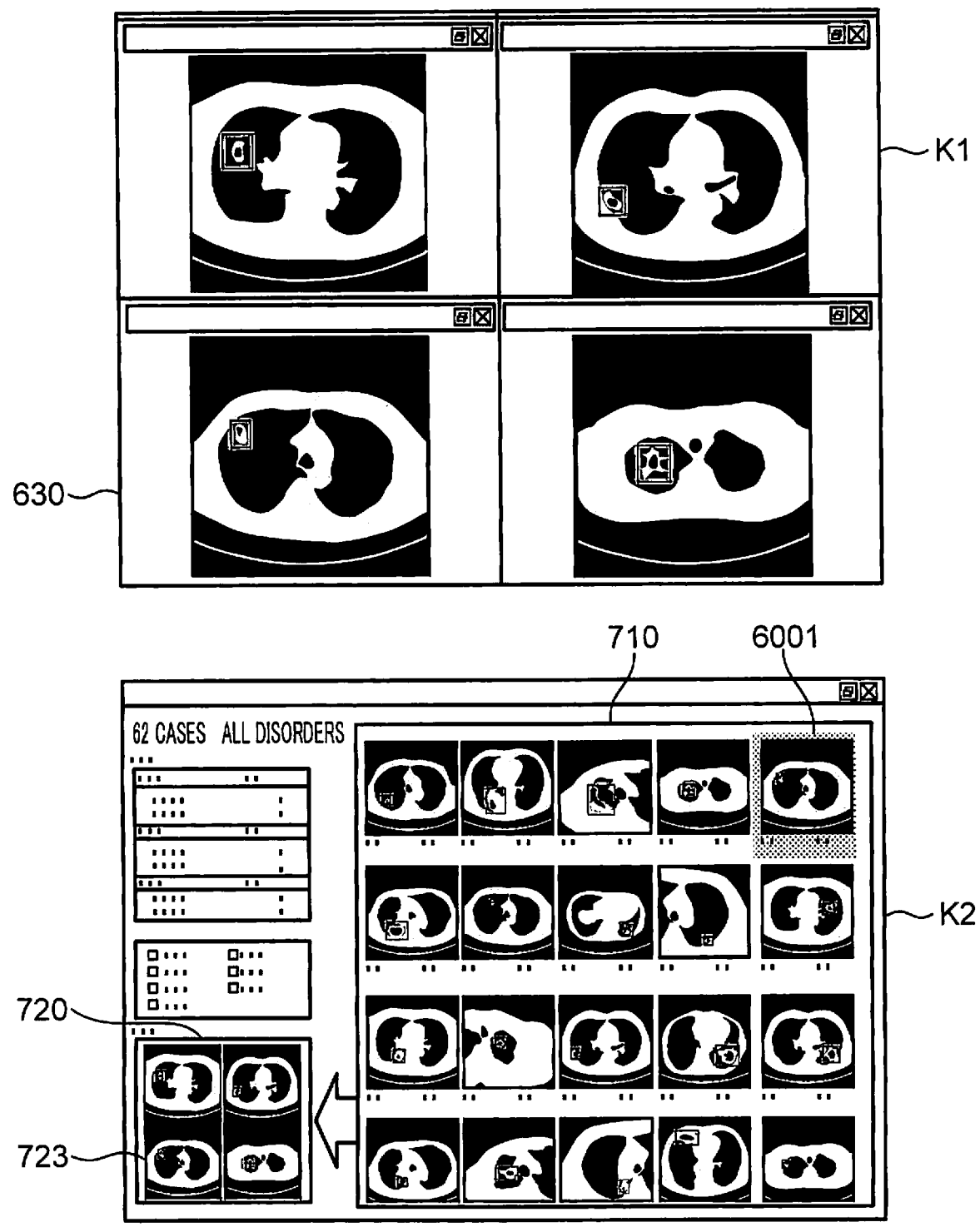
FIG. 60 is a diagram showing a display relationship between two displays.

In FIG. 60, in the case display region 710 on the basic screen K2, a thumbnail image 6001 of the 1st-row, 5th-column similar case is selected and the thumbnail image 6001 is dragged to the display box 723. Therefore, on the basic screen K1, a slice image corresponding to the dragged thumbnail image 6001 is displayed on the medical image viewer 630 corresponding to the display box 723.

In FIG. 60, thumbnail images fill all of the display boxes in the layout region 720. In this state, when the user wishes to further display a thumbnail image of a new similar case, the user need only drag the thumbnail image to a display box in the layout region 720 in the same manner as when all of the display boxes are not filled with thumbnail images (FIG. 61).

Figure 61:
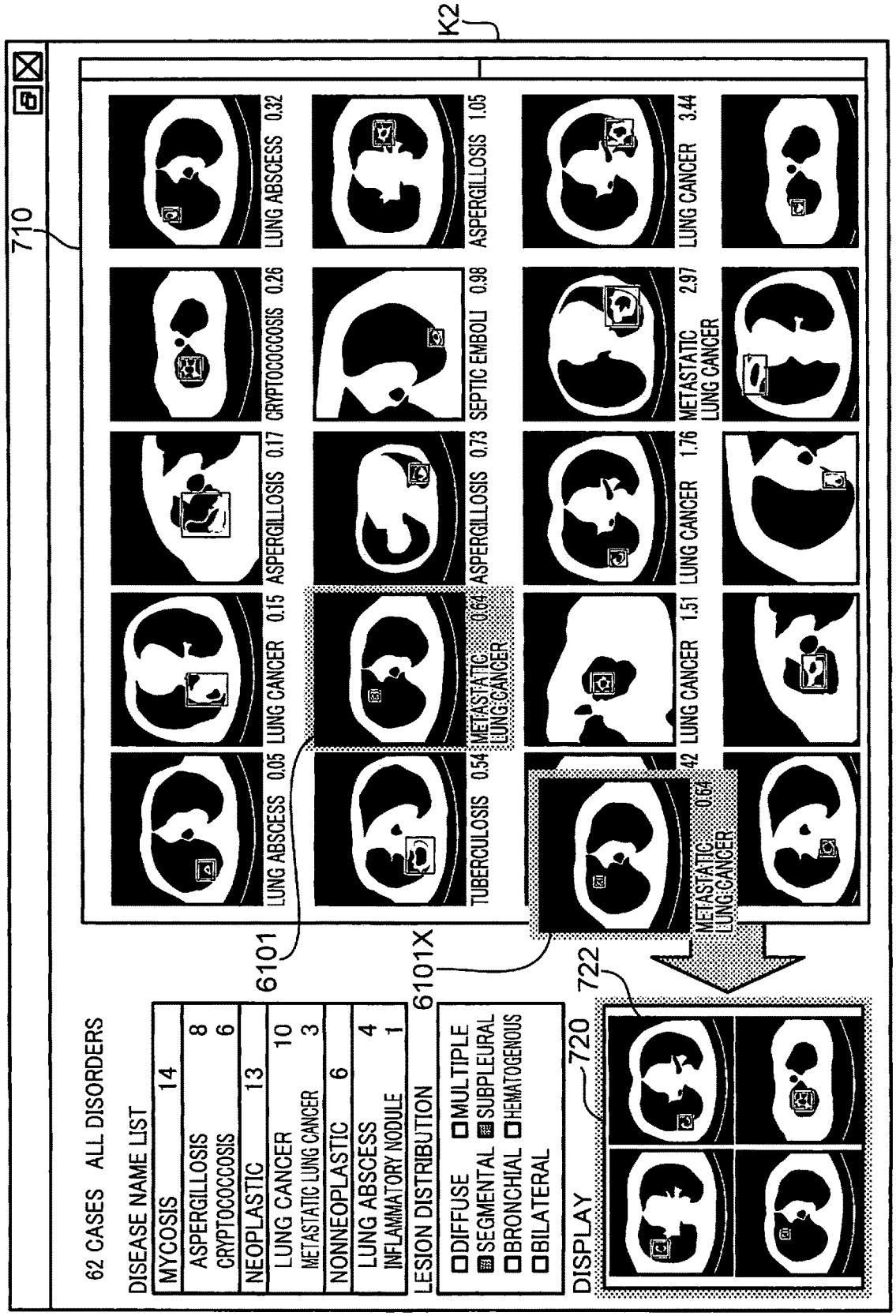
FIG. 61 is a diagram showing a basic screen in a state in which all display boxes are filled with thumbnail images and another thumbnail image is being dragged.

FIG. 61 is a diagram showing the basic screen K2 in a state in which all display boxes are filled with thumbnail images and another thumbnail image is being dragged. In the example shown in FIG. 61, in the case display region 710, since a 2nd-row, 2nd-column thumbnail image 6101 has been selected and then dragged, a duplicate 6101X of the thumbnail image 6101 is displayed. In addition, the user is dragging the duplicate 6101X toward the layout region 720.

Let us assume that, at this point, the user has dropped the duplicate 6101X at the display box 722. In this case, the duplicate 6101X becomes hidden and the thumbnail image 6101 overwrites the display box 722. Accordingly, the thumbnail image 6101 is displayed in the display box 722 in place of a previously displayed thumbnail image.

In conjunction with the overwriting, the medical image viewer 620 corresponding to the display box 722 is also updated by a slice image corresponding to the thumbnail image 6101.

Moreover, since the thumbnail image of the retrieval query image displayed in the 1st-row, 1st-column display box 721 should be compared to a thumbnail image of a similar case, the thumbnail image of the retrieval query image is desirably not updated by the thumbnail image of the similar case.

Figure 62:
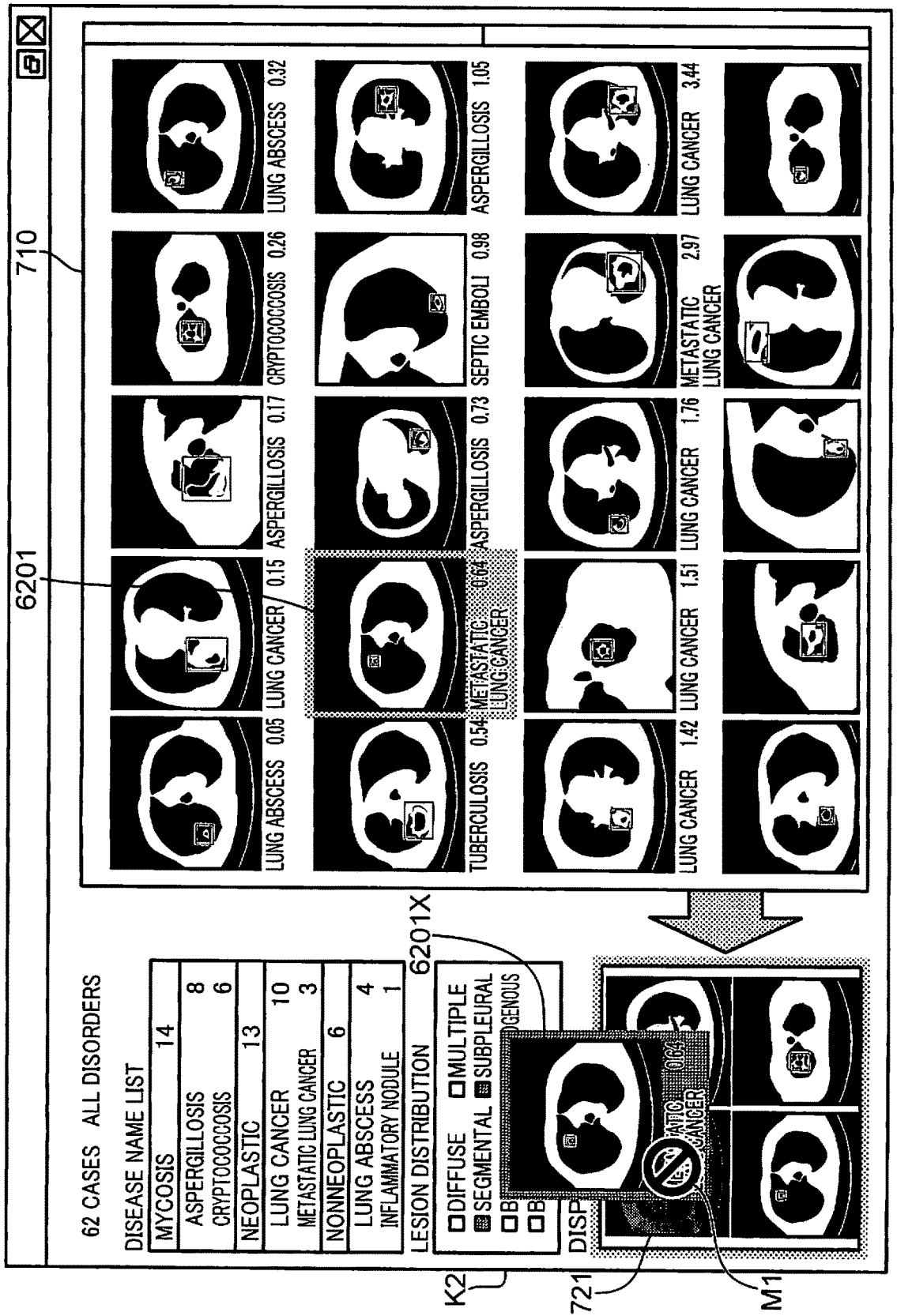
FIG. 62 is a diagram showing a basic screen on which a mark is displayed on a display box.

In consideration thereof, when the mouse cursor enters the display box 721 in which the thumbnail image of the retrieval query image in the layout region 720 is displayed, mark M1 indicating that a thumbnail image cannot be dropped may be displayed as shown in FIG. 62 instead of a mode in which a color of the display box is changed as shown in FIG. 53. FIG. 62 is a diagram showing the basic screen K2 when the mark M1 is displayed in a display box. In the example shown in FIG. 62, the 2nd-row, 2nd-column thumbnail image 6201 in the case display region 710 has been selected, the mouse cursor has entered the display box 721, and a duplicate 6201X of the thumbnail image 6201 has been dragged to the display box 721.

In this case, the display control unit 104 displays the mark M1 so as to overlap with the display box 721. In addition, the display control unit 104 changes the color of a frame-like region of the duplicate 6201X to a color indicating that dropping of a thumbnail image is prohibited and, at the same time, changes the color of the display box 721 to a color indicating that dropping of a thumbnail image is prohibited. While, for example, red is adopted as the color indicating that dropping is prohibited, this is simply an example. Accordingly, since the thumbnail image of the retrieval query image is displayed in the display box 721, the user can recognize that a thumbnail image cannot be displayed.

Figure 63:
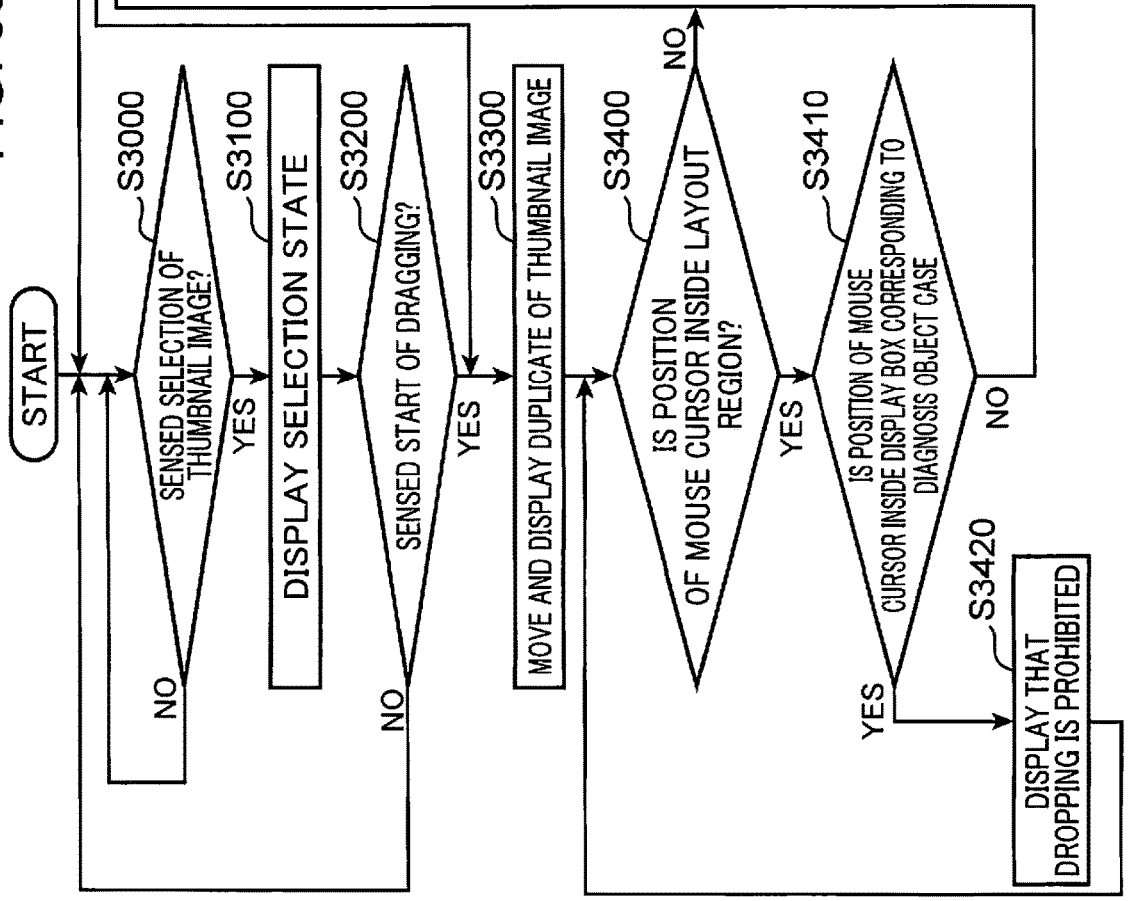
FIG. 63 is a flow chart showing a modification of FIG. 50.

FIG. 63 is a flow chart showing a modification of FIG. 50. A difference from FIG. 50 is that S3410, S3420, S3710, and S3720 are newly provided.

In S3410, the input control unit 103 judges whether or not a position of the mouse cursor is inside the display box 721 corresponding to the diagnosis object case. When the input control unit 103 judges that the position of the mouse cursor is inside the display box 721 (YES in S3410), as shown in FIG. 62, the display control unit 104 displays the mark M1 indicating that dropping is prohibited in the display box 721 and, at the same time, displays the display box 721 in a color indicating that dropping is prohibited (S3420). Once S3420 is concluded, the process is returned to S3400. In addition, in S3410, when the position of the mouse cursor is not inside the display box 721 (NO in S3410), the process is advanced to S3500.

In S3700, when a position at which dragging had ended is inside the layout region 720 (YES in S3700) and the thumbnail image of a similar case is already displayed in a display box at the position at which dragging had ended (YES in S3700), the display box managing unit 106 erases the association between the thumbnail image and the display box (S3720). For example, let us assume that the position at which dragging had ended is the display box 722 and that a thumbnail image is already displayed in the display box 722. In this case, the display box managing unit 106 erases the slice ID that is registered in the 1st-row, 2nd-column field corresponding to the display box 722 from the display box management information 4410.

On the other hand, when a thumbnail image is not displayed in the display box at which dragging had ended (NO in S3710), the process is advanced to S3800. In S3800, the display control unit 104 displays the dragged thumbnail image in the corresponding display box. In this case, the display box managing unit 106 registers a slice ID corresponding to the dragged thumbnail image in a field of the corresponding display box in the display box management information 4410.

Figure 64:
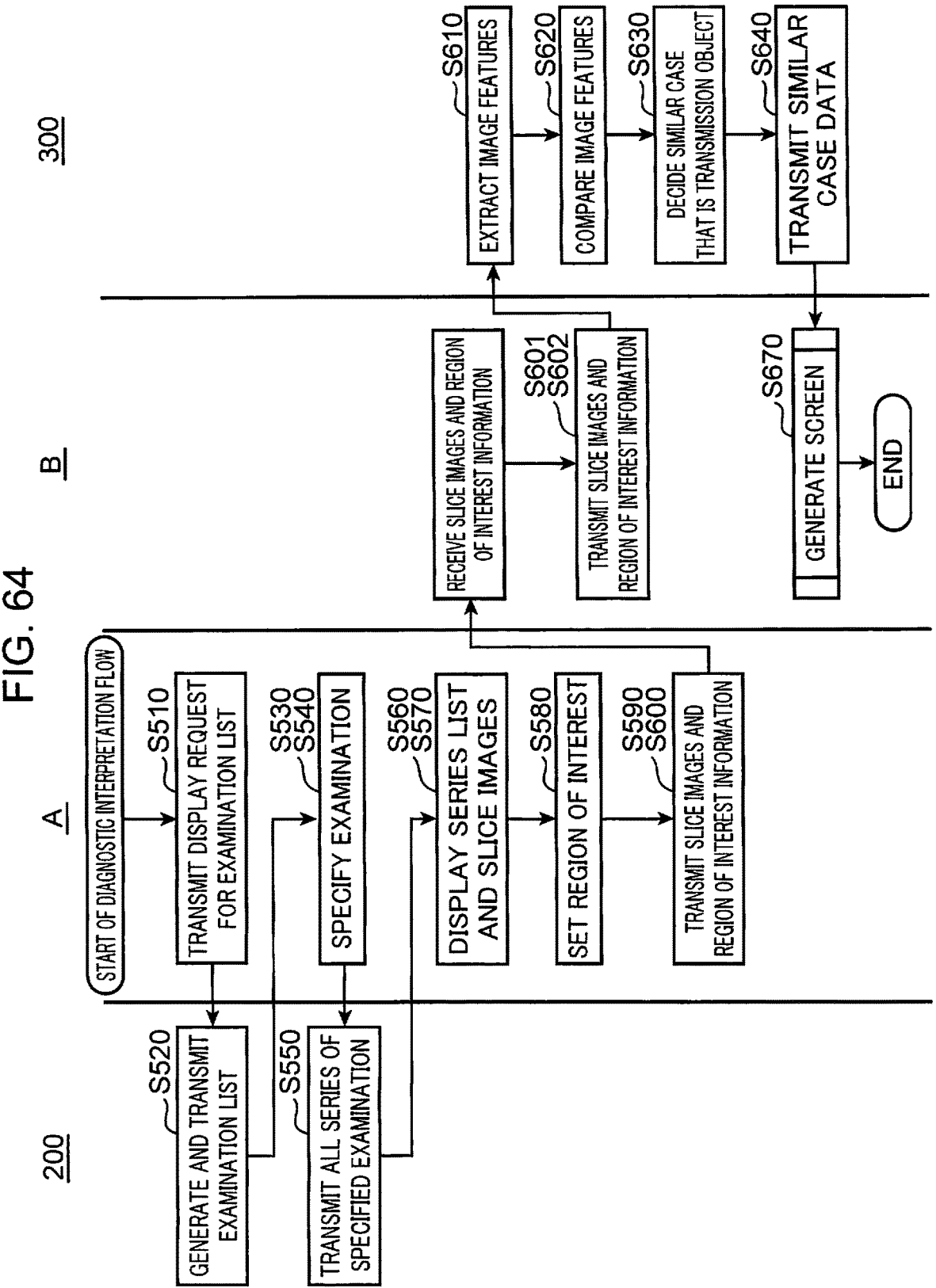
FIG. 64 is a sequence diagram when focusing on the sequence diagrams shown in FIGS. 28 and 32 on an application level.

Next, processes by the information terminal 100, the medical information management system 200, and the case retrieval system 300 when focusing on the sequence diagrams shown in FIGS. 28, 32, and 49 on an application level will be described. FIG. 64 is a sequence diagram when focusing on the sequence diagrams shown in FIGS. 28 and 32 on an application level. In FIG. 64, same processes as in FIG. 28 are assigned same reference characters.

Figure 65:
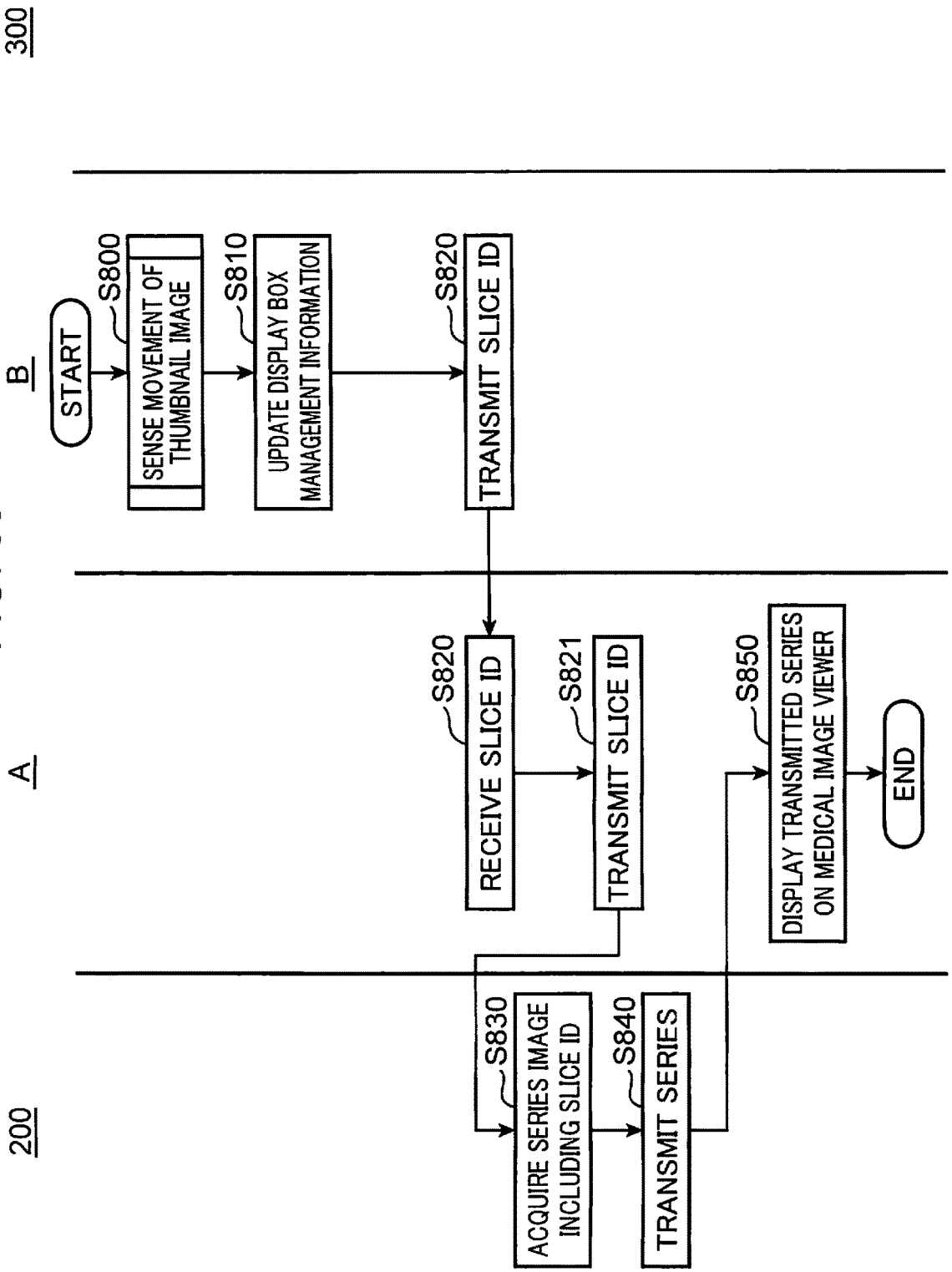
FIG. 65 is a sequence diagram when focusing on the sequence diagram shown in FIG. 49 on an application level.
Figure 66:
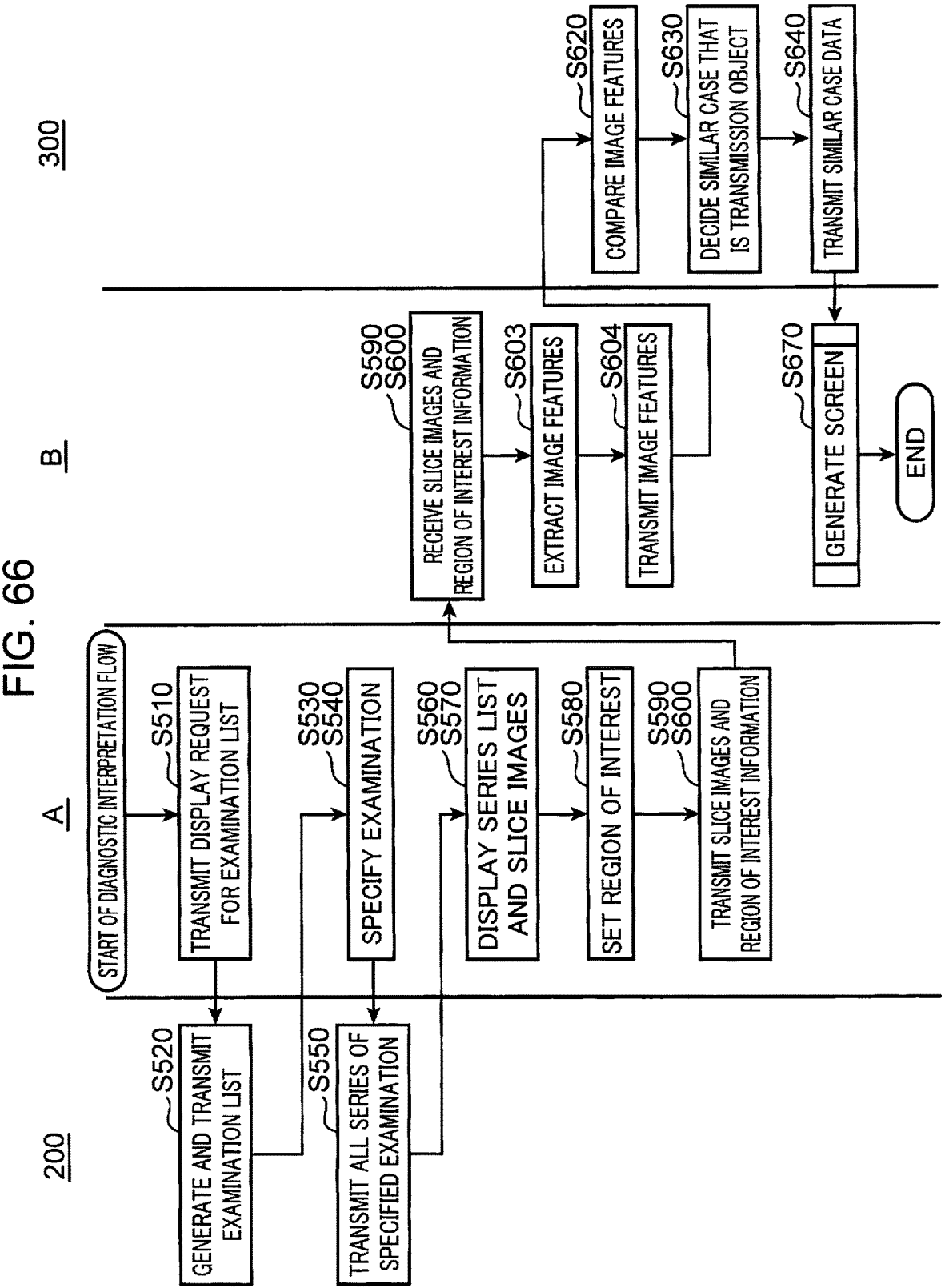
FIG. 66 is a sequence diagram which focuses, on an application level, on a process when a thumbnail image of a similar case is dragged-and-dropped in an information terminal.

In FIGS. 64 to 66, "A" denotes a process of the medical information management application executed by the information terminal 100 and "B" denotes a process of the similar case retrieval application executed by the information terminal 100. Hereinafter, the medical information management application will be described as "application A" and the similar case retrieval application will be described as "application B".

First, the application A accepts a display request for a list of examinations to be diagnostic interpretation objects from a user, and transmits the display request to the medical information management system 200 (S510). Upon receiving the display request of the examination list, the medical information management system 200 lists examinations for which image-based examination has been performed but diagnostic interpretation has not been completed, generates a list of examinations to be diagnostic interpretation objects, and transmits the examination list to the application A.

Upon receiving the examination list, as shown in FIG. 29, the application A displays the examination list on the display 101, and when one examination is selected by the user from the examination list (S530), the application A transmits a display request for the selected examination to the medical information management system 200 (S540).

The medical information management system 200 having received the examination request transmits all slice images of all series included in the examination ID specified by the display request to the application A (S550).

Next, as shown in FIG. 30, the application A displays a series list that displays a list of information related to all series included in the specified examination ID (S560).

Subsequently, when a series that is a diagnostic interpretation object is selected by the user from the series list, the application A displays a slice image at a first slice position of the selected series on the medical image viewer 610 (S570). At this point, the user inputs an operation for slice feeding and causes a desired slice image to be displayed on the medical image viewer 610.

Next, the application A accepts an operation for setting a region of interest in the slice image displayed on the medical image viewer 610 from the user (S580).

Subsequently, the application A generates region of interest information representing the region of interest set by the user and transmits the region of interest information together with a slice image (slice image of the diagnosis object case) in which the region of interest is set to the application B (S590, S600).

Next, upon receiving the slice image and the region of interest information of the diagnosis object case, the application B transmits the slice image and the region of interest information to the case retrieval system 300 (S601, S602).

Upon receiving the slice image and the region of interest information, the case retrieval system 300 executes the processes of S610 to S640 in a similar manner to FIG. 32.

Subsequently, the application B generates an initial basic screen using the similar case data transmitted in S640 and the display box management information 4410 (S670). In addition, the application B executes the process of S670 that is shown in detail in FIG. 33.

FIG. 65 is a sequence diagram when focusing on the sequence diagram shown in FIG. 49 on an application level. In FIG. 65, same processes as in FIG. 49 are assigned same reference characters.

In S800 shown in FIG. 65, the application B senses a movement of a thumbnail image of a similar case to a display box. Details of the process of S800 have been described in FIG. 50.

Next, the application B refers to the similar case data 4000 (FIG. 26) of the thumbnail image displayed in the display box, registers a slice ID corresponding to the thumbnail image in the display box management information 4410 (FIG. 44), and updates the display box management information 4410 (S810).

Subsequently, the application B transmits the slide ID of the thumbnail image moved to the display box to the application A (S820).

Upon receiving the slide ID (S820), the application A transmits the slice ID to the medical information management system 200 (S821).

Subsequently, the medical information management system 200 executes the processes of S830 and S840 in a similar manner to FIG. 49.

In S850, when the application A receives all slice images of a corresponding series, the application A displays the slice images on a corresponding medical image viewer.

FIG. 66 is a sequence diagram which focuses, on an application level, on a process when a thumbnail image of a similar case is dragged-and-dropped in the information terminal 100.

S603 and S604 are not included in FIG. 64 while these steps are included in FIG. 66. In FIG. 66, an image feature is extracted by the information terminal 100. Therefore, the application B extracts an image feature from a region of interest set in the slice image of the diagnosis object case (S603) and transmits the extracted image feature to the case retrieval system 300 (S604).

Figure 67:
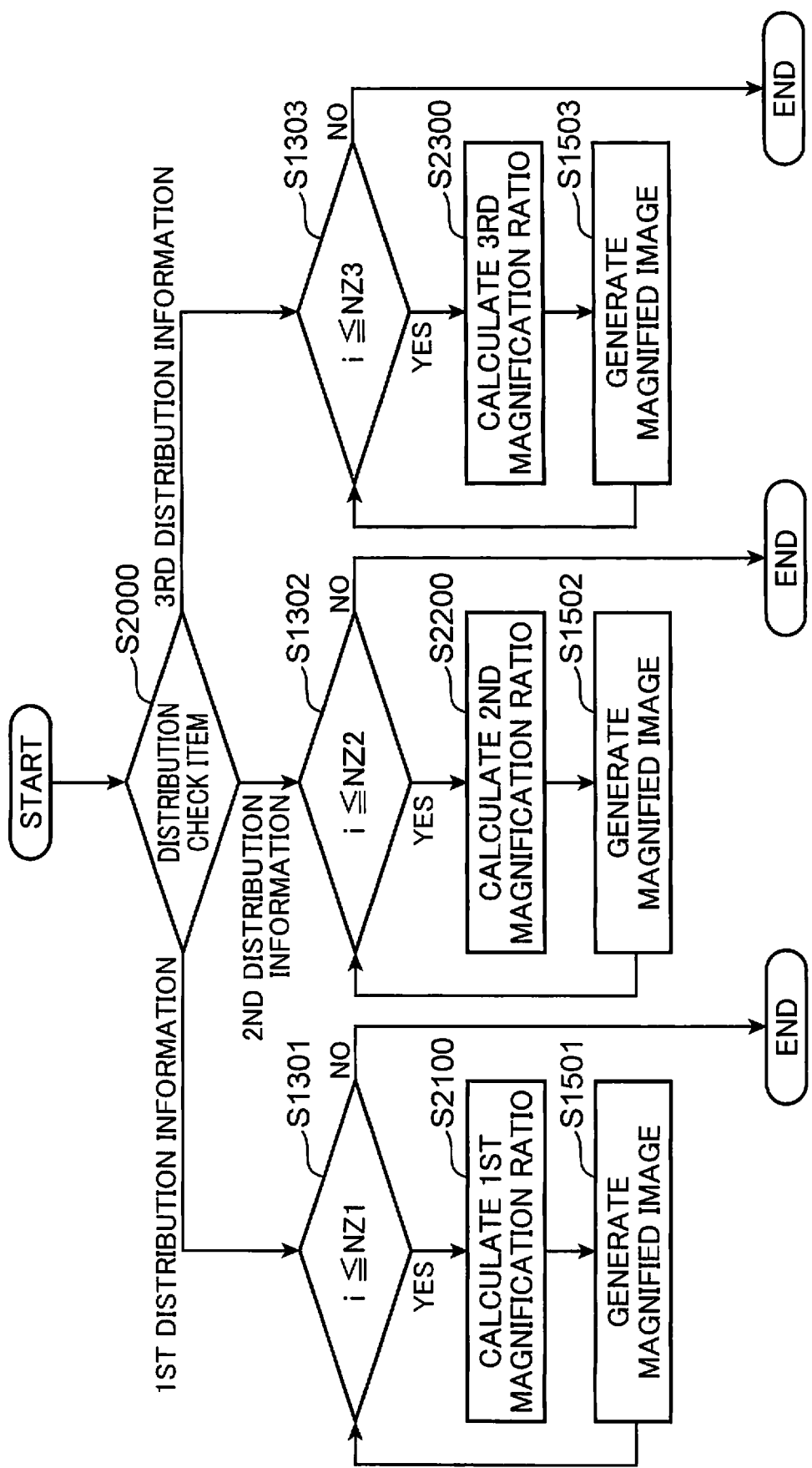
FIG. 67 is a flow chart showing a process when a lesion distribution displayed in a distribution list display region is selected.

Next, a process when a lesion distribution displayed in the distribution list display region 750 shown in FIG. 11 is selected will be described. FIG. 67 is a flow chart showing a process when a lesion distribution displayed in the distribution list display region 750 is selected.

In S2000, when the input control unit 103 senses an operation for selecting any one distribution check item among lesion distribution (distribution check items) displayed in the distribution list display region 750, the display control unit 104 judges which of first to third distribution information the sensed distribution check item corresponds to. In the case of the first distribution information, the process is advanced to S1301, in the case of the second distribution information, the process is advanced to S1302, and in the case of the third distribution information, the process is advanced to S1303.

The first distribution information is information for selecting a thumbnail image, in which a size of a region of interest belongs to a prescribed first range, from among thumbnail images of similar cases that are displayed as a list in the case display region 710. The prescribed first range indicates that the size of the region of interest is larger than a lung region. In this case, "bilateral", "multiple", "diffuse", and "hematogenous" correspond to the first distribution information. Therefore, a value range to which a size of a region of interest, which is set when diagnosing such lesion distribution, belongs is adopted as the first range.

The second distribution information is information for selecting a thumbnail image, in which a size of a region corresponding to a region of interest belongs to a prescribed second range (lower than the first range, that is, an upper limit value of the second range is not more than a lower limit value of the first range), from among thumbnail images of similar cases that are displayed as a list in the case display region 710. The prescribed second range indicates that a size of a region corresponding to a region of interest is a part of a lung region. In this case, "bronchial" and "segmental" correspond to the second distribution information. Therefore, a value range to which a size of a region of interest, which is set when diagnosing such lesion distribution, belongs is adopted as the second range.

The third distribution information is information for selecting a thumbnail image, in which a region of interest includes the pleura, from among thumbnail images of similar cases that are displayed as a list in the case display region 710. In this case, "subpleural" corresponds to the third distribution information.

In S1301, the display control unit 104 extracts, in a descending order of degrees of similarity, similar cases whose number is not more than a maximum displayable number (20 in the present embodiment) of thumbnail images in the case display region 710 among similar cases which have been obtained as a result of a similar case retrieval and which are similar cases of the lesion distribution selected by the user as the first distribution information. The display control unit 104 decides the number of the extracted similar cases as a number NZ1 of similar cases that are magnification objects. In addition, the display control unit 104 decides that a thumbnail image of an extracted similar case i (i is an index specifying the extracted similar cases and is an integer not less than 1) is a thumbnail image of a processing object. Subsequently, the display control unit 104 repeats the processes of S2100 and S1501 until the index i reaches NZ1. The display control unit 104 increments the index i by 1 each time the processes of S2100 and S1501 are executed. Once the index i exceeds NZ1 (NO in S1301), the process is finished.

In S2100, the display control unit 104 calculates a first magnification ratio corresponding to the first distribution information with respect to the similar case i. In this case, as the first magnification ratio, for example, 1.0 is adopted. However, this is simply an example and a magnification ratio other than 1.0 may be adopted as the first magnification ratio as long as the magnification ratio is a value that enables an entire region of interest that is set when diagnosing a lesion distribution representing the first distribution information to fit inside the display region.

In S1501, the display control unit 104 magnifies the thumbnail images of the i-number of similar cases at the first magnification ratio of the i-number of similar cases.

Figure 68:
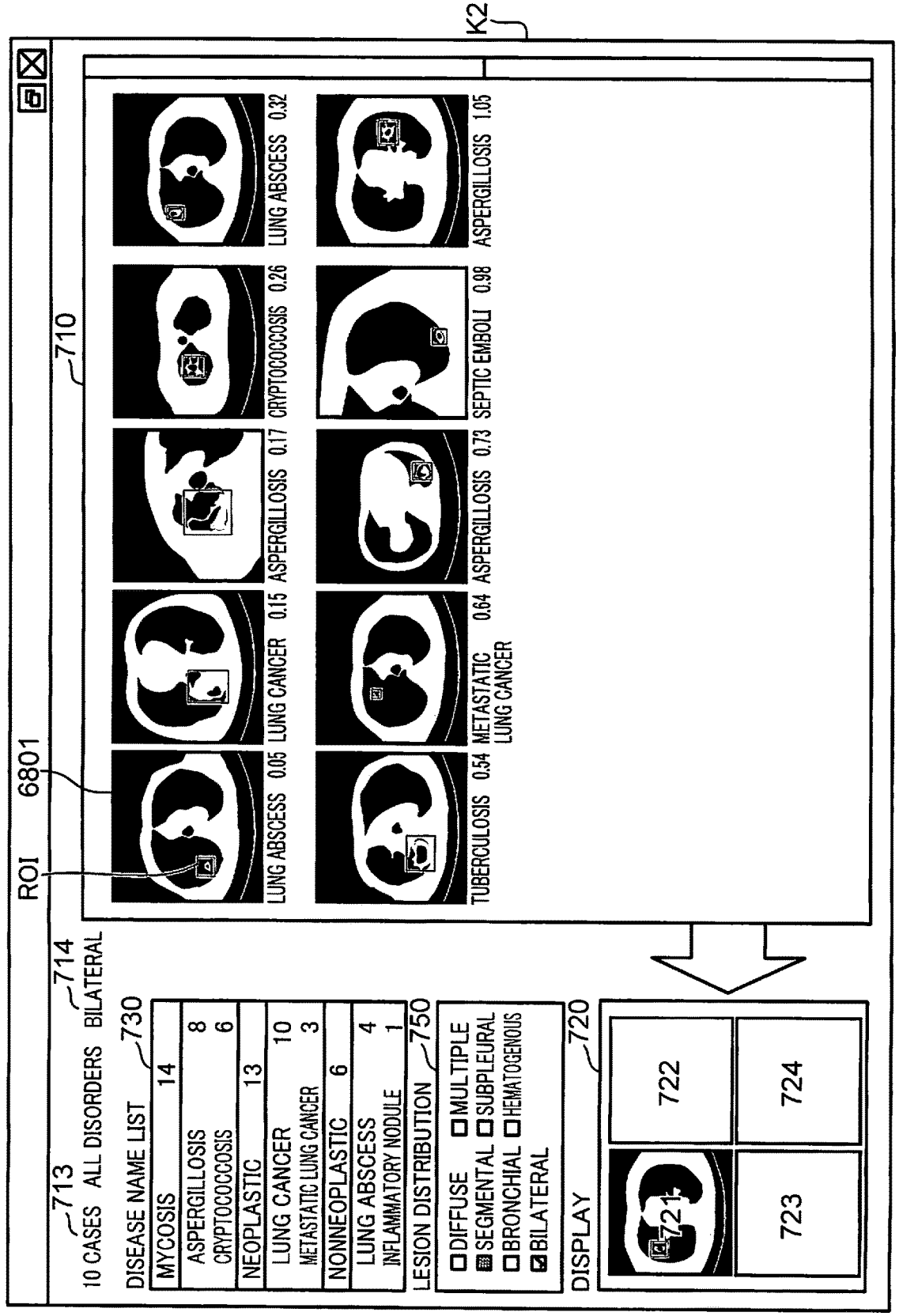
FIG. 68 is a diagram showing a basic screen when first distribution information is selected.

FIG. 68 is a diagram showing the basic screen K2 when the first distribution information is selected. In FIG. 68, bilateral is selected. In this case, only thumbnail images of similar cases whose lesion distribution corresponds to bilateral among the similar cases are displayed in the case display region 710. In addition, in this case, since the magnification ratio is 1.0, the thumbnail images are displayed in the case display region 710 in a same display mode as the thumbnail images displayed immediately after the similar retrieval result is obtained. In other words, the thumbnail images are displayed without a display position of the thumbnail images being adjusted so that a center of a region of interest ROI is positioned at a center of a display region 6801 and without being magnified.

In S1302, the display control unit 104 extracts, in a descending order of degrees of similarity, similar cases whose number is not more than a maximum displayable number of thumbnail images in the case display region 710 among similar cases which have been obtained as a result of a similar case retrieval and which are similar cases of the lesion distribution selected by the user as the second distribution information. The display control unit 104 decides the number of the extracted similar cases as a number NZ2 of similar cases that are magnification objects. In addition, the display control unit 104 decides that a thumbnail image of an extracted similar case i is a thumbnail image of a processing object. Subsequently, the display control unit 104 repeats the processes of S2200 and S1502 until the index i reaches NZ2. The display control unit 104 increments the index i by 1 each time the processes of S2200 and S1502 are executed. Once the index i exceeds NZ2 (NO in S1302), the process is finished.

In S2200, the display control unit 104 calculates a second magnification ratio corresponding to the second distribution information with respect to the similar case i using a size of a display region determined in advance for one thumbnail image in the case display region 710 and the region of interest information of the similar case i.

When the second distribution information is selected, the similar case i is magnified so that a size of the region of interest is around ½ of a size of the display region. Therefore, the display control unit 104 calculates a second magnification ratio ki with respect to the similar case i using, for example, the mathematical expression given below. If an area of the display region is denoted by Sd and an area of the region of interest of the thumbnail image of the similar case i that is magnification object is denoted by Si, then the second magnification ratio ki can be calculated by the following equation.

$$ki=1/2(Sd/Si)$$

In S1502, the display control unit 104 magnifies the thumbnail image of the similar case i by the second magnification ratio ki and displays thumbnail images in the case display region 710 so that a center of the region of interest of the thumbnail images is positioned at a center of the display region.

Figure 69:
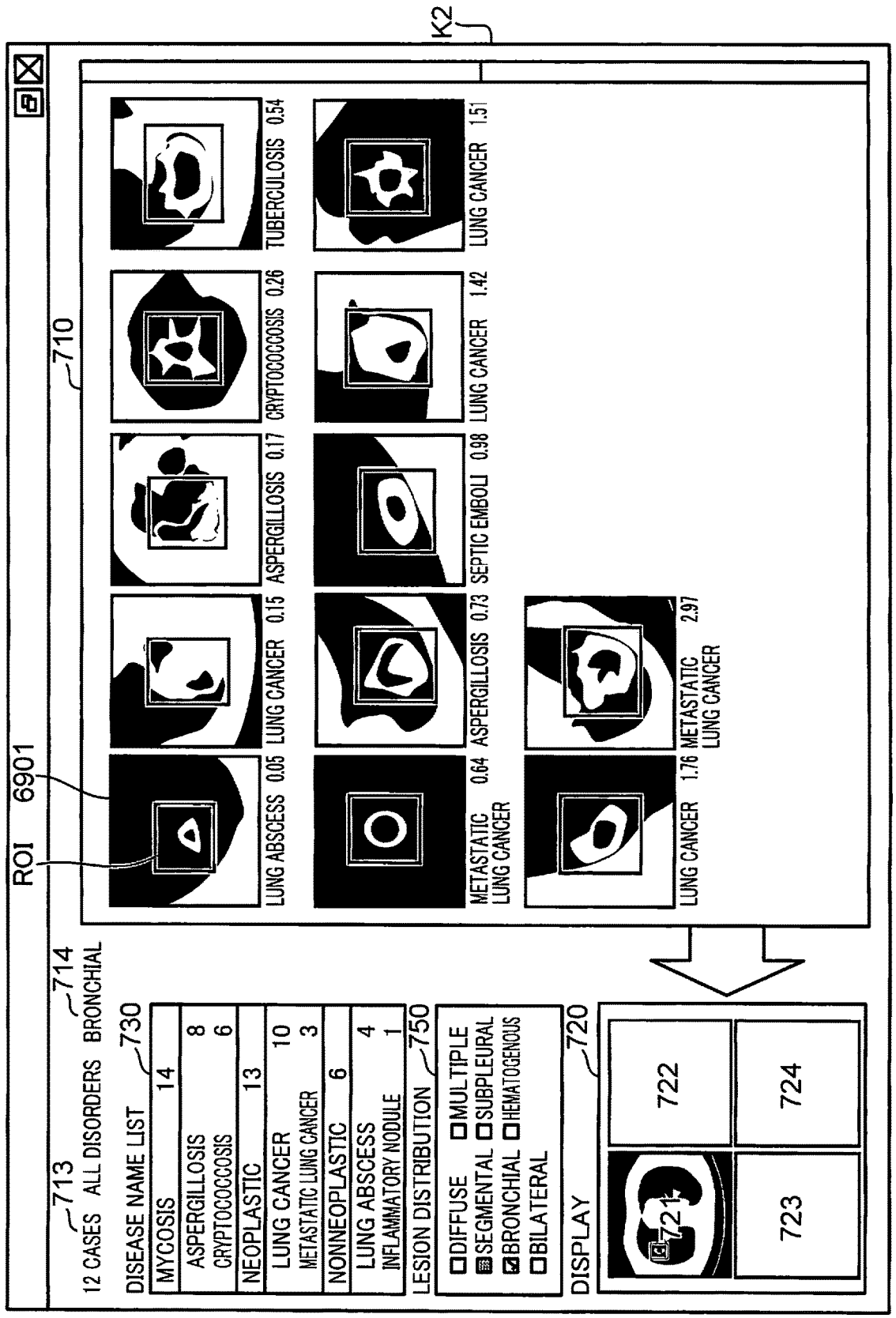
FIG. 69 is a diagram showing a basic screen when second distribution information is selected.

FIG. 69 is a diagram showing the basic screen K2 when the second distribution information is selected. In FIG. 69, bronchial is selected. In this case, only thumbnail images of similar cases whose lesion distribution corresponds to bronchial among the similar cases are displayed in the case display region 710. In addition, in the case display region 710, all thumbnail images have been magnified at the second magnification ratio so that the center of the region of interest ROI is positioned at the center of the display region 6901.

In S1303, the display control unit 104 extracts, in a descending order of degrees of similarity, similar cases whose number is not more than a maximum displayable number of thumbnail images in the case display region 710 among similar cases which have been obtained as a result of a similar case retrieval and which are similar cases of the lesion distribution selected by the user as the third distribution information. The display control unit 104 decides the number of the extracted similar cases as a number NZ3 of similar cases that are magnification objects. In addition, the display control unit 104 decides that a thumbnail image of the extracted similar case i is a thumbnail image of a processing object. Subsequently, the display control unit 104 repeats the processes of S2300 and S1503 until the index i reaches NZ3. The display control unit 104 increments the index i by 1 each time the processes of S2300 and S1503 are executed. Once the index i exceeds NZ3 (NO in S1303), the process is finished.

In S2300, the display control unit 104 calculates a third magnification ratio corresponding to the third distribution information with respect to the similar case i using a size of a display region determined in advance for one thumbnail image in the case display region 710, the region of interest information of the similar case i, and pleural region information 4900.

Figure 72:
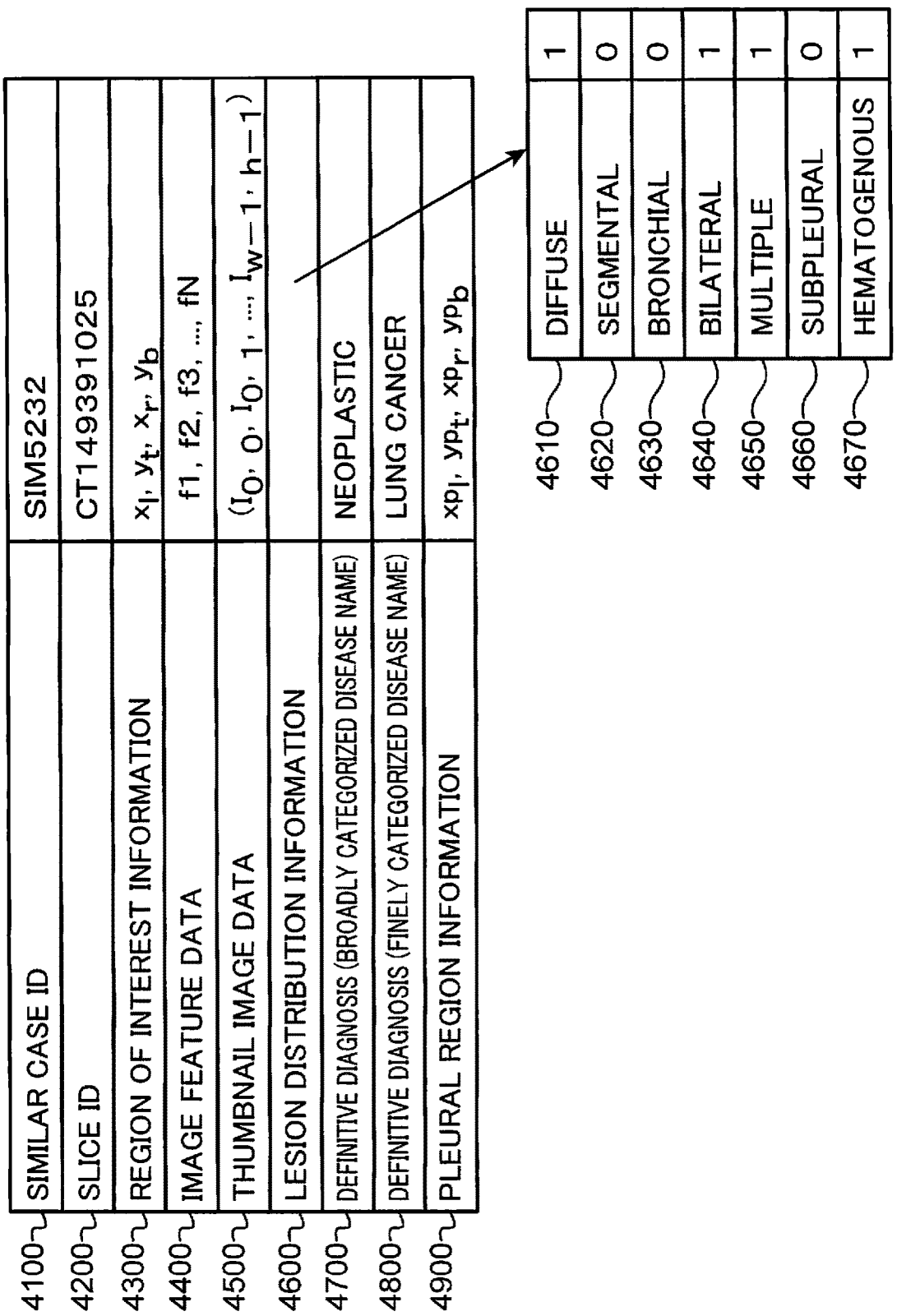
FIG. 72 is a diagram showing a data configuration of similar case data to which pleural region information has been added.

FIG. 72 is a diagram showing a data configuration of similar case data 4000 to which the pleural region information 4900 has been added. Moreover, when the pleural region information 4900 is not registered in the similar case data 4000, the pleural region information 4900 cannot be obtained. In this case, the display control unit 104 need only set the third magnification ratio to 1.0 which is the same value as the first magnification ratio. The pleural region information 4900 is information indicating a pleural region in a similar case.

In S1503, the display control unit 104 magnifies the thumbnail image of the similar case i by the third magnification ratio ki and displays thumbnail images in the case display region 710 so that a center of the region of interest of the thumbnail images is positioned at a center of the display region.

Figure 71:
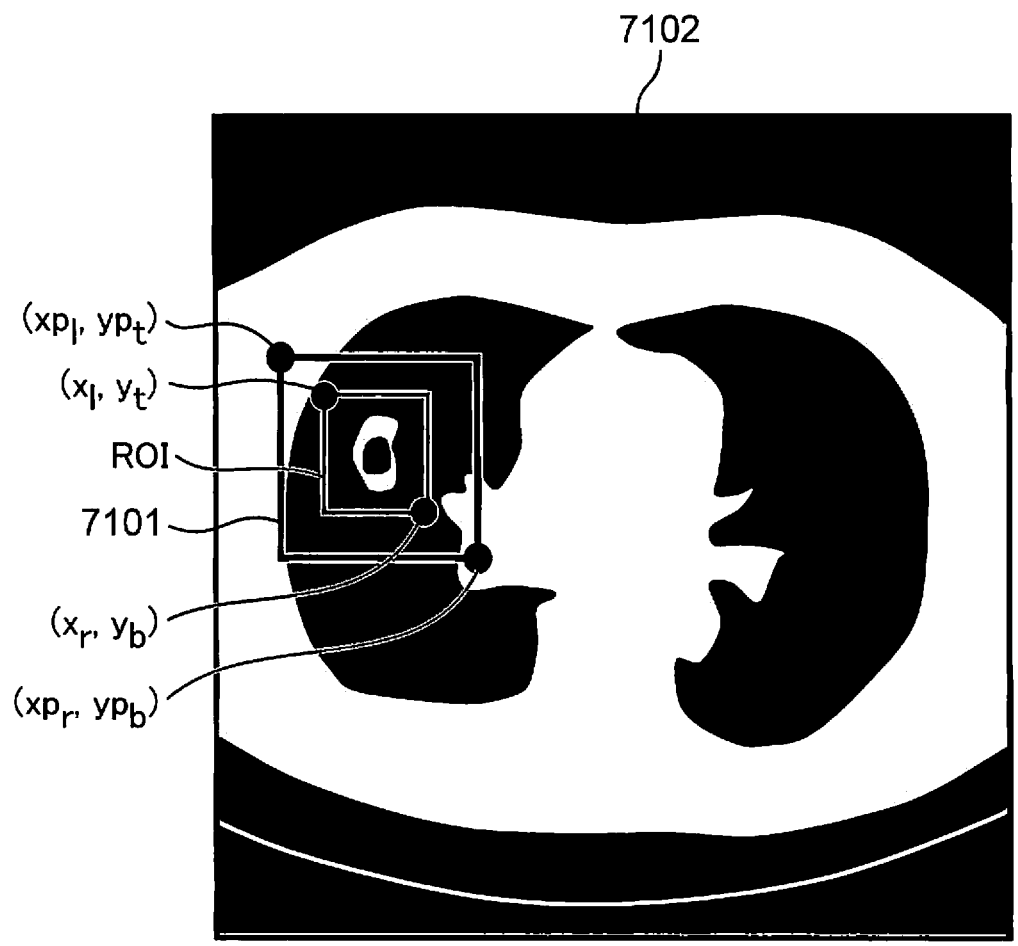
FIG. 71 is a diagram explaining a pleural region.

FIG. 71 is a diagram for describing a pleural region 7101. As shown in FIG. 71, the pleural region 7101 is a region which includes a pleura, whose center is positioned at a center of the region of interest ROI, and which has a rectangular shape slightly larger in size than the region of interest ROI. In this case, the pleural region information 4900 is constituted by four values including coordinates (xpl, ypt) of a top left vertex and coordinates (xrp, ypb) of a bottom right vertex of the pleural region 7101. When the third distribution information is selected, in order to display a magnified pleural region, the display control unit 104 calculates the third magnification ratio ki using the mathematical expression given below. If an area of the display region 7102 is denoted by Sd and an area of the pleural region 7101 is denoted by Sp, then the third magnification ratio ki can be calculated by the following equation.

$$ki=Sd/Sp$$

Moreover, the pleural region information 4900 may be input by the user together with region of interest information when creating the similar case data 4000. Alternatively, the pleural region information 4900 may be automatically created by having an image processing apparatus automatically extract a lung region from a slice image and judge a pleural position.

Figure 70:
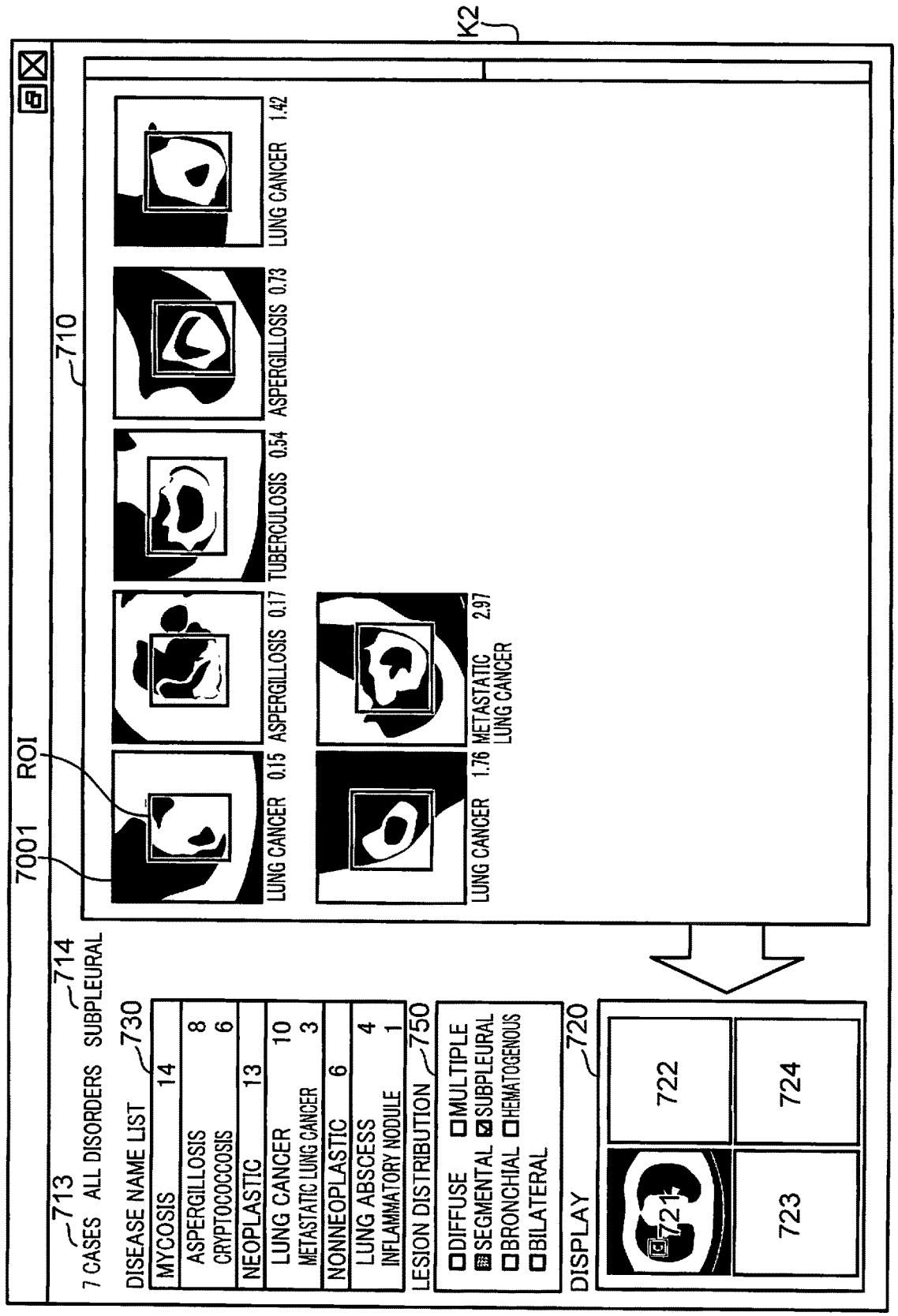
FIG. 70 is a diagram showing a basic screen when third distribution information is selected.

FIG. 70 is a diagram showing the basic screen K2 when the third distribution information is selected. In FIG. 70, subpleural is selected. In this case, only thumbnail images of similar cases whose lesion distribution corresponds to subpleural among the similar cases are displayed in the case display region 710. In addition, in the case display region 710, all thumbnail images have been magnified at the third magnification ratio so that the center of the region of interest ROI is positioned at the center of the display region 7001.

According to the process described above, thumbnail images are displayed in the case display region 710 at a magnification ratio that reflects contents of diagnosis with respect to lesion distribution. In addition, the thumbnail images are displayed in the case display region 710 while making sizes of regions of interest uniform. Therefore, an occurrence of a situation where a region of interest is magnified at a low magnification ratio in a part of the similar medical images and the region of interest is overlooked can be prevented and diagnostic accuracy can be improved.

Furthermore, since the magnification process is only performed on the similar cases displayed in the case display region 710 instead of on all of the similar cases obtained by similar case retrieval, a load on the system can be significantly reduced.

INDUSTRIAL APPLICABILITY

The present disclosure can be used in a similar case retrieval apparatus for presenting similar cases to be used as a reference when diagnosing a medical image that is a diagnostic interpretation object, a diagnostic interpretation teaching apparatus for diagnostic interpretation interns, and the like.

What is claimed is:

1. A control method of an information terminal, which is connected to a medical information management system that manages medical images that are diagnostic interpretation object candidates, and which is connected to a case retrieval system that refers to a medical image database in which medical images are registered and retrieves a medical image, and moreover which includes a display,
   one medical image of a site that is a diagnostic interpretation object selected from the diagnostic interpretation object candidates managed by the medical information management system being displayed on the display,
   the control method causing a computer of the information terminal to:
   sense specification information indicating a region of interest in the medical image;
   receive from the case retrieval system one or more similar medical images of the site, each having a prescribed degree of similarity with a feature quantity of the region of interest indicated by the specification information in accordance with the region of interest;
   display the medical image that is managed by the medical information management system in a first display region that is displayed on the display and display a plurality of similar medical images received from the case retrieval system in a second display region that differs from the first display, region;
   display on the display a lesion distribution list displaying a plurality of selectable terms representing different ways lesions are physically distributed and excluding terms representing anatomical body parts,
   wherein in response to selection of a first of the selectable lesion distributions, the computer retrieves and displays in the second display region, in accordance with first distribution information, similar medical images,
   wherein in response to selection of a second of the selectable lesion distributions, the computer retrieves and displays in the second display region, in accordance with second distribution information, similar medical images,
   wherein
   the first distribution information is for selecting a similar medical image in which a size of a region corresponding to the region of interest belongs to a prescribed first range, and the second distribution information is for selecting a similar medical image in which the size of the region corresponding to the region of interest belongs to a prescribed second range, and
   the first range indicates that the size of the region corresponding to the region of interest is wider than the prescribed range in a region of the site, and the second range is lower than the first range and indicates that the size of the region corresponding to the region of interest is a part of the region of the site.

2. The control method according to claim 1, wherein
   the first distribution information is information indicating a distribution belonging to a bilateral, a multiple, a diffuse, or a hematogenous category, and
   the second distribution information is information indicating a distribution belonging to a segmental or a bronchial category.

3. A non-transitory computer-readable recording medium which stores a program that is executed on an information terminal, which is connected to a medical information management system that manages medical images that are diagnostic interpretation object candidates, and which is connected to a case retrieval system that refers to a medical image database in which medical images are registered and retrieves a medical image, and moreover which includes a display,
   one medical image of a site that is a diagnostic interpretation object selected from the diagnostic interpretation object candidates managed by the medical information management system being displayed on the display,
   the program causing a computer of the information terminal to:
   sense specification information indicating a region of interest in the medical image;
   receive from the case retrieval system one or more similar medical images of the site, each having a prescribed degree of similarity with a feature quantity of the region of interest indicated by the specification information in accordance with the region of interest;
   display the medical image that is managed by the medical information management system in a first display region that is displayed on the display and display a plurality of similar medical images received from the case retrieval system in a second display region that differs from the first display region;
   display on the display a lesion distribution list displaying a plurality of selectable terms representing different ways lesions are physically distributed and excluding terms representing anatomical body parts,
   wherein in response to selection of a first of the selectable lesion distributions, the computer retrieves and displays in the second display region, in accordance with first distribution information, similar medical images,
   wherein in response to selection of a second of the selectable lesion distributions, the computer retrieves and displays in the second display region, in accordance with second distribution information, similar medical images, and wherein
   the first distribution information is for selecting a similar medical image in which a size of a region corresponding to the region of interest belongs to a prescribed first range, and the second distribution information is for selecting a similar medical image in which the size of the region corresponding to the region of interest belongs to a prescribed second range, and
   the first range indicates that the size of the region corresponding to the region of interest is wider than the prescribed range in a region of the site, and the second range is lower than the first range and indicates that the size of the region corresponding to the region of interest is a part of the region of the site.

4. An information terminal which is connected to a medical information management system that manages medical images that are diagnostic interpretation object candidates, and which is connected to a case retrieval system that refers to a medical image database in which medical images are registered and retrieves a medical image, and moreover which includes a display, one medical image of a site that is a diagnostic interpretation object selected from the diagnostic interpretation object candidates managed by the medical information management system being displayed on the display, the information terminal including a computer which executes:

sensing specification information indicating a region of interest in the medical image;

receiving from the case retrieval system one or more similar medical images of the site, each having a prescribed degree of similarity with a feature quantity of the region of interest indicated by the specification information in accordance with the region of interest;

displaying the medical image that is managed by the medical information management system in a first display region that is displayed on the display and display a plurality of similar medical images received from the case retrieval system in a second display region that differs from the first display region;

displaying on the display a lesion distribution list displaying a plurality of selectable terms representing different ways lesions are physically distributed and excluding terms representing anatomical body parts, wherein in response to selection of a first of the selectable lesion distributions, the computer retrieves and displays in the second display region, in accordance with first distribution information, similar medical images, wherein in response to selection of a second of the selectable lesion distributions, the computer retrieves and displays in the second display region, in accordance with second distribution information, similar medical images, wherein the first distribution information is for selecting a similar medical image in which a size of a region corresponding to the region of interest belongs to a prescribed first range, and the second distribution information is for selecting a similar medical image in which the size of the region corresponding to the region of interest belongs to a prescribed second range, and the first range indicates that the size of the region corresponding to the region of interest is wider than the prescribed range in a region of the site, and the second range is lower than the first range and indicates that the size of the region corresponding to the region of interest is a part of the region of the site.

5. The control method according to claim 1, wherein the displayed distribution list displays the plurality of selectable terms representing different lesion distributions, including at least two of diffuse,
segmental,
bronchial,
bilateral,
multiple,
subpleural, and
hematogenous.

6. The non-transitory computer-readable recording medium according to claim 3, wherein the displayed distribution list displays the plurality of selectable terms representing different lesion distributions, including at least two of diffuse,
segmental,
bronchial,
bilateral,
multiple,
subpleural, and
hematogenous.

7. The information terminal according to claim 4, wherein the displayed distribution list displays the plurality of selectable terms representing different lesion distributions, including at least two of diffuse,
segmental,
bronchial,
bilateral,
multiple,
subpleural, and
hematogenous.

8. A control method of an information terminal according to claim 1, the control method causing the computer of the information terminal to thumbnail views of a plurality of similar medical images received from the case retrieval system in a second display region that differs from the first display region, wherein in response to selection of a first of the selectable lesion distributions, the computer retrieves and displays in the second display region, in accordance with first distribution information, thumbnail views of similar medical images each of whose legion distributions corresponds to the selected first legion distribution, and each of which has a region, corresponding to the region of interest of the one medical image, whose size belongs to a prescribed first range wider than a prescribed range of a region of the site of the one medical image, and wherein in response to selection of a second of the selectable lesion distributions, the computer retrieves and displays in the second display region, in accordance with second distribution information, thumbnail views of similar medical images each of whose legion distributions corresponds to the selected second legion distribution, and each of which has a region, corresponding to the region of interest of the one medical image, whose size belongs to a prescribed second range that is part of the region of the site of the one medical image.

9. A control method of an information terminal according to claim 8, wherein in response to selection of a first of the selectable lesion distributions, the computer retrieves and displays in the second display region, in accordance with first distribution information, thumbnail views of a first magnification of similar medical images, wherein in response to selection of a second of the selectable lesion distributions, the computer retrieves and displays in the second display region, in accordance with second distribution information, thumbnail views of a second magnification of similar medical images, and wherein the first magnification is the same as the second magnification.

10. A control method of an information terminal according to claim 8,
wherein in response to selection of a second of the selectable lesion distributions, the computer retrieves and displays in the second display region, in accordance with second distribution information, thumbnail views of similar medical images
each of whose legion distributions corresponds to the selected second legion distribution, and
each of which has a region, corresponding to the region of interest of the one medical image,
whose size belongs to a prescribed second range that is part of the region of the site of the one medical image, and
which is displayed in the center of the second display region.

11. A control method of an information terminal according to claim 8,
wherein in response to selection of a first of the selectable lesion distributions, the computer retrieves and displays in the second display region, in accordance with first distribution information, thumbnail views of a first magnification of similar medical images,
wherein in response to selection of a second of the selectable lesion distributions, the computer retrieves and displays in the second display region, in accordance with second distribution information, thumbnail views of a second magnification of similar medical images,
wherein the second magnification is greater than the first magnification, and
wherein in response to selection of a second of the selectable lesion distributions, the computer retrieves and displays in the second display region, in accordance with second distribution information, thumbnail views of similar medical images
each of which has a region, corresponding to the region of interest of the one medical image, which is displayed in the center of the second display region.

12. A control method of an information terminal according to claim 10,
wherein in response to selection of a first of the selectable lesion distributions, the computer retrieves and displays in the second display region, in accordance with first distribution information, thumbnail views of similar medical images
each of which is displayed without its display position within the first display region being adjusted so that a center of the region, corresponding to the region of interest of the one medical image, is positioned at a center of the first display region.

* * * * *